US006540741B1

(12) United States Patent
Underwood et al.

(10) Patent No.: US 6,540,741 B1
(45) Date of Patent: *Apr. 1, 2003

(54) SYSTEMS AND METHODS FOR ELECTROSURGICAL SPINE SURGERY

(75) Inventors: Ronald A. Underwood, Belmont, CA (US); Terry S. Davison, Cupertino, CA (US); Hira V. Thapliyal, Los Altos, CA (US); Philip E. Eggers, Dublin, OH (US)

(73) Assignee: Arthrocare Corporation, Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/412,103

(22) Filed: Oct. 4, 1999

Related U.S. Application Data

(60) Division of application No. 09/026,851, filed on Feb. 20, 1998, now Pat. No. 6,277,112, which is a continuation-in-part of application No. 08/690,159, filed on Jul. 18, 1996, now Pat. No. 5,902,272, which is a continuation-in-part of application No. 08/942,580, filed on Oct. 2, 1997, now Pat. No. 6,159,184.

(51) Int. Cl.$^7$ ............................................... A61B 18/14
(52) U.S. Cl. ............................ 606/32; 606/41; 604/35; 604/114; 607/99; 607/105; 607/113
(58) Field of Search ............................. 606/32, 34, 41, 606/49, 50; 607/99, 105, 113; 604/35, 114

(56) References Cited

U.S. PATENT DOCUMENTS

| 6,007,570 A | * | 12/1999 | Sharkey et al. | ............... 607/96 |
| 6,073,051 A | * | 6/2000 | Sharkey et al. | ............... 607/67 |
| 6,277,112 B1 | * | 8/2001 | Underwood et al. | .......... 606/41 |

* cited by examiner

Primary Examiner—Lee Cohen
(74) Attorney, Agent, or Firm—John T. Raffle; Sanjay J. Bagade

(57) ABSTRACT

The present invention provides systems and methods for selectively applying electrical energy to a target location within of a patient's body, particularly including tissue in the spine. The present invention applies high frequency (RF) electrical energy to one or more electrode terminals in the presence of electrically conductive fluid to remove, contract or otherwise modify the structure of tissue structures. In one aspect of the invention, a method is provided for treating herniated discs within a patient's spine by applying sufficient electrical energy to the disc tissue to reduce a volume of the disc, thereby relieving pressure on a spinal nerve. In one embodiment, the high frequency voltage is sufficient to ablate a portion of the nucleus pulposis, either the extruded portion outside of the annulus or a portion or all of the pulposis within the annulus. In another embodiment, the electrode terminal is advanced into the annulus and sufficient high frequency voltage is applied to contract or shrink the collagen fibers within the nucleus pulposis. This causes the pulposis to shrink and withdraw from its impingement on the spinal nerve.

32 Claims, 33 Drawing Sheets

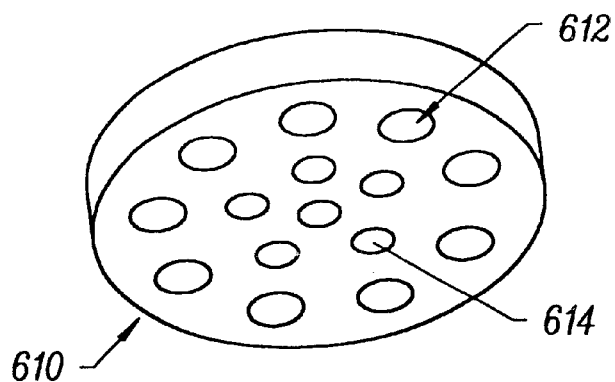
FIG. 11A
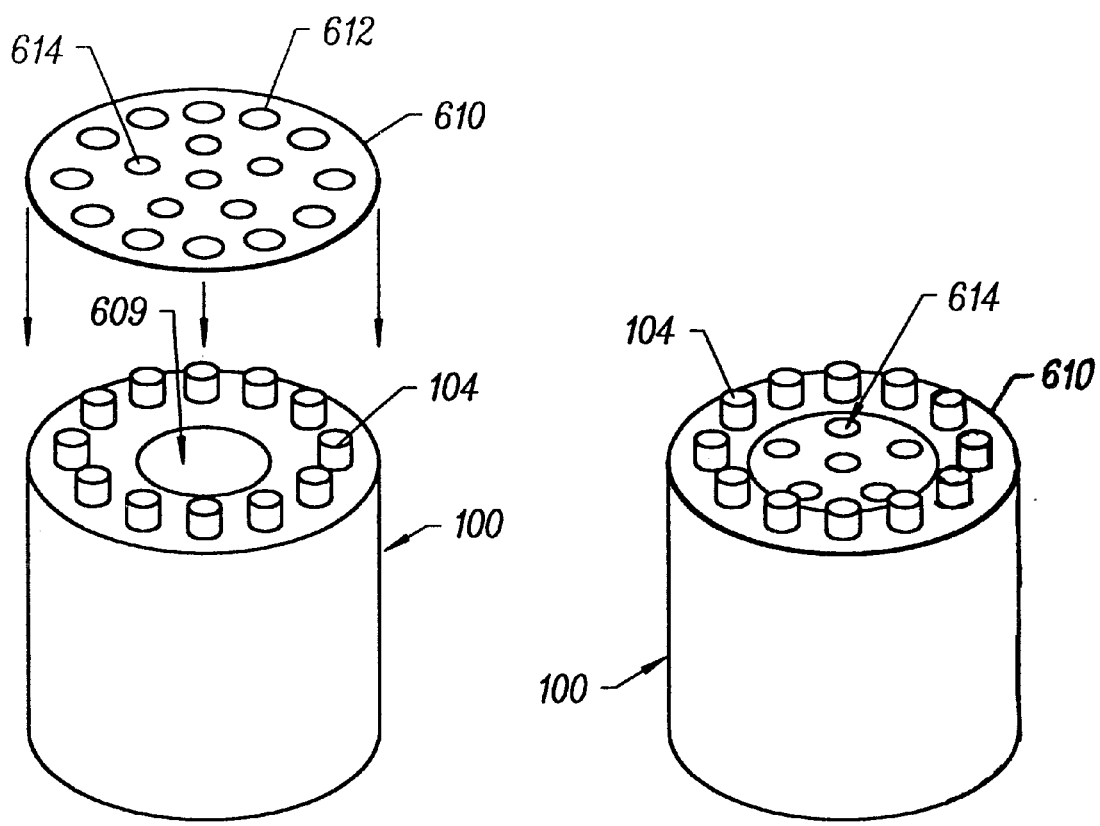
FIG. 11B
FIG. 11C

SYSTEMS AND METHODS FOR ELECTROSURGICAL SPINE SURGERY

RELATED APPLICATIONS

This application is a division of U.S. patent application Ser. No. 09/026,851 filed on Feb. 20, 1998, now U.S. Pat. No. 6,277,112, which application is a continuation-in-part of U.S. patent application Ser. No. 08/690,159, filed Jul. 18, 1996, now U.S. Pat. No. 5,902,272, the complete disclosure of which is incorporated herein by reference for all purposes. This application which is also continuation-in-part of U.S. patent application Ser. No. 08/942,580 entitled "Systems and Methods for Electrosurgical Tissue Contraction", filed on Oct. 2, 1997, U.S. Pat. No. 6,159,184 and U.S. patent application Ser. No. 08/990,374 entitled "Systems and Methods for Endoscopic Sinus Surgery", filed on Dec. 15, 1997, the complete disclosures of which are incorporated herein by reference for all purposes.

The present invention is related to commonly assigned co-pending Provisional Patent Application Nos. 60/062,996 and 60/062,997, non-provisional U.S. patent application Ser. No. 08/970,239 entitled "Electrosurgical Systems and Methods for Treating the Spine", filed Nov. 14, 1997 and Ser. No. 08/977,845 entitled "Systems and Methods for Electrosurgical Dermatological Treatment", filed on Nov. 25, 1997, U.S. application Ser. No. No. 08/753,227, filed on Nov. 22, 1996, and PCT International Application, U.S. National Phase Serial No. PCT/US94/05168, filed on May 10, 1994, now U.S. Pat. No. 5,697,281, which was a continuation-in-part of application Ser. No. 08/059,681, filed on May 10, 1993, which was a continuation-in-part of application Ser. No. 07/958,977, filed on Oct. 9, 1992 which was a continuation-in-part of application Ser. No. 07/817,575, filed on Jan. 7, 1992, the complete disclosures of which are incorporated herein by reference for all purposes. The present invention is also related to commonly assigned U.S. Pat. No. 5,683,366, filed Nov. 22, 1995, and U.S. Pat. No. 5,697,536, filed on Jun. 2, 1995, the complete disclosures of which are incorporated herein by reference for all purposes.

BACKGROUND OF THE INVENTION

The present invention relates generally to the field of electrosurgery, and more particularly to surgical devices and methods which employ high frequency electrical energy to treat tissue in regions of the spine. The present invention is particularly suited for the treatment of herniated discs.

The major causes of persistent, often disabling, back pain are disruption of the disc annulus, chronic inflammation of the disc (e.g., herniation), or relative instability of the vertebral bodies surrounding a given disc, such as the instability that often occurs due to a degenerative disease. Spinal discs mainly function to cushion and tether the vertebrae, providing flexibility and stability to the patient's spine. Spinal discs comprise a central hydrostatic cushion, the nucleus pulposus, surrounded by a multi-layered ligament, the annulus fibrosis. As discs degenerate, they lose their water content and height, bring vertebrae closer together. This results in a weakening of the shock absorption properties of the disc and a narrowing of the nerve openings in the sides of the spine which may pinch your nerve. This disc degeneration can eventually cause back and leg pain. Weakness in the annulus from degenerative discs or disc injury can allow fragments of nucleus pulposis from within the disc space to migrate into the spinal canal. There, displaced nucleus or protrusion of annulus fibrosis, e.g., herniation, may impinge on spinal nerves. The mere proximity of the nucleus pulposis or a damaged annulus to a nerve can cause direct pressure against the nerve, resulting in numbness and weakness of leg muscles.

Often, inflammation from disc herniation can be treated successfully by nonsurgical means, such as rest, therapeutic exercise, oral anti-inflammatory medications or epidural injection of corticosteroids. In some cases, the disc tissue is irreparably damaged, thereby necessitating removal of a portion of the disc or the entire disc to eliminate the source of inflammation and pressure. In more severe cases, the adjacent vertebral bodies must be stabilized following excision of the disc material to avoid recurrence of the disabling back pain. One approach to stabilizing the vertebrae, termed spinal fusion, is to insert an interbody graft or implant into the space vacated by the degenerative disc. In this procedure, a small amount of bone may be grafted from other portions of the body, such as the hip, and packed into the implants. This allows the bone to grow through and around the implant, fusing the vertebral bodies and alleviating the pain.

Until recently, spinal discectomy and fusion procedures resulted in major operations and traumatic dissection of muscle and bone removal or bone fusion. To overcome the disadvantages of traditional traumatic spine surgery, ninimally invasive spine surgery was developed. In endoscopic spinal procedures, the spinal canal is not violated and therefore epidural bleeding with ensuring scarring is minimized or completely avoided. In addition, the risk of instability from ligament and bone removal is generally lower in endoscopic procedures than with open discectomy. Further, more rapid rehabilitation facilitates faster recovery and return to work.

Minimally invasive techniques for the treatment of spinal diseases or disorders include chemonucleolysis, laser techniques and mechanical techniques. These procedures generally require the surgeon to form a passage or operating corridor from the external surface of the patient to the spinal disc(s) for passage of surgical instruments, implants and the like. Typically, the formation of this operating corridor requires the removal of soft tissue, muscle or other types of tissue depending on the procedure (i.e., laparascopic, thoracoscopic, arthroscopic, back, etc.). This tissue is usually removed with mechanical instruments, such as pituitary rongeurs, curettes, graspers, cutters, drills, microdebriders and the like. Unfortunately, these mechanical instruments greatly lengthen and increase the complexity of the procedure. In addition, these instruments sever blood vessels within this tissue, usually causing profuse bleeding that obstructs the surgeon's view of the target site.

Once the operating corridor is established, the nerve root is retracted and a portion or all of the disc is removed with mechanical instruments, such as a pituitary rongeur. In addition to the above problems with mechanical instruments, there are serious concerns because these instruments are not precise, and it is often difficult, during the procedure, to differentiate between the target disc tissue, and other structures within the spine, such as bone, cartilage, ligaments, nerves and non-target tissue. Thus, the surgeon must be extremely careful to minimize damage to the cartilage and bone within the spine, and to avoid damaging nerves, such as the spinal nerves and the dura mater surrounding the spinal cord.

Lasers were initially considered ideal for spine surgery because lasers ablate or vaporize tissue with heat, which also acts to cauterize and seal the small blood vessels in the tissue. Unfortunately, lasers are both expensive and somewhat tedious to use in these procedures. Another disadvantage with lasers is the difficulty in judging the depth of tissue ablation. Since the surgeon generally points and shoots the laser without contacting the tissue, he or she does not receive any tactile feedback to judge how deeply the laser is cutting. Because healthy tissue, bones, ligaments and spinal nerves often lie within close proximity of the spinal disc, it is essential to maintain a minimum depth of tissue damage, which cannot always be ensured with a laser.

Monopolar radiofrequency devices have been used in limited roles in spine surgery, such as to cauterize severed vessels to improve visualization. These monopolar devices, however, suffer from the disadvantage that the electric current will flow through undefined paths in the patient's body, thereby increasing the risk of unwanted electrical stimulation to portions of the patient's body. In addition, since the defined path through the patient's body has a relatively high impedance (because of the large distance or resistivity of the patient's body), large voltage differences must typically be applied between the return and active electrodes in order to generate a current suitable for ablation or cutting of the target tissue. This current, however, may inadvertently flow along body paths having less impedance than the defined electrical path, which will substantially increase the current flowing through these paths, possibly causing damage to or destroying surrounding tissue or neighboring peripheral nerves.

SUMMARY OF THE INVENTION

The present invention provides systems, apparatus and methods for selectively applying electrical energy to structures within a patient's body, such as tissue within or around the spine. The systems and methods of the present invention are particularly useful for ablation, resection, aspiration, collagen shrinkage and/or hemostasis of tissue and other body structures in open and endoscopic spine surgery.

In one aspect of the invention, a method is provided for treating herniated discs within a patient's spine. Specifically, the method of the present invention comprises introducing an electrosurgical probe within the spine (either endoscopically, or through an open procedure) so that one or more electrode terminal(s) are brought into at least partial contact or close proximity with the target herniated disc. High frequency voltage is then applied between the electrode terminal(s) and one or more return electrode(s) to apply sufficient energy to the disc tissue to reduce a volume of the disc, thereby relieving pressure on a spinal nerve. In one embodiment, the high frequency voltage is sufficient to ablate a portion of the nucleus pulposis, either the extruded portion outside of the annulus or a portion or all of the pulposis within the annulus. In another embodiment, the electrode terminal is advanced into the annulus and sufficient high frequency voltage is applied to contract or shrink the collagen fibers within the nucleus pulposis. This causes the pulposis to shrink and withdraw from its impingement on the spinal nerve. In other embodiments, the present invention may be used to both ablate the extruded portion of the nucleus pulposis, and then to contract or shrink the inner disc material to allow repair of the annulus.

In a specific configuration, electrically conducting fluid, such as isotonic saline, is directed to the target site between the target disc tissue and the electrode terminal. In monopolar embodiments, the conductive fluid need only be sufficient to surround the electrode terminal, and to provide a layer of fluid between the terminal and the tissue. In bipolar embodiments, the conductive fluid preferably generates a current flow path between the electrode terminal(s) and one or more return electrode(s).

In procedures requiring contraction of tissue, high frequency voltage is applied to the electrode terminal(s) to elevate the temperature of collagen fibers within the tissue at the target site from body temperature (about 37° C.) to a tissue temperature in the range of about 45° C. to 90° C., usually about 60° C. to 70° C., to substantially irreversibly contract these collagen fibers. In a preferred embodiment, an electrically conducting fluid is provided between the electrode terminal(s) and one or more return electrode(s) positioned proximal to the electrode terminal(s) to provide a current flow path from the electrode terminal(s) away from the tissue to the return electrode (s). The current flow path may be generated by directing an electrically conducting fluid along a fluid path past the return electrode and to the target site, or by locating a viscous electrically conducting fluid, such as a gel, at the target site, and submersing the electrode terminal(s) and the return electrode(s) within the conductive gel. The collagen fibers may be heated either by passing the electric current through the tissue to a selected depth before the current returns to the return electrode(s) and/or by heating the electrically conducting fluid and generating a jet or plume of heated fluid, which is directed towards the target tissue. In the latter embodiment, the electric current may not pass into the tissue at all. In both embodiments, the heated fluid and/or the electric current elevates the temperature of the collagen sufficiently to cause hydrothermal shrinkage of the collagen fibers.

In procedures requiring ablation of tissue, the tissue is removed by molecular dissociation or disintegration processes. In these embodiments, the high frequency voltage applied to the electrode terminal(s) is sufficient to vaporize an electrically conductive fluid (e.g., gel or saline) between the electrode terminal(s) and the tissue. Within the vaporized fluid, a ionized plasma is formed and charged particles (e.g., electrons) are accelerated towards the tissue to cause the molecular breakdown or disintegration of several cell layers of the tissue. This molecular dissociation is accompanied by the volumetric removal of the tissue. The short range of the accelerated charged particles within the plasma layer confines the molecular dissociation process to the surface layer to minimize damage and necrosis to the underlying tissue. This process can be precisely controlled to effect the volumetric removal of tissue as thin as 10 to 150 microns with minimal heating of, or damage to, surrounding or underlying tissue structures. A more complete description of this phenomena is described in commonly assigned U.S. Pat. No. 5,683,366, the complete disclosure of which is incorporated herein by reference.

In another aspect of the invention, the present invention is useful for helping to create an operating corridor or passage between a percutaneous penetration in the patient's outer skin and a target area within the spine. Typically, this operating corridor is initially created by inserting one or more dilators through the percutaneous penetration to the target area within the spine, and then introducing a tubular retractor or similar instrument over the largest dilator. Once this is accomplished, the hollow interior of the retractor (which will serve as the operating corridor for the introduction of the necessary instruments, such as the endoscope) is typically partially filled with soft tissue, muscle and other body structures. The present invention is particularly useful for precisely and quickly removing these body structures to clear the operating corridor. To that end, an electrosurgical probe according to the invention is delivered into the hollow retractor, and one or more electrode terminal(s) are positioned adjacent to or in contact with the soft tissue or other body structures to be removed. High frequency voltage is applied between the electrode terminal(s) and one or more return electrodes such that the tissue is removed.

The tissue may be completely ablated in situ with the mechanisms described above, or the tissue may be partially ablated and partially resected and aspirated from this operating corridor. In the latter embodiment, the method of the present invention further comprises aspirating tissue fragments and fluid through an aspiration lumen in the electrosurgical instrument or another instrument. In a preferred configuration, the probe will include one or more aspiration electrode(s) at or near the distal opening of the aspiration lumen. In this embodiment, high frequency voltage is applied between the aspiration electrode(s) and one or more return electrode(s) (which can be the same or different electrodes from the ones used to ablate tissue) to partially or completely ablate the tissue fragments as they are aspirated into the lumen, thus inhibiting clogging of the lumen and expediting the tissue removal process.

The present invention offers a number of advantages over current mechanical and laser techniques for spine surgery. The ability to precisely control the volumetric removal of tissue results in a field of tissue ablation or removal that is very defined, consistent and predictable. The shallow depth of tissue heating also helps to minimize or completely eliminate damage to healthy tissue structures, cartilage, bone and/or spinal nerves that are often adjacent the target tissue. In addition, small blood vessels within the tissue are simultaneously cauterized and sealed as the tissue is removed to continuously maintain hemostasis during the procedure. This increases the surgeon's field of view, and shortens the length of the procedure. Moreover, since the present invention allows for the use of electrically conductive fluid (contrary to prior art bipolar and monopolar electrosurgery techniques), isotonic saline may be used during the procedure. Saline is the preferred medium for irrigation because it has the same concentration as the body's fluids and, therefore, is not absorbed into the body as much as other fluids.

Apparatus according to the present invention generally include an electrosurgical probe or catheter having a shaft with proximal and distal ends, one or more electrode terminal(s) at the distal end and one or more connectors coupling the electrode terminal(s) to a source of high frequency electrical energy. For endoscopic spine surgery, the shaft will have a distal end portion sized to fit between adjacent vertebrae in the patient's spine. In some embodiments, the distal end portion is substantially planar, and it offers a low profile, to allow access to confined spaces without risking iatrogenic injury to surrounding body structures or nerves, such as vertebrae or spinal nerves. Usually, the distal end portion will have a combined height (i.e., including the active electrode(s)) of less than 2 mm and preferably less than 1 mm.

The apparatus will preferably further include a fluid delivery element for delivering electrically conducting fluid to the electrode terminal(s) and the target site. The fluid delivery element may be located on the probe, e.g., a fluid lumen or tube, or it may be part of a separate instrument. Alternatively, an electrically conducting gel or spray, such as a saline electrolyte or other conductive gel, may be applied the target site. In this embodiment, the apparatus may not have a fluid delivery element. In both embodiments, the electrically conducting fluid will preferably generate a current flow path between the electrode terminal(s) and one or more return electrode(s). In an exemplary embodiment, the return electrode is located on the probe and spaced a sufficient distance from the electrode terminal(s) to substantially avoid or minimize current shorting therebetween and to shield the return electrode from tissue at the target site.

In a specific configuration, the electrosurgical probe will include an electrically insulating electrode support member having a tissue treatment surface at the distal end of the probe. One or more electrode terminal(s) are coupled to, or integral with, the electrode support member such that the electrode terminal(s) are spaced from the return electrode. In one embodiment, the probe includes an electrode array having a plurality of electrically isolated electrode terminals embedded into the electrode support member such that the electrode terminals extend about 0.2 mm to about 10 mm distally from the tissue treatment surface of the electrode support member. In this embodiment, the probe will further include one or more lumens for delivering electrically conductive fluid to one or more openings around the tissue treatment surface of the electrode support member. In an exemplary embodiment, the lumen will extend through a fluid tube exterior to the probe shaft that ends proximal to the return electrode.

The system may optionally include a temperature controller coupled to one or more temperature sensors at or near the distal end of the probe. The controller adjusts the output voltage of the power supply in response to a temperature set point and the measured temperature value. The temperature sensor may be, for example, a thermocouple, located in the insulating support that measures a temperature at the distal end of the probe. In this embodiment, the temperature set point will preferably be one that corresponds to a tissue temperature that results, for example, in the contraction of the collagen tissue, i.e., about 60° C. to 70° C. Alternatively, the temperature sensor may directly measure the tissue temperature (e.g., infrared sensor).

BRIEF DESCRIPTION OF THE DRAWINGS

FIGS. 11A–11C illustrate an alternative embodiment incorporating a mesh electrode for ablating aspirated tissue fragments;

DESCRIPTION OF SPECIFIC EMBODIMENTS

Figure 1:
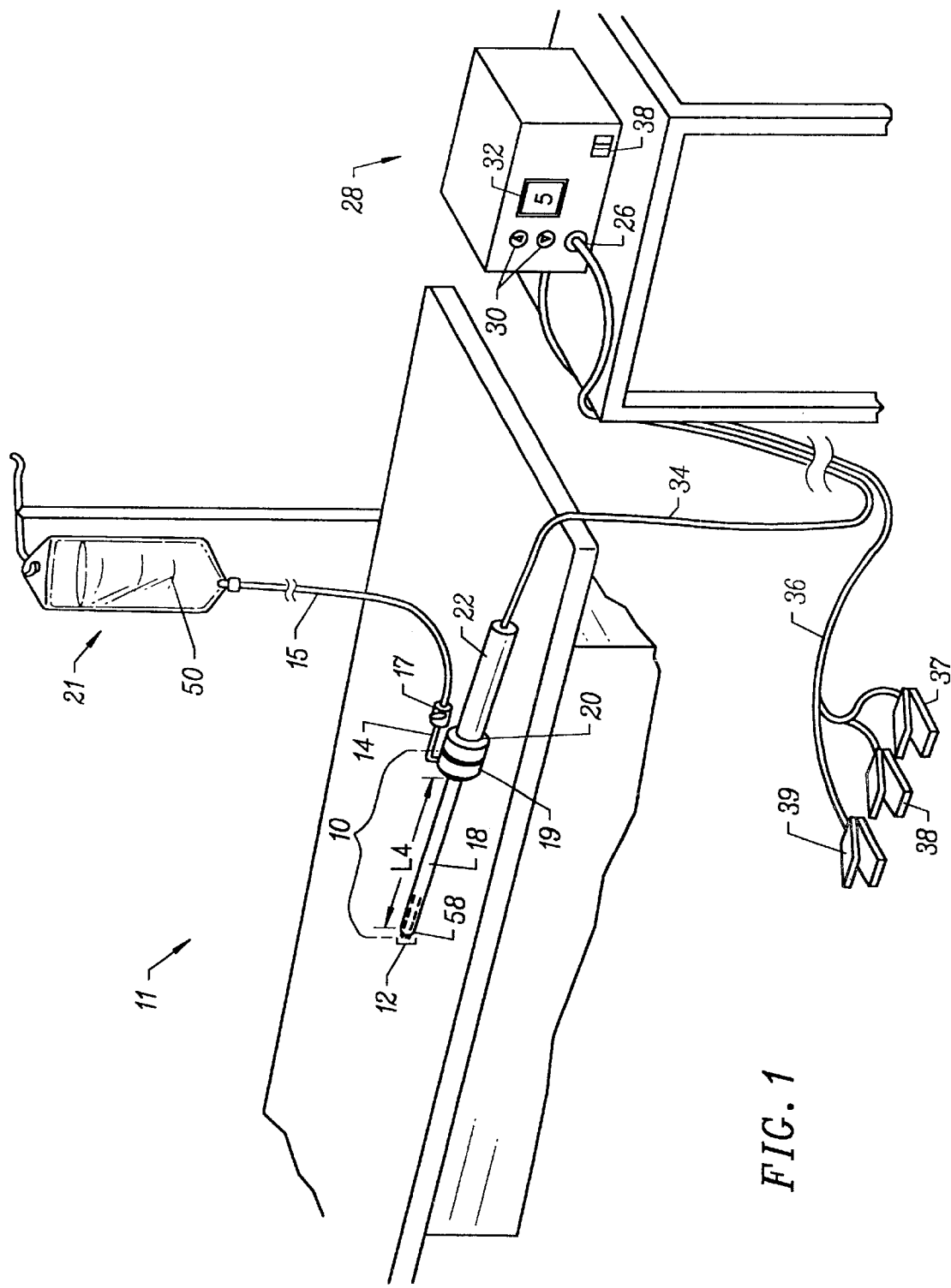
FIG. 1 is a perspective view of an electrosurgical system incorporating a power supply and an electrosurgical probe for tissue ablation, resection, incision, contraction and for vessel hemostasis according to the present invention.

The present invention provides systems and methods for selectively applying electrical energy to a target location within or on a patient's body, particularly including tissue or other body structures in the spine. These procedures include laminectomy/disketomy procedures for treating herniated disks, decompressive laminectomy for stenosis in the lumbosacral and cervical spine, medial facetectomy, posterior lumbosacral and cervical spine fusions, treatment of scoliosis associated with vertebral disease, foraminotomies to remove the roof of the intervertebral foramina to relieve nerve root compression and anterior cervical and lumbar diskectomies. These procedures may be performed through open procedures, or using minimally invasive techniques, such as thoracoscopy, arthroscopy, laparascopy or the like.

In the present invention, high frequency (RF) electrical energy is applied to one or more electrode terminals in the presence of electrically conductive fluid to remove and/or modify the structure of tissue structures. Depending on the specific procedure, the present invention may be used to: (1) volumetrically remove tissue, bone, ligament or cartilage (i.e., ablate or effect molecular dissociation of the body structure); (2) cut or resect tissue or other body structures; (3) shrink or contract collagen connective tissue; and/or (4) coagulate severed blood vessels.

In some procedures, e.g., shrinkage of nucleus pulposis in herniated discs, it is desired to shrink or contract collagen connective tissue at the target site. In these procedures, the RF energy heats the tissue directly by virtue of the electrical current flow therethrough, and/or indirectly through the exposure of the tissue to fluid heated by RF energy, to elevate the tissue temperature from normal body temperatures (e.g., 37° C.) to temperatures in the range of 45° C. to 90° C., preferably in the range from about 60° C. to 70° C. Thermal shrinkage of collagen fibers occurs within a small temperature range which, for mammalian collagen is in the range from 60° C. to 70° C. (Deak, G., et al., "The Thermal Shrinkage Process of Collagen Fibres as Revealed by Polarization Optical Analysis of Topooptical Staining Reactions," Acta Morphologica Acad. Sci. of Hungary, Vol. 15(2), pp 195–208, 1967). Collagen fibers typically undergo thermal shrinkage in the range of 60° C. to about 70° C. Previously reported research has attributed thermal shrinkage of collagen to the cleaving of the internal stabilizing cross-linkages within the collagen matrix (Deak, ibid). It has also been reported that when the collagen temperature is increased above 70° C., the collagen matrix begins to relax again and the shrinkage effect is reversed resulting in no net shrinkage (Allain, J. C., et al., "Isometric Tensions Developed During the Hydrothermal Swelling of Rat Skin," Connective Tissue Research, Vol. 7, pp 127–133, 1980). Consequently, the controlled heating of tissue to a precise depth is critical to the achievement of therapeutic collagen shrinkage. A more detailed description of collagen shrinkage can be found in U.S. patent application Ser. No. 08/942,580, filed Oct. 2, 1997, entitled 'SYSTEMS AND METHODS FOR ELECTROSURGICAL TISSUE CONTRACTION", previously incorporated herein by reference.

The preferred depth of heating to effect the shrinkage of collagen in the heated region (i.e., the depth to which the tissue is elevated to temperatures between 60° C. to 70° C.) generally depends on (1) the thickness of the tissue, (2) the location of nearby structures (e.g., nerves) that should not be exposed to damaging temperatures, and/or (3) the volume of contraction desired to relieve pressure on the spinal nerve. The depth of heating is usually in the range from 0 to 3.5 mm. In the case of collagen within the nucleus pulposis, the depth of heating is preferably in the range from about 0 to about 2.0 mm.

In another method of the present invention, the tissue structures are volumetrically removed or ablated. In this procedure, a high frequency voltage difference is applied between one or more electrode terminal(s) and one or more return electrode(s) to develop high electric field intensities in the vicinity of the target tissue site. The high electric field intensities lead to electric field induced molecular breakdown of target tissue through molecular dissociation (rather than thermal evaporation or carbonization). Applicant believes that the tissue structure is volumetrically removed through molecular disintegration of larger organic molecules into smaller molecules and/or atoms, such as hydrogen, oxides of carbon, hydrocarbons and nitrogen compounds. This molecular disintegration completely removes the tissue structure, as opposed to dehydrating the tissue material by the removal of liquid within the cells of the tissue, as is typically the case with electrosurgical desiccation and vaporization.

The high electric field intensities may be generated by applying a high frequency voltage that is sufficient to vaporize an electrically conducting fluid over at least a portion of the electrode terminal(s) in the region between the distal tip of the electrode terminal(s) and the target tissue. The electrically conductive fluid may be a gas or liquid, such as isotonic saline, delivered to the target site, or a viscous fluid, such as a gel, that is located at the target site. In the latter embodiment, the electrode terminal(s) are submersed in the electrically conductive gel during the surgical procedure. Since the vapor layer or vaporized region has a relatively high electrical impedance, it increases the voltage differential between the electrode terminal tip and the tissue and causes ionization within the vapor layer due to the presence of an ionizable species (e.g., sodium when isotonic saline is the electrically conducting fluid). This ionization, under optimal conditions, induces the discharge of energetic electrons and photons from the vapor layer and to the surface of the target tissue. This energy may be in the form of energetic photons (e.g., ultraviolet radiation), energetic particles (e.g., electrons) or a combination thereof. A more detailed description of this cold ablation phenomena, termed Coblation™, can be found in commonly assigned U.S. Pat. No. 5,683,366 the complete disclosure of which is incorporated herein by reference.

The present invention applies high frequency (RF) electrical energy in an electrically conducting fluid environment to remove (i.e., resect, cut or ablate) or contract a tissue structure, and to seal transected vessels within the region of the target tissue. The present invention is particularly useful for sealing larger arterial vessels, e.g., on the order of 1 mm or greater. In some embodiments, a high frequency power supply is provided having an ablation mode, wherein a first voltage is applied to an electrode terminal sufficient to effect molecular dissociation or disintegration of the tissue, and a coagulation mode, wherein a second, lower voltage is applied to an electrode terminal (either the same or a different electrode) sufficient to achieve hemostasis of severed vessels within the tissue. In other embodiments, an electrosurgical probe is provided having one or more coagulation electrode(s) configured for sealing a severed vessel, such as an arterial vessel, and one or more electrode terminals configured for either contracting the collagen fibers within the tissue or removing (ablating) the tissue, e.g., by applying sufficient energy to the tissue to effect molecular dissociation. In the latter embodiments, the coagulation electrode(s) may be configured such that a single voltage can be applied to coagulate with the coagulation electrode(s), and to ablate or contract with the electrode terminal(s). In other embodiments, the power supply is combined with the coagulation probe such that the coagulation electrode is used when the power supply is in the coagulation mode (low voltage), and the electrode terminal(s) are used when the power supply is in the ablation mode (higher voltage).

In the method of the present invention, one or more electrode terminals are brought into close proximity to tissue at a target site, and the power supply is activated in the ablation mode such that sufficient voltage is applied between the electrode terminals and the return electrode to volumetrically remove the tissue through molecular dissociation, as described below. During this process, vessels within the tissue will be severed. Smaller vessels will be automatically sealed with the system and method of the present invention. Larger vessels, and those with a higher flow rate, such as arterial vessels, may not be automatically sealed in the ablation mode. In these cases, the severed vessels may be sealed by activating a control (e.g., a foot pedal) to reduce the voltage of the power supply into the coagulation mode. In this mode, the electrode terminals may be pressed against the severed vessel to provide sealing and/or coagulation of the vessel. Alternatively, a coagulation electrode located on the same or a different probe may be pressed against the severed vessel. Once the vessel is adequately sealed, the surgeon activates a control (e.g., another foot pedal) to increase the voltage of the power supply back into the ablation mode.

The present invention is particularly useful for removing or ablating tissue around nerves, such as spinal or cranial nerves, e.g., the spinal cord and the surrounding dura mater. One of the significant drawbacks with the prior art cutters, graspers, and lasers is that these devices do not differentiate between the target tissue and the surrounding nerves or bone. Therefore, the surgeon must be extremely careful during these procedures to avoid damage to the bone or nerves within and around the spinal cord. In the present invention, the Coblation™ process for removing tissue results in extremely small depths of collateral tissue damage as discussed above. This allows the surgeon to remove tissue close to a nerve without causing collateral damage to the nerve fibers.

In addition to the generally precise nature of the novel mechanisms of the present invention, applicant has discovered an additional method of ensuring that adjacent nerves are not damaged during tissue removal. According to the present invention, systems and methods are provided for distinguishing between the fatty tissue immediately surrounding nerve fibers and the normal tissue that is to be removed during the procedure. Nerves usually comprise a connective tissue sheath, or endoneurium, enclosing the bundles of nerve fibers to protect these nerve fibers. This protective tissue sheath typically comprises a fatty tissue (e.g., adipose tissue) having substantially different electrical properties than the normal target tissue, such as the disc and other surrounding tissue that are, for example, removed from the spine during spinal procedures. The system of the present invention measures the electrical properties of the tissue at the tip of the probe with one or more electrode terminal(s). These electrical properties may include electrical conductivity at one, several or a range of frequencies (e.g., in the range from 1 kHz to 100 MHz), dielectric constant, capacitance or combinations of these. In this embodiment, an audible signal may be produced when the sensing electrode(s) at the tip of the probe detects the fatty tissue surrounding a nerve, or direct feedback control can be provided to only supply power to the electrode terminal(s) either individually or to the complete array of electrodes, if and when the tissue encountered at the tip or working end of the probe is normal tissue based on the measured electrical properties.

In one embodiment, the current limiting elements (discussed in detail above) are configured such that the electrode terminals will shut down or turn off when the electrical impedance reaches a threshold level. When this threshold level is set to the impedance of the fatty tissue surrounding nerves, the electrode terminals will shut off whenever they come in contact with, or in close proximity to, nerves. Meanwhile, the other electrode terminals, which are in contact with or in close proximity to nasal tissue, will continue to conduct electric current to the return electrode. This selective ablation or removal of lower impedance tissue in combination with the Coblation™ mechanism of the present invention allows the surgeon to precisely remove tissue around nerves or bone.

In addition to the above, applicant has discovered that the Coblation™ mechanism of the present invention can be manipulated to ablate or remove certain tissue structures, while having little effect on other tissue structures. As discussed above, the present invention uses a technique of vaporizing electrically conductive fluid to form a plasma layer or pocket around the electrode terminal(s), and then inducing the discharge of energy from this plasma or vapor layer to break the molecular bonds of the tissue structure. Based on initial experiments, applicants believe that the free electrons within the ionized vapor layer are accelerated in the high electric fields near the electrode tip(s). When the density of the vapor layer (or within a bubble formed in the electrically conducting liquid) becomes sufficiently low (i.e., less than approximately $10^{20}$ atoms/cm$^3$ for aqueous solutions), the electron mean free path increases to enable subsequently injected electrons to cause impact ionization within these regions of low density (i.e., vapor layers or bubbles). Energy evolved by the energetic electrons (e.g., 4 to 5 eV) can subsequently bombard a molecule and break its bonds, dissociating a molecule into free radicals, which then combine into final gaseous or liquid species.

The energy evolved by the energetic electrons may be varied by adjusting a variety of factors, such as: the number of electrode terminals; electrode size and spacing; electrode surface area; asperities and sharp edges on the electrode surfaces; electrode materials; applied voltage and power; current limiting means, such as inductors; electrical conductivity of the fluid in contact with the electrodes; density of the fluid; and other factors. Accordingly, these factors can be manipulated to control the energy level of the excited electrons. Since different tissue structures have different molecular bonds, the present invention can be configured to break the molecular bonds of certain tissue, while having too low an energy to break the molecular bonds of other tissue. For example, fatty tissue, (e.g., adipose) tissue has double bonds that require a substantially higher energy level than 4 to 5 eV to break. Accordingly, the present invention in its current configuration generally does not ablate or remove such fatty tissue. Of course, factors may be changed such that these double bonds can be broken (e.g., increasing voltage or changing the electrode configuration to increase the current density at the electrode tips).

The electrosurgical probe or catheter will comprise a shaft or a handpiece having a proximal end and a distal end which supports one or more electrode terminal(s). The shaft or handpiece may assume a wide variety of configurations, with the primary purpose being to mechanically support the active electrode and permit the treating physician to manipulate the electrode from a proximal end of the shaft. The shaft may be rigid or flexible, with flexible shafts optionally being combined with a generally rigid external tube for mechanical support. Flexible shafts may be combined with pull wires, shape memory actuators, and other known mechanisms for effecting selective deflection of the distal end of the shaft to facilitate positioning of the electrode array. The shaft will usually include a plurality of wires or other conductive elements running axially therethrough to permit connection of the electrode array to a connector at the proximal end of the shaft.

For endoscopic procedures within the spine, the shaft will have a suitable diameter and length to allow the surgeon to reach the target site (e.g., a disc) by delivering the shaft through the thoracic cavity, the abdomen or the like. Thus, the shaft will usually have a length in the range of about 5.0 to 30.0 cm, and a diameter in the range of about 0.2 mm to about 20 mm. Alternatively, the shaft may be delivered directly through the patient's back in a posterior approach, which would considerably reduce the required length of the shaft. In any of these embodiments, the shaft may also be introduced through rigid or flexible endoscopes. Specific shaft designs will be described in detail in connection with the figures hereinafter.

Figure 34:
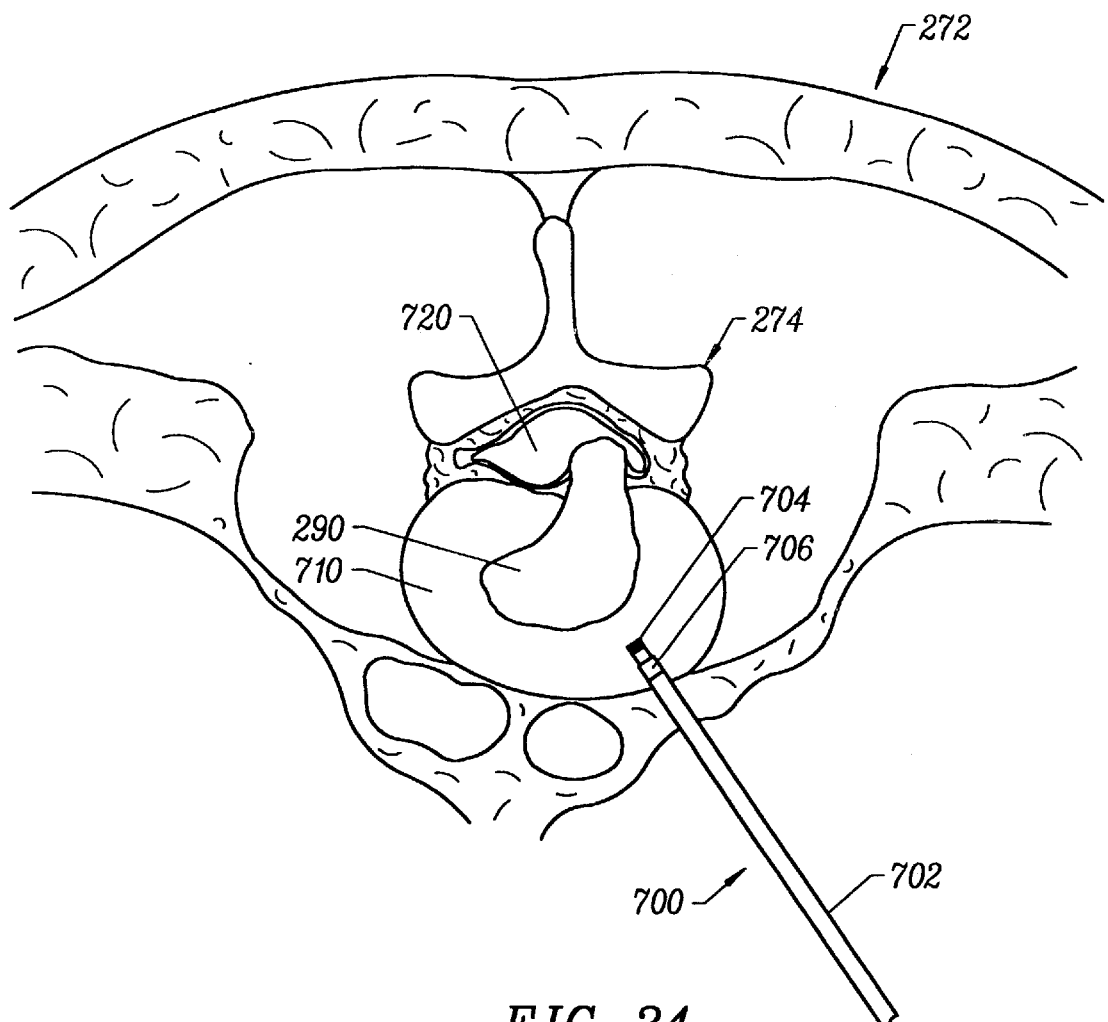
FIGS. 34–36 illustrates another system and method of the present invention for percutaneously contracting collagen fibers within a spinal disc with a small, needle-sized instrument.
Figure 35:
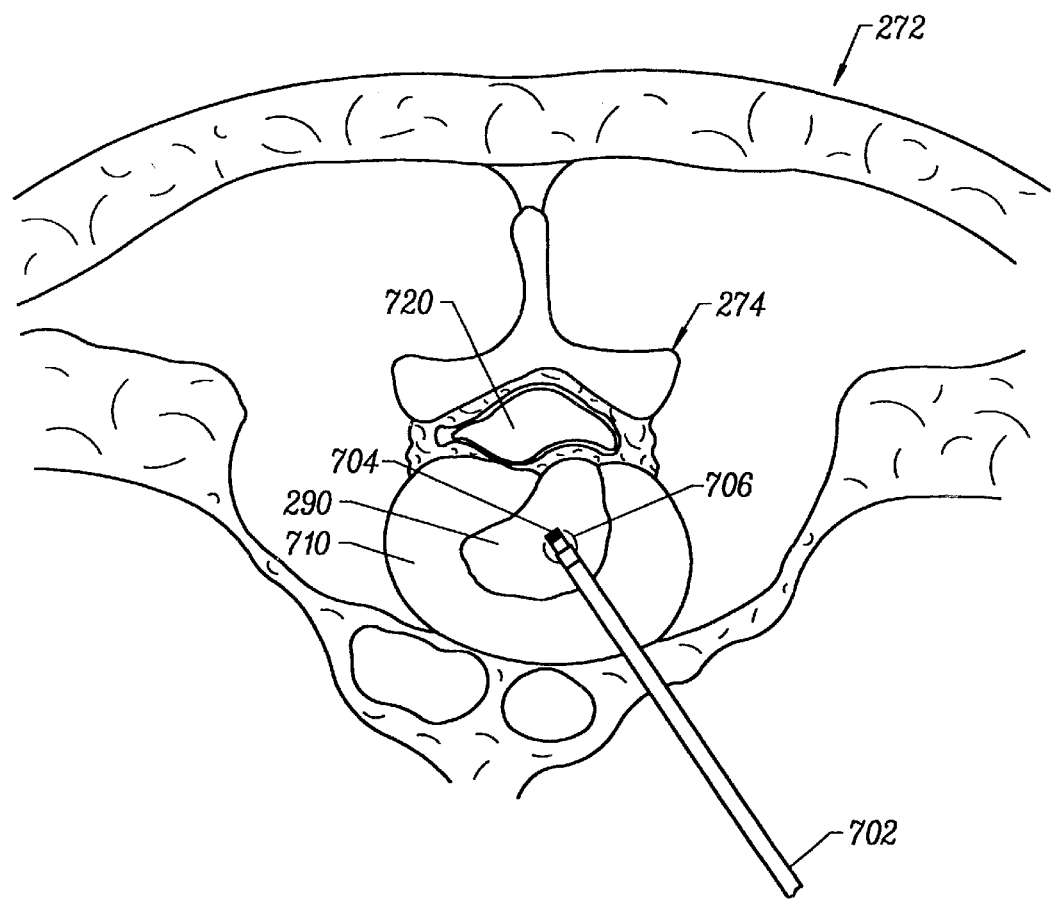
Figure 36:
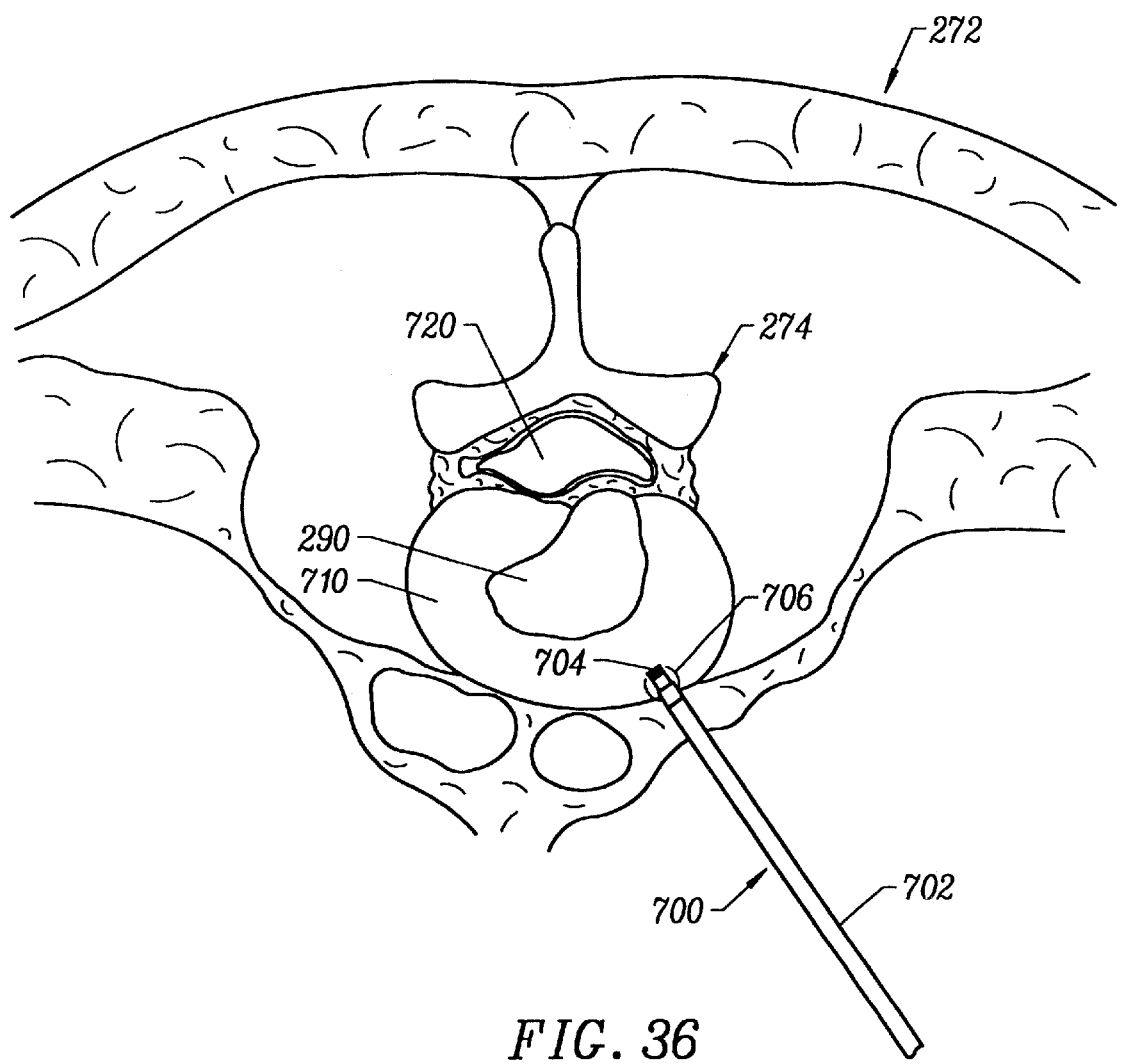

In an alternative embodiment, the probe may comprise a long, thin needle (e.g., on the order of about 1 mm in diameter or less) that can be percutaneously introduced through the patient's back directly into the spine (see FIGS. 34–36). The needle will include one or more active electrode (s) for applying electrical energy to tissues within the spine. The needle may include one or more return electrode(s), or the return electrode may be positioned on the patient's back, as a dispersive pad. In either embodiment, sufficient electrical energy is applied through the needle to the active electrode(s) to either shrink the collagen fibers within the spinal disk, or to ablate tissue within the disk.

The current flow path between the electrode terminal(s) and the return electrode(s) may be generated by submerging the tissue site in an electrical conducting fluid (e.g., within a liquid or a viscous fluid, such as an electrically conductive gel) or by directing an electrically conducting fluid along a fluid path to the target site (i.e., a liquid, such as isotonic saline, or a gas, such as argon). This latter method is particularly effective in a dry environment (i.e., the tissue is not submerged in fluid) because the electrically conducting fluid provides a suitable current flow path from the electrode terminal to the return electrode. A more complete description of an exemplary method of directing electrically conducting fluid between the active and return electrodes is described in U.S. Pat. No. 5,697,536, previously incorporated herein by reference.

In some procedures, it may also be necessary to retrieve or aspirate the electrically conductive fluid after it has been directed to the target site. In addition, it may be desirable to aspirate small pieces of tissue that are not completely disintegrated by the high frequency energy, or other fluids at the target site, such as blood, mucus, the gaseous products of ablation, etc. Accordingly, the system of the present invention will usually include a suction lumen in the probe, or on another instrument, for aspirating fluids from the target site. In addition, the invention may include one or more aspiration electrode(s) coupled to the distal end of the suction lumen for ablating, or at least reducing the volume of, non-ablated tissue fragments that are aspirated into the lumen. The aspiration electrode(s) function mainly to inhibit clogging of the lumen that may otherwise occur as larger tissue fragments are drawn therein. The aspiration electrode (s) may be different from the ablation electrode terminal(s), or the same electrode(s) may serve both functions. A more complete description of probes incorporating aspiration electrode(s) can be found in commonly assigned, co-pending patent application entitled "SYSTEMS AND METHODS FOR TISSUE RESECTION, ABLATION AND ASPIRATION", filed Jan. 21, 1998, the complete disclosure of which is incorporated herein by reference.

The present invention may use a single active electrode terminal or an electrode array distributed over a contact surface of a probe. In the latter embodiment, the electrode array usually includes a plurality of independently current-limited and/or powercontrolled electrode terminals to apply electrical energy selectively to the target tissue while limiting the unwanted application of electrical energy to the surrounding tissue and environment resulting from power dissipation into surrounding electrically conductive liquids, such as blood, normal saline, electrically conductive gel and the like. The electrode terminals may be independently current-limited by isolating the terminals from each other and connecting each terminal to a separate power source that is isolated from the other electrode terminals. Alternatively, the electrode terminals may be connected to each other at either the proximal or distal ends of the probe to form a single wire that couples to a power source.

In some embodiments, the active electrode(s) have an active portion or surface with surface geometries shaped to promote the electric field intensity and associated current density along the leading edges of the electrodes. Suitable surface geometries may be obtained by creating electrode shapes that include preferential sharp edges, or by creating asperities or other surface roughness on the active surface(s) of the electrodes. Electrode shapes according to the present invention can include the use of formed wire (e.g., by drawing round wire through a shaping die) to form electrodes with a variety of cross-sectional shapes, such as square, rectangular, L or V shaped, or the like. Electrode edges may also be created by removing a portion of the elongate metal electrode to reshape the cross-section. For example, material can be ground along the length of a round or hollow wire electrode to form D or C shaped wires, respectively, with edges facing in the cutting direction. Alternatively, material can be removed at closely spaced intervals along the electrode length to form transverse grooves, slots, threads or the like along the electrodes.

Additionally or alternatively, the active electrode surface(s) may be modified through chemical, electrochemical or abrasive methods to create a multiplicity of surface asperities on the electrode surface. These surface asperities will promote high electric field intensities between the active electrode surface(s) and the target tissue to facilitate ablation or cutting of the tissue. For example, surface asperities may be created by etching the active electrodes with etchants having a Ph less than 7.0 or by using a high velocity stream of abrasive particles (e.g., grit blasting) to create asperities on the surface of an elongated electrode.

The active electrode(s) are typically mounted in an electrically insulating electrode support that extends from the electrosurgical probe. In some embodiments, the electrode support comprises a plurality of wafer layers bonded together, e.g., by a glass adhesive or the like, or a single wafer. The wafer layer(s) have conductive strips printed thereon to form the electrode terminal(s) and the return electrode(s). In one embodiment, the proximal end of the wafer layer(s) will have a number of holes extending from the conductor strips to an exposed surface of the wafer layers for connection to electrical conductor lead traces in the electrosurgical probe or handpiece. The wafer layers preferably comprise a ceramic material, such as alumina, and the electrode win preferably comprise a metallic material, such as gold, copper, platinum, palladium, tungsten, silver or the like. Suitable multilayer ceramic electrodes are commercially available from e.g., VisPro Corporation of Beaverton, Oreg.

In one configuration, each individual electrode terminal in the electrode array is electrically insulated from all other electrode terminals in the array within said probe and is connected to a power source which is isolated from each of the other electrode terminals in the array or to circuitry which limits or interrupts current flow to the electrode terminal when low resistivity material (e.g., blood, electrically conductive saline irrigant or electrically conductive gel) causes a lower impedance path between the return electrode and the individual electrode terminal. The isolated power sources for each individual electrode terminal may be separate power supply circuits having internal impedance characteristics which limit power to the associated electrode terminal when a low impedance return path is encountered. By way of example, the isolated power source may be a user selectable constant current source. In this embodiment, lower impedance paths will automatically result in lower resistive heating levels since the heating is proportional to the square of the operating current times the impedance. Alternatively, a single power source may be connected to each of the electrode terminals through independently actuatable switches, or by independent current limiting elements, such as inductors, capacitors, resistors and/or combinations thereof. The current limiting elements may be provided in the probe, connectors, cable, controller or along the conductive path from the controller to the distal tip of the probe. Alternatively, the resistance and/or capacitance may occur on the surface of the active electrode terminal(s) due to oxide layers which form selected electrode terminals (e.g., titanium or a resistive coating on the surface of metal, such as platinum).

The tip region of the probe may comprise many independent electrode terminals designed to deliver electrical energy in the vicinity of the tip. The selective application of electrical energy to the conductive fluid is achieved by connecting each individual electrode terminal and the return electrode to a power source having independently controlled or current limited channels. The return electrode(s) may comprise a single tubular member of conductive material proximal to the electrode array at the tip which also serves as a conduit for the supply of the electrically conducting fluid between the active and return electrodes. Alternatively, the probe may comprise an array of return electrodes at the distal tip of the probe (together with the active electrodes) to maintain the electric current at the tip. The application of high frequency voltage between the return electrode(s) and the electrode array results in the generation of high electric field intensities at the distal tips of the electrode terminals with conduction of high frequency current from each individual electrode terminal to the return electrode. The current flow from each individual electrode terminal to the return electrode(s) is controlled by either active or passive means, or a combination thereof, to deliver electrical energy to the surrounding conductive fluid while minimizing energy delivery to surrounding (non-target) tissue.

The application of a high frequency voltage between the return electrode(s) and the electrode terminal(s) for appropriate time intervals effects cutting, removing, ablating, shaping, contracting or otherwise modifying the target tissue. The tissue volume over which energy is dissipated (i.e., a high current density exists) may be precisely controlled, for example, by the use of a multiplicity of small electrode terminals whose effective diameters or principal dimensions range from about 5 mm to 0.01 mm, preferably from about 2 mm to 0.05 mm, and more preferably from about 1 mm to 0.1 mm. Electrode areas for both circular and non-circular terminals will have a contact area (per electrode terminal) below 25 $mm^2$, preferably being in the range from 0.0001 $mm^2$ to 1 $mm^2$, and more preferably from 0.005 $mm^2$ to 0.5 $mm^2$. The circumscribed area of the electrode array is in the range from 0.25 $mm^2$ to 200 $mm^2$, preferably from 0.5 $mm^2$ to 100 $mm^2$, and will usually include at least two isolated electrode terminals, preferably at least five electrode terminals, often greater than 10 electrode terminals and even 50 or more electrode terminals, disposed over the distal contact surfaces on the shaft. The use of small diameter electrode terminals increases the electric field intensity and reduces the extent or depth of tissue heating as a consequence of the divergence of current flux lines which emanate from the exposed surface of each electrode terminal.

The area of the tissue treatment surface can vary widely, and the tissue treatment surface can assume a variety of geometries, with particular areas and geometries being selected for specific applications. Active electrode surfaces can have areas in the range from 0.25 mm$^2$ to 75 mm$^2$, usually being from about 0.5 mm$^2$ to 40 mm$^2$. The geometries can be planar, concave, convex, hemispherical, conical, linear "in-line" array or virtually any other regular or irregular shape. Most commonly, the active electrode(s) or electrode terminal(s) will be formed at the distal tip of the electrosurgical probe shaft, frequently being planar, disk-shaped, or hemispherical surfaces for use in reshaping procedures or being linear arrays for use in cutting. Alternatively or additionally, the active electrode(s) may be formed on lateral surfaces of the electrosurgical probe shaft (e.g., in the manner of a spatula), facilitating access to certain body structures in endoscopic procedures.

The electrically conducting fluid should have a threshold conductivity to provide a suitable conductive path between the return electrode(s) and the electrode terminal(s). The electrical conductivity of the fluid (in units of milliSiemans per centimeter or mS/cm) will usually be greater than 0.2 mS/cm, preferably will be greater than 2 mS/cm and more preferably greater than 10 mS/cm. In an exemplary embodiment, the electrically conductive fluid is isotonic saline, which has a conductivity of about 17 mS/cm. Alternatively, the fluid may be an electrically conductive gel or spray, such as a saline electrolyte gel, a conductive ECG spray, an electrode conductivity gel, an ultrasound transmission or scanning gel, or the like. Suitable gels or sprays are commercially available from Graham-Field, Inc of Hauppauge, N.Y.

In some embodiments, the electrode support and the fluid outlet may be recessed from an outer surface of the probe or handpiece to confine the electrically conductive fluid to the region immediately surrounding the electrode support. In addition, the shaft may be shaped so as to form a cavity around the electrode support and the fluid outlet. This helps to assure that the electrically conductive fluid will remain in contact with the electrode terminal(s) and the return electrode(s) to maintain the conductive path therebetween. In addition, this will help to maintain a vapor or plasma layer between the electrode terminal(s) and the tissue at the treatment site throughout the procedure, which reduces the thermal damage that might otherwise occur if the vapor layer were extinguished due to a lack of conductive fluid. Provision of the electrically conductive fluid around the target site also helps to maintain the tissue temperature at desired levels.

The voltage applied between the return electrode(s) and the electrode array will be at high or radio frequency, typically between about 5 kHz and 20 MHz, usually being between about 30 kHz and 2.5 MHz, preferably being between about 50 kHz and 500 kHz, more preferably less than 350 kHz, and most preferably between about 100 kHz and 200 kHz. The RMS (root mean square) voltage applied will usually be in the range from about 5 volts to 1000 volts, preferably being in the range from about 10 volts to 500 volts depending on the electrode terminal size, the operating frequency and the operation mode of the particular procedure or desired effect on the tissue (i.e., contraction, coagulation or ablation). Typically, the peak-to-peak voltage will be in the range of 10 to 2000 volts, preferably in the range of 20 to 1200 volts and more preferably in the range of about 40 to 800 volts (again, depending on the electrode size, the operating frequency and the operation mode).

As discussed above, the voltage is usually delivered in a series of voltage pulses or alternating current of time varying voltage amplitude with a sufficiently high frequency (e.g., on the order of 5 kHz to 20 MHz) such that the voltage is effectively applied continuously (as compared with e.g., lasers claiming small depths of necrosis, which are generally pulsed about 10 to 20 Hz). In addition, the duty cycle (i.e., cumulative time in any one-second interval that energy is applied) is on the order of about 50% for the present invention, as compared with pulsed lasers which typically have a duty cycle of about 0.0001%.

The preferred power source of the present invention delivers a high frequency current selectable to generate average power levels ranging from several milliwatts to tens of watts per electrode, depending on the volume of target tissue being heated, and/or the maximum allowed temperature selected for the probe tip. The power source allows the user to select the voltage level according to the specific requirements of a particular spine procedure, arthroscopic surgery, dermatological procedure, ophthalmic procedures, FESS procedure, open surgery or other endoscopic surgery procedure. A description of a suitable power source can be found in U.S. Provisional Patent Application No. 60/062, 997 entitled "SYSTEMS AND METHODS FOR ELECTROSURGICAL TISSUE AND FLUID COAGULATION", filed Oct. 23, 1997, the complete disclosure of which has been incorporated herein by reference.

The power source may be current limited or otherwise controlled so that undesired heating of the target tissue or surrounding- (non-target) tissue does not occur. In a presently preferred embodiment of the present invention, current limiting inductors are placed in series with each independent electrode terminal, where the inductance of the inductor is in the range of 10 uH to 50,000 uH, depending on the electrical properties of the target tissue, the desired tissue heating rate and the operating frequency. Alternatively, capacitor-inductor (LC) circuit structures may be employed, as described previously in co-pending PCT application No. PCT/US94/05168, the complete disclosure of which is incorporated herein by reference. Additionally, current limiting resistors may be selected. Preferably, these resistors will have a large positive temperature coefficient of resistance so that, as the current level begins to rise for any individual electrode terminal in contact with a low resistance medium (e.g., saline irrigant or conductive gel), the resistance of the current limiting resistor increases significantly, thereby minimizing the power delivery from said electrode terminal into the low resistance medium (e.g., saline irrigant or conductive gel).

It should be clearly understood that the invention is not limited to electrically isolated electrode terminals, or even to a plurality of electrode terminals. For example, the array of active electrode terminals may be connected to a single lead that extends through the probe shaft to a power source of high frequency current. Alternatively, the probe may incorporate a single electrode that extends directly through the probe shaft or is connected to a single lead that extends to the power source. The active electrode may have a ball shape (e.g., for tissue vaporization and desiccation), a twizzle shape (for vaporization and needle-like cutting), a spring shape (for rapid tissue debulking and desiccation), a twisted metal shape, an annular or solid tube shape or the like. Alternatively, the electrode may comprise a plurality of filaments, a rigid or flexible brush electrode (for debulking a tumor, such as a fibroid, bladder tumor or a prostate adenoma), a side-effect brush electrode on a lateral surface of the shaft, a coiled electrode or the like. In one embodiment, the probe comprises a single active electrode terminal that extends from an insulating member, e.g., ceramic, at the distal end of the probe. The insulating member is preferably a tubular structure that separates the active electrode terminal from a tubular or annular return electrode positioned proximal to the insulating member and the active electrode.

Referring to FIG. 1, an exemplary electrosurgical system 11 for treatment of tissue in the spine will now be described in detail. Electrosurgical system 11 generally comprises an electrosurgical handpiece or probe 10 connected to a power supply 28 for providing high frequency voltage to a target site and a fluid source 21 for supplying electrically conducting fluid 50 to probe 10. In addition, electrosurgical system 11 may include an endoscope (not shown) with a fiber optic head light for viewing the surgical site, particularly in endoscopic spine procedures. The endoscope may be integral with probe 10, or it may be part of a separate instrument. The system 11 may also include a vacuum source (not shown) for coupling to a suction lumen or tube 211 (see FIG. 2) in the probe 10 for aspirating the target site.

As shown, probe 10 generally includes a proximal handle 19 and an elongate shaft 18 having an array 12 of electrode terminals 58 at its distal end. A connecting cable 34 has a connector 26 for electrically coupling the electrode terminals 58 to power supply 28. The electrode terminals 58 are electrically isolated from each other and each of the terminals 58 is connected to an active or passive control network within power supply 28 by means of a plurality of individually insulated conductors (not shown). A fluid supply tube 15 is connected to a fluid tube 14 of probe 10 for supplying electrically conducting fluid 50 to the target site.

Power supply 28 has an operator controllable voltage level adjustment 30 to change the applied voltage level, which is observable at a voltage level display 32. Power supply 28 also includes first, second and third foot pedals 37, 38, 39 and a cable 36 which is removably coupled to power supply 28. The foot pedals 37, 38, 39 allow the surgeon to remotely adjust the energy level applied to electrode terminals 58. In an exemplary embodiment, first foot pedal 37 is used to place the power supply into the "ablation" mode and second foot pedal 38 places power supply 28 into the "coagulation" mode. The third foot pedal 39 allows the user to adjust the voltage level within the "ablation" mode. In the ablation mode, a sufficient voltage is applied to the electrode terminals to establish the requisite conditions for molecular dissociation of the tissue (i.e., vaporizing a portion of the electrically conductive fluid, ionizing charged particles within the vapor layer and accelerating these charged particles against the tissue). As discussed above, the requisite voltage level for ablation will vary depending on the number, size, shape and spacing of the electrodes, the distance in which the electrodes extend from the support member, etc. Once the surgeon places the power supply in the "ablation" mode, voltage level adjustment 30 or third foot pedal 39 may be used to adjust the voltage level to adjust the degree or aggressiveness of the ablation.

Of course, it will be recognized that the voltage and modality of the power supply may be controlled by other input devices. However, applicant has found that foot pedals are convenient methods of controlling the power supply while manipulating the probe during a surgical procedure.

In the coagulation mode, the power supply 28 applies a low enough voltage to the electrode terminals (or the coagulation electrode) to avoid vaporization of the electrically conductive fluid and subsequent molecular dissociation of the tissue. The surgeon may automatically toggle the power supply between the ablation and coagulation modes by alternatively stepping on foot pedals 37, 38, respectively. This allows the surgeon to quickly move between coagulation and ablation in situ, without having to remove his/her concentration from the surgical field or without having to request an assistant to switch the power supply. By way of example, as the surgeon is sculpting soft tissue in the ablation mode, the probe typically will simultaneously seal and/or coagulation small severed vessels within the tissue. However, larger vessels, or vessels with high fluid pressures (e.g., arterial vessels) may not be sealed in the ablation mode. Accordingly, the surgeon can simply step on foot pedal 38, automatically lowering the voltage level below the threshold level for ablation, and apply sufficient pressure onto the severed vessel for a sufficient period of time to seal and/or coagulate the vessel. After this is completed, the surgeon may quickly move back into the ablation mode by stepping on foot pedal 37. A specific design of a suitable power supply for use with the present invention can be found in U.S. Provisional Patent Application No. 60/062,997, entitled "SYSTEMS AND METHODS FOR ELECTROSURGICAL TISSUE AND FLUID COAGULATION", filed Oct. 23, 1997, previously incorporated herein by reference.

Figure 2:
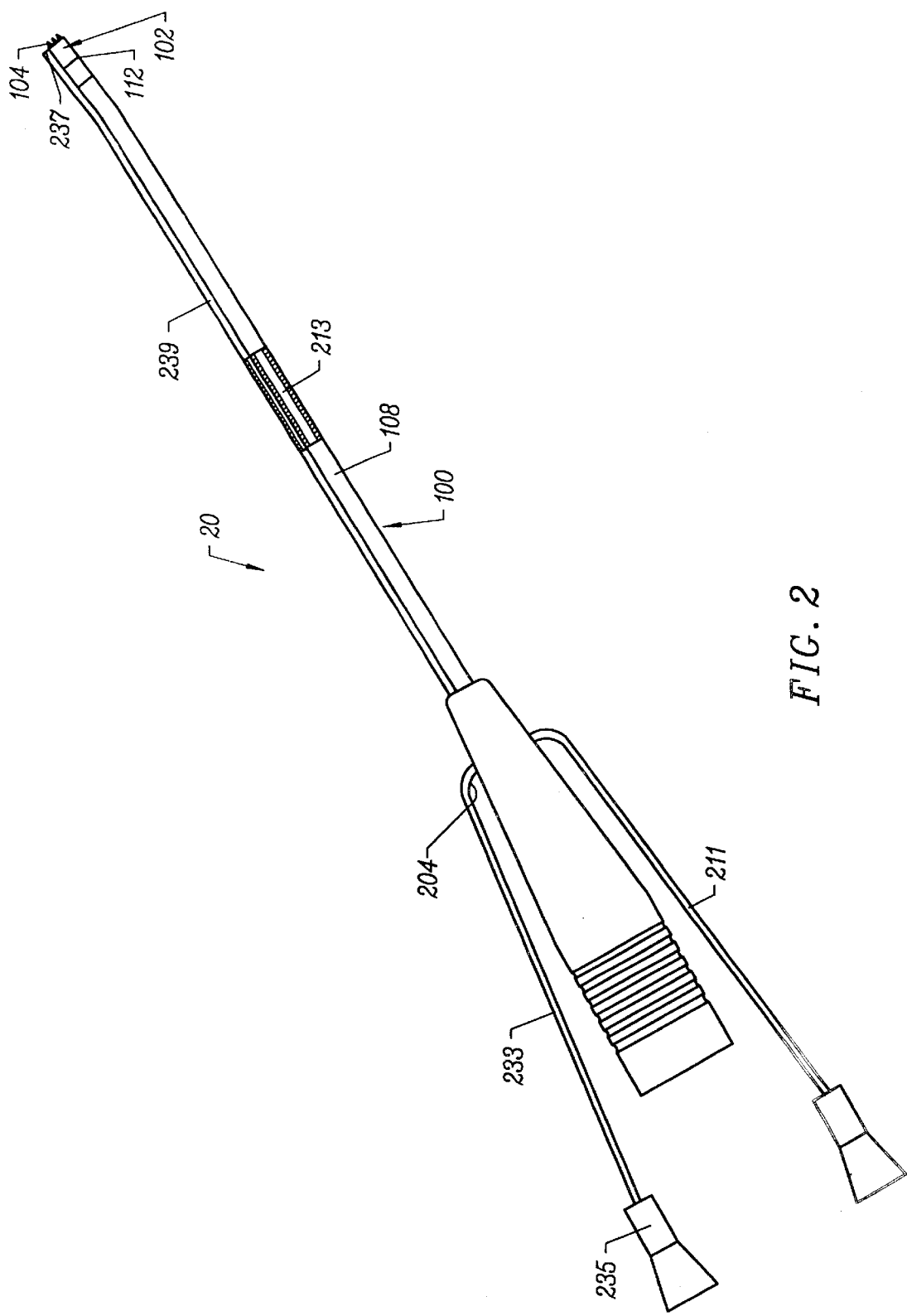
FIG. 2 is a side view of an electrosurgical probe according to the present invention.

FIGS. 2–5 illustrate an exemplary electrosurgical probe 20 constructed according to the principles of the present invention. As shown in FIG. 2, probe 20 generally includes an elongated shaft 100 which may be flexible or rigid, a handle 204 coupled to the proximal end of shaft 100 and an electrode support member 102 coupled to the distal end of shaft 100. Shaft 100 preferably comprises a plastic material that is easily molded into the shape shown in FIG. 2. In an alternative embodiment (not shown), shaft 100 comprises an electrically conducting material, usually metal, which is selected from the group comprising tungsten, stainless steel alloys, platinum or its alloys, titanium or its alloys, molybdenum or its alloys, and nickel or its alloys. In this embodiment, shaft 100 includes an electrically insulating jacket 108, which is typically formed as one or more electrically insulating sheaths or coatings, such as polytetrafluoroethylene, polyimide, and the like. The provision of the electrically insulating jacket over the shaft prevents direct electrical contact between these metal elements and any adjacent body structure or the surgeon. Such direct electrical contact between a body structure (e.g., tendon) and an exposed electrode could result in unwanted heating and necrosis of the structure at the point of contact causing necrosis.

Handle 204 typically comprises a plastic material that is easily molded into a suitable shape for handling by the surgeon. Handle 204 defines an inner cavity (not shown) that houses the electrical connections 250 (FIG. 5), and provides a suitable interface for connection to an electrical connecting cable 22 (see FIG. 1). Electrode support member 102 extends from the distal end of shaft 100 (usually about 1 to 20 mm), and provides support for a plurality of electrically isolated electrode terminals 104 (see FIG. 4). As shown in FIG. 2, a fluid tube 233 extends through an opening in handle 204, and includes a connector 235 for connection to a fluid supply source, for supplying electrically conductive fluid to the target site. Fluid tube 233 is coupled to a distal fluid tube 239 that extends along the outer surface of shaft 100 to an opening 237 at the distal end of the probe 20, as discussed in detail below. Of course, the invention is not limited to this configuration. For example, fluid tube 233 may extend through a single lumen (not shown) in shaft 100, or it may be coupled to a plurality of lumens (also not shown) that extend through shaft 100 to a plurality of openings at its distal end. Probe 20 may also include a valve 17 (FIG. 1) or equivalent structure for controlling the flow rate of the electrically conducting fluid to the target site.

Figure 3:
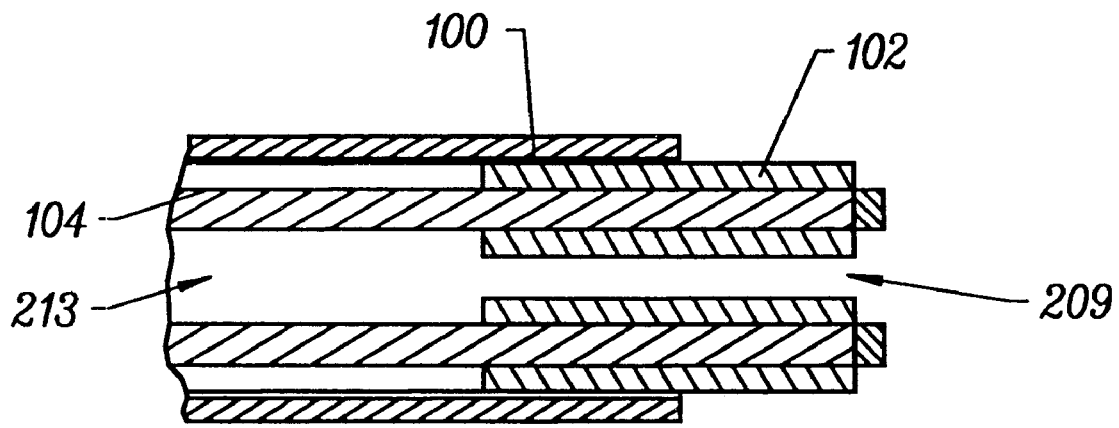
FIG. 3 is a cross-sectional view of a distal portion of the probe of FIG. 2.
Figure 4:
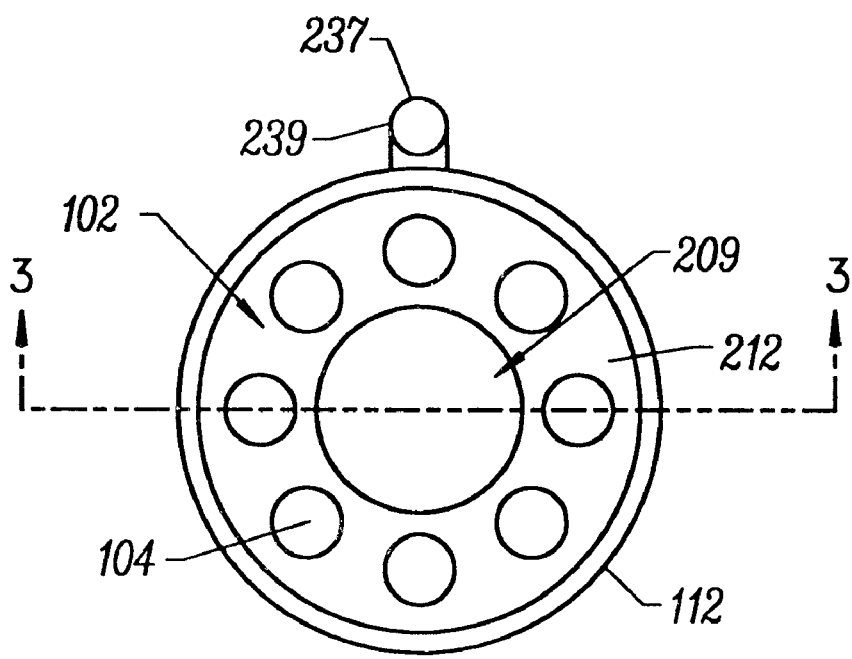
FIG. 4 is an end view of the probe of FIG. 2, illustrating an array of active electrode terminals.

As shown in FIGS. 3 and 4, electrode support member 102 has a substantially planar tissue treatment surface 212 and comprises a suitable insulating material (e.g., ceramic or glass material, such as alumina, zirconia and the like) which could be formed at the time of manufacture in a flat, hemispherical or other shape according to the requirements of a particular procedure. The preferred support member material is alumina, available from Kyocera Industrial Ceramics Corporation, Elkgrove, Ill., because of its high thermal conductivity, good electrically insulative properties, high flexural modulus, resistance to carbon tracking, biocompatibility, and high melting point. The support member 102 is adhesively joined to a tubular support member (not shown) that extends most or all of the distance between support member 102 and the proximal end of probe 20. The tubular member preferably comprises an electrically insulating material, such as an epoxy or silicone-based material.

In a preferred construction technique, electrode terminals 104 extend through pre-formed openings in the support member 102 so that they protrude above tissue treatment surface 212 by the desired distance. The electrodes are then bonded to the tissue treatment surface 212 of support member 102, typically by an inorganic sealing material. The sealing material is selected to provide effective electrical insulation, and good adhesion to both the alumina member 102 and the platinum or titanium electrode terminals 104. The sealing material additionally should have a compatible thermal expansion coefficient and a melting point well below that of platinum or titanium and alumina or zirconia, typically being a glass or glass ceramic, In the embodiment shown in FIGS. 2–5, probe 20 includes a return electrode 112 for completing the current path between electrode terminals 104 and a high frequency power supply 28 (see FIG. 1). As shown, return electrode 112 preferably comprises an annular conductive band coupled to the distal end of shaft 100 slightly proximal to tissue treatment surface 212 of electrode support member 102, typically about 0.5 to 10 mm and more preferably about 1 to 10 mm. Return electrode 112 is coupled to a connector 258 that extends to the proximal end of probe 10, where it is suitably connected to power supply 10 (FIG. 1).

As shown in FIG. 2, return electrode 112 is not directly connected to electrode terminals 104. To complete this current path so that electrode terminals 104 are electrically connected to return electrode 112, electrically conducting fluid (e.g., isotonic saline) is caused to flow therebetween. In the representative embodiment, the electrically conducting fluid is delivered through an external fluid tube 239 to opening 237, as described above. Alternatively, the fluid may be delivered by a fluid delivery element (not shown) that is separate from probe 20. In some microendoscopic discectomy procedures, for example, the trocar cannula may be flooded with isotonic saline and the probe 20 will be introduced into this flooded cavity. Electrically conducting fluid will be continually resupplied with a separate instrument to maintain the conduction path between return electrode 112 and electrode terminals 104.

In alternative embodiments, the fluid path may be formed in probe 20 by, for example, an inner lumen or an annular gap between the return electrode and a tubular support member within shaft 100 (not shown). This annular gap may be formed near the perimeter of the shaft 100 such that the electrically conducting fluid tends to flow radially inward towards the target site, or it may be formed towards the center of shaft 100 so that the fluid flows radially outward. In both of these embodiments, a fluid source (e.g., a bag of fluid elevated above the surgical site or having a pumping device), is coupled to probe 90 via a fluid supply tube (not shown) that may or may not have a controllable valve. A more complete description of an electrosurgical probe incorporating one or more fluid lumen(s) can be found in parent application U.S. Pat. No. 5,697,281, filed on Jun. 7, 1995, the complete disclosure of which has previously been incorporated herein by reference.

Referring to FIG. 4, the electrically isolated electrode terminals 104 are spaced apart over tissue treatment surface 212 of electrode support member 102. The tissue treatment surface and individual electrode terminals 104 will usually have dimensions within the ranges set forth above. In the representative embodiment, the tissue treatment surface 212 has a circular cross-sectional shape with a diameter in the range of about 1 mm to 30 mm, usually about 2 to 20 mm. The individual electrode terminals 104 preferably extend outward from tissue treatment surface 212 by a distance of about 0.1 to 8 mm, usually about 0.2 to 4 mm. Applicant has found that this configuration increases the high electric field intensities and associated current densities around electrode terminals 104 to facilitate the ablation of tissue as described in detail above.

In the embodiment of FIGS. 2–5, the probe includes a single, larger opening 209 in the center of tissue treatment surface 212, and a plurality of electrode terminals (e.g., about 3–15) around the perimeter of surface 212 (see FIG. 3). Alternatively, the probe may include a single, annular, or partially annular, electrode terminal at the perimeter of the tissue treatment surface. The central opening 209 is coupled to a suction or aspiration lumen 213 (see FIG. 2) within shaft 100 and a suction tube 211 (FIG. 2) for aspirating tissue, fluids and/or gases from the target site. In this embodiment, the electrically conductive fluid generally flows from opening 237 of fluid tube 239 radially inward past electrode terminals 104 and then back through the central opening 209 of support member 102. Aspirating the electrically conductive fluid during surgery allows the surgeon to see the target site, and it prevents the fluid from flowing into the patient's body, e.g., into the spine, the abdomen or the thoracic cavity. This aspiration should be controlled, however, so that the conductive fluid maintains a conductive path between the active electrode terminal(s) and the return electrode.

Of course, it will be recognized that the distal tip of probe may have a variety of different configurations. For example, the probe may include a plurality of openings 209 around the outer perimeter of tissue treatment surface 212 (this embodiment not shown in the drawings). In this embodiment, the electrode terminals 104 extend from the center of tissue treatment surface 212 radially inward from openings 209. The openings are suitably coupled to fluid tube 233 for delivering electrically conductive fluid to the target site, and aspiration lumen 213 for aspirating the fluid after it has completed the conductive path between the return electrode 112 and the electrode terminals 104.

Figure 6:
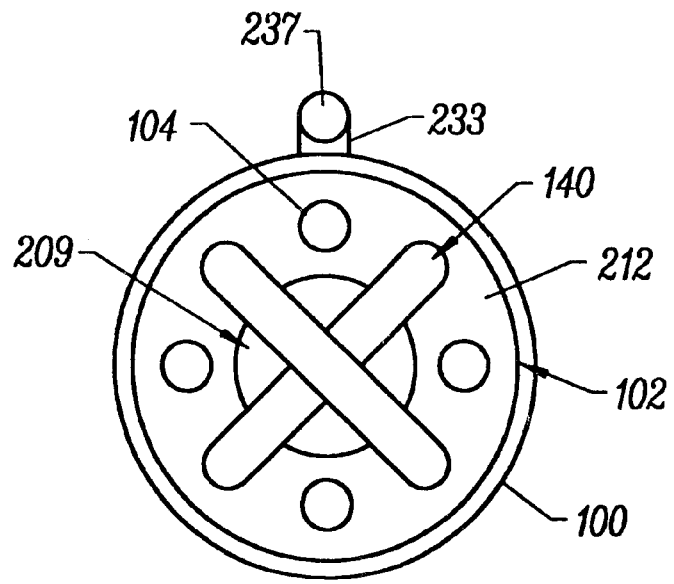
FIGS. 6–10 are end views of alternative embodiments of the probe of FIG. 2, incorporating aspiration electrode(s)

In some embodiments, the probe 20 will also include one or more aspiration electrode(s) coupled to the aspiration lumen for inhibiting clogging during aspiration of tissue fragments from the surgical site. As shown in FIG. 6, one or more of the active electrode terminals 104 may comprise loop electrodes 140 that extend across distal opening 209 of the suction lumen within shaft 100. In the representative embodiment, two of the electrode terminals 104 comprise loop electrodes 140 that cross over the distal opening 209. Of course, it will be recognized that a variety of different configurations are possible, such as a single loop electrode, or multiple loop electrodes having different configurations than shown. In addition, the electrodes may have shapes other than loops, such as the coiled configurations shown in FIGS. 6 and 7. Alternatively, the electrodes may be formed within suction lumen proximal to the distal opening 209, as shown in FIG. 8. The main function of loop electrodes 140 is to ablate portions of tissue that are drawn into the suction lumen to prevent clogging of the lumen.

Loop electrodes 140 are electrically isolated from the other electrode terminals 104, which can be referred to hereinafter as the ablation electrodes 104. Loop electrodes 140 may or may not be electrically isolated from each other. Loop electrodes 140 will usually extend only about 0.05 to 4 mm, preferably about 0.1 to 1 mm from the tissue treatment surface of electrode support member 104.

Figure 7:
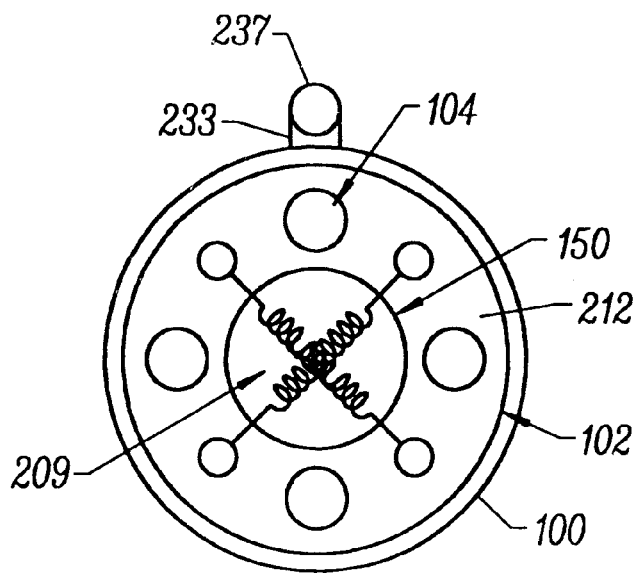
Figure 8:
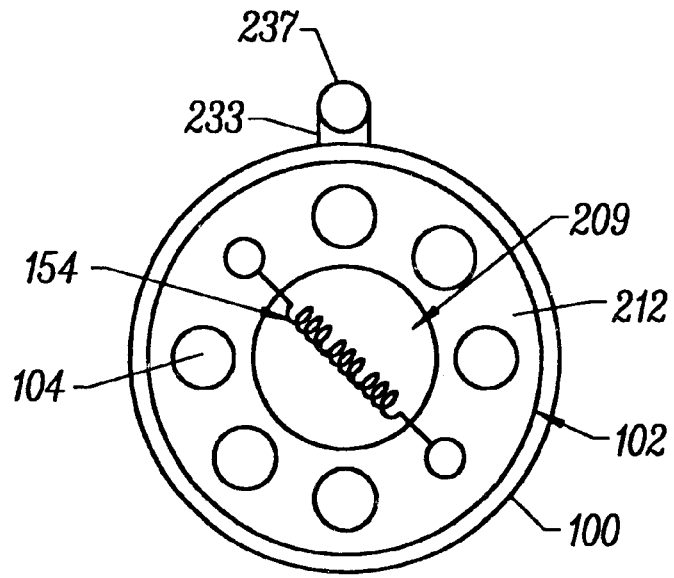

Referring now to FIGS. 7 and 8, alternative embodiments for aspiration electrodes will now be described. As shown in FIG. 7, the aspiration electrodes may comprise a pair of coiled electrodes 150 that extend across distal opening 209 of the suction lumen. The larger surface area of the coiled electrodes 150 usually increases the effectiveness of the electrodes 150 on tissue fragments passing through opening 209. In FIG. 8, the aspiration electrode comprises a single coiled electrode 152 passing across the distal opening 209 of suction lumen. This single electrode 152 may be sufficient to inhibit clogging of the suction lumen. Alternatively, the aspiration electrodes may be positioned within the suction lumen proximal to the distal opening 209. Preferably, these electrodes are close to opening 209 so that tissue does not clog the opening 209 before it reaches electrodes 154. In this embodiment, a separate return electrode 156 may be provided within the suction lumen to confine the electric currents therein.

Figure 10:
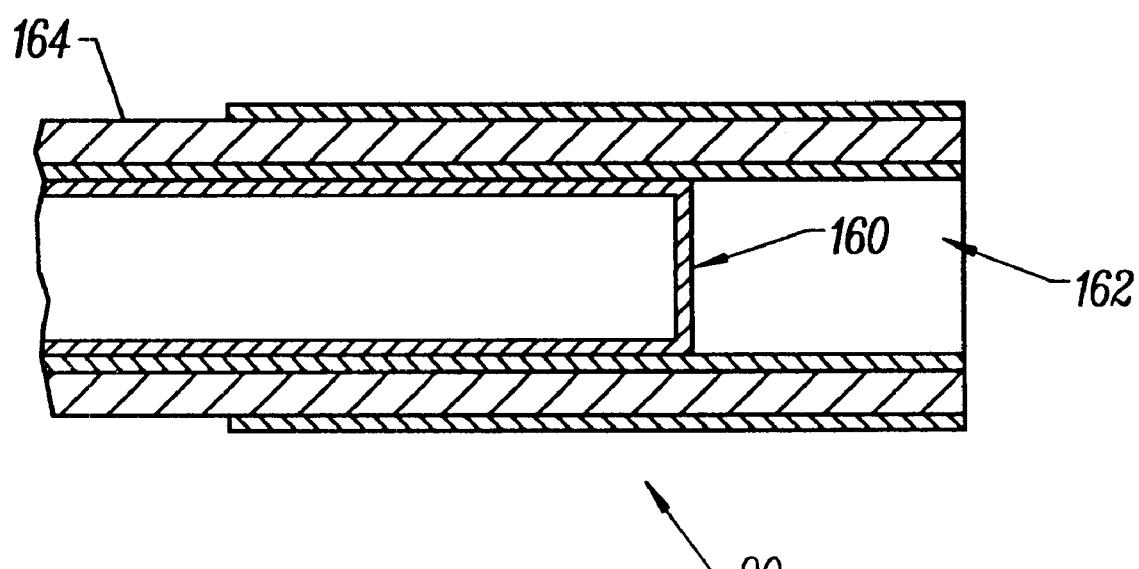
Figure 12:
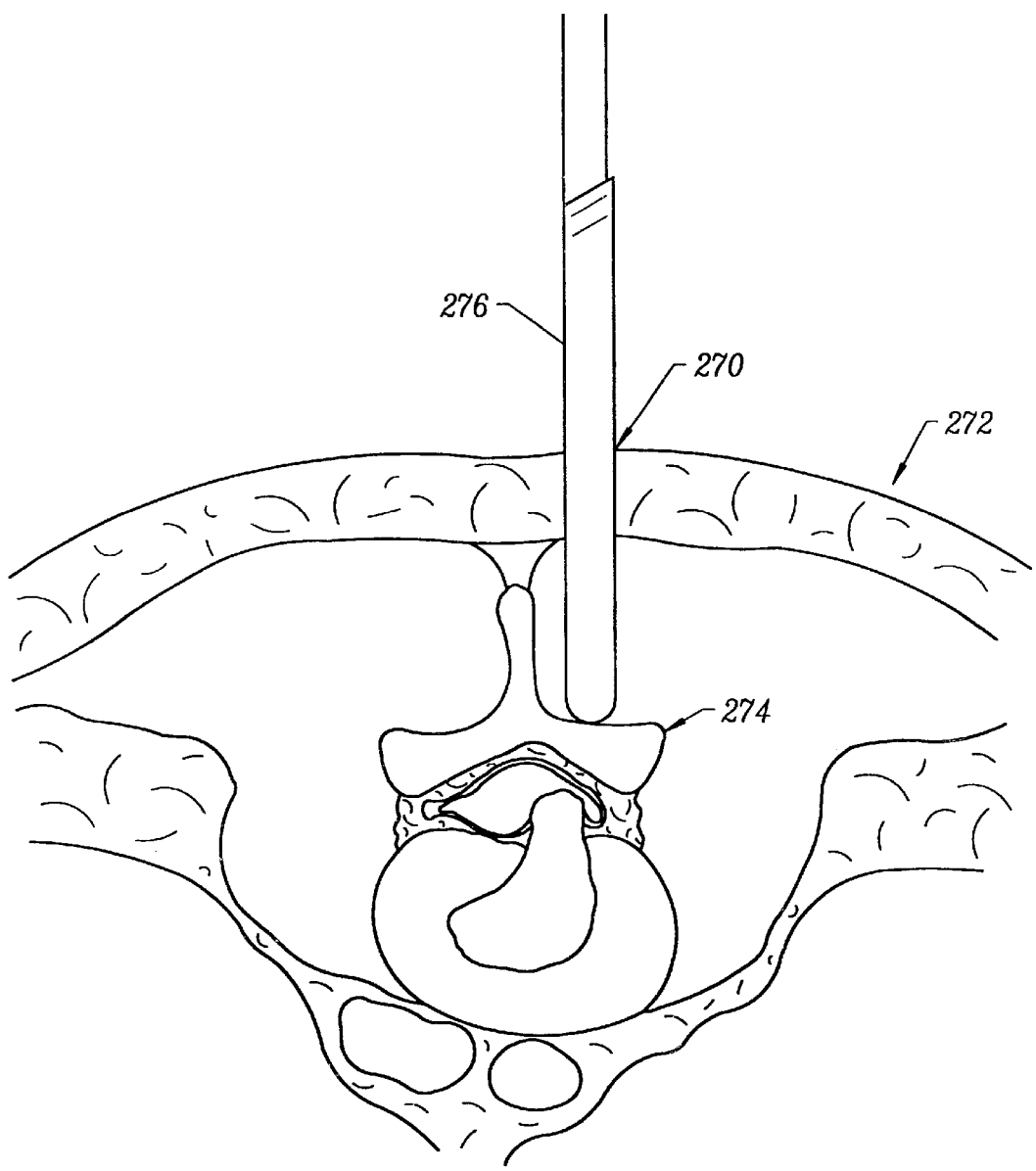
FIGS. 12–15 illustrate a method of performing a microendoscopic discectomy according to the principles of the present invention.

Referring to FIG. 10, another embodiment of the present invention incorporates an aspiration electrode 160 within the aspiration lumen 162 of the probe. As shown, the electrode 160 is positioned just proximal of distal opening 209 so that the tissue fragments are ablated as they enter lumen 162. In the representation embodiment, the aspiration electrode 160 comprises a loop electrode that stretches across the aspiration lumen 162. However, it will be recognized that many other configurations are possible. In this embodiment, the return electrode 164 is located outside of the probe as in the previously embodiments. Alternatively, the return electrode (s) may be located within the aspiration lumen 162 with the aspiration electrode 160. For example, the inner insulating coating 163 may be exposed at portions within the lumen 162 to provide a conductive path between this exposed portion of return electrode 164 and the aspiration electrode 160. The latter embodiment has the advantage of confining the electric currents to within the aspiration lumen. In addition, in dry fields in which the conductive fluid is delivered to the target site, it is usually easier to maintain a conductive fluid path between the active and return electrodes in the latter embodiment because the conductive fluid is aspirated through the aspiration lumen 162 along with the tissue fragments.

Figure 9:
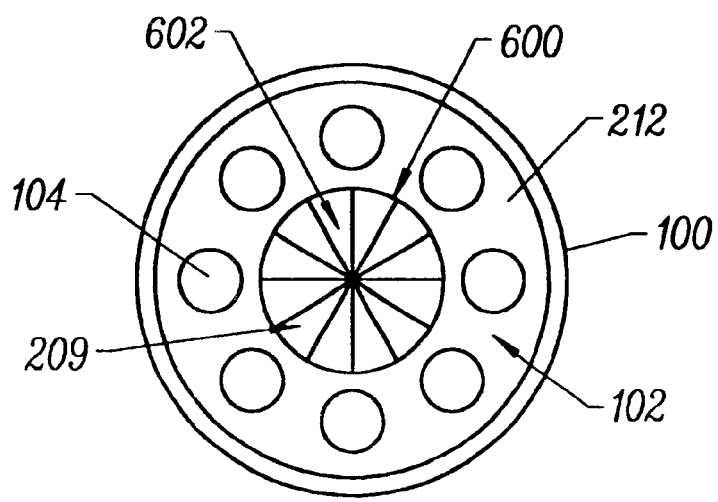

Referring to FIG. 9, another embodiment of the present invention incorporates a wire mesh electrode 600 extending across the distal portion of aspiration lumen 162. As shown, mesh electrode 600 includes a plurality of openings 602 to allow fluids and tissue fragments to flow through into aspiration lumen 162. The size of the openings 602 will vary depending on a variety of factors. The mesh electrode may be coupled to the distal or proximal surfaces of ceramic support member 102. Wire mesh electrode 600 comprises a conductive material, such as titanium, tantalum, steel, stainless steel, tungsten, copper, gold or the like. In the representative embodiment, wire mesh electrode 600 comprises a different material having a different electric potential than the active electrode terminal(s) 104. Preferably, mesh electrode 600 comprises steel and electrode terminal(s) comprises tungsten. Applicant has found that a slight variance in the electrochemical potential of mesh electrode 600 and electrode terminal(s) 104 improves the performance of the device. Of course, it will be recognized that the mesh electrode may be electrically insulated from active electrode terminal(s) as in previous embodiments, Referring now to FIGS. 11A–11C, an alternative embodiment incorporating a metal screen 610 is illustrated. As shown, metal screen 610 has a plurality of peripheral openings 612 for receiving electrode terminals 104, and a plurality of inner openings 614 for allowing aspiration of fluid and tissue through opening 609 of the aspiration lumen. As shown, screen 610 is press fitted over electrode terminals 104 and then adhered to shaft 100 of probe 20. Similar to the mesh electrode embodiment, metal screen 610 may comprise a variety of conductive metals, such as titanium, tantalum, steel, stainless steel, tungsten, copper, gold or the like. In the representative embodiment, metal screen 610 is coupled directly to, or integral with, active electrode terminal(s) 104. In this embodiment, the active electrode terminal(s) 104 and the metal screen 610 are electrically coupled to each other.

Figure 32A:
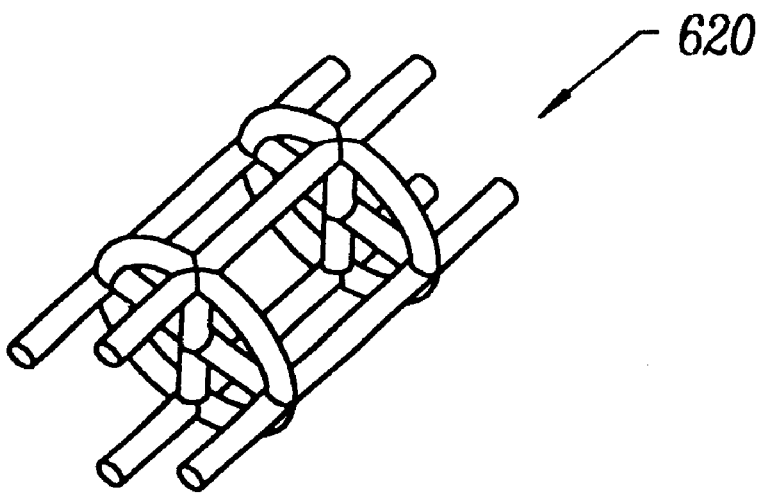
FIGS. 32A and 32B illustrate an alternative cage aspiration electrode for use with the electrosurgical probes shown in FIGS. 2–11.
Figure 32B:
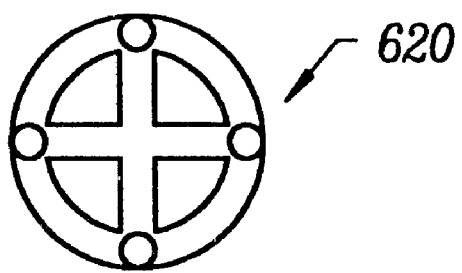
Figure 33A:
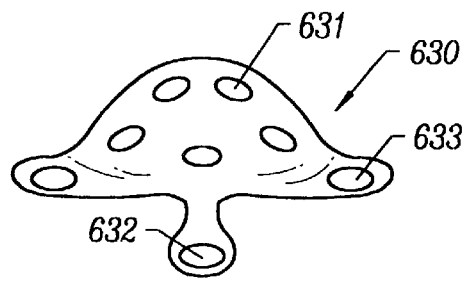
FIGS. 33A–33C illustrate an alternative dome shaped aspiration electrode for use with the electrosurgical probes of FIGS. 2–11.
Figure 33B:
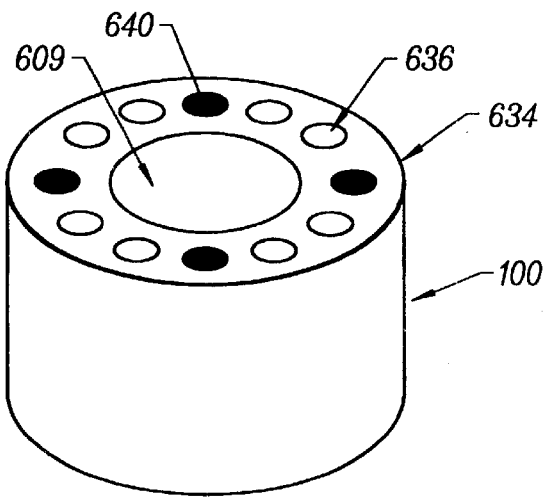
Figure 33C:
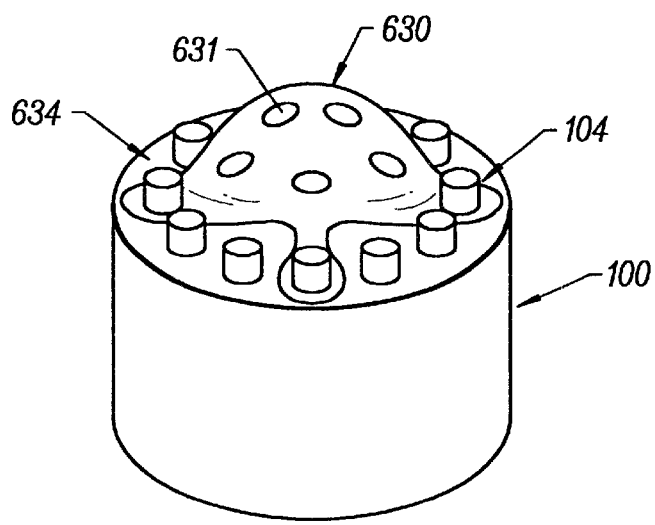

FIGS. 32 and 33 illustrate alternative embodiments of the mesh and screen aspiration electrodes. As shown in FIG. 32A and 32B, the probe may include a conductive cage electrode 620 that extends into the aspiration lumen 162 (not shown) to increase the effect of the electrode on aspirated tissue. FIGS. 33A–33C illustrate a dome-shaped screen electrode 630 that includes one or more anchors 632 (four in the representative embodiment) for attaching the screen electrode 630 to a conductive spacer 634. Screen electrode 630 includes a plurality of holes 631 for allowing fluid and tissue fragments to pass therethrough to aspiration lumen 162. Screen electrode 630 is sized to fit within opening 609 of aspiration lumen 162 except for the anchors 632 which include holes 633 for receiving electrode terminals 104. Spacer 634 includes peripheral holes 636 for receiving electrode terminals 104 and a central hole 638 aligned with suction lumen 162. Spacer 634 may further include insulated holes 640 for electrically isolating screen electrode 630 from electrode terminals 104. As shown in FIG. 33C, dome-shaped screen electrode 630 preferably extends distally from the probe shaft 100 about the same distance as the electrode terminals 104. Applicant has found that this configuration enhances the ablation rate for tissue adjacent to electrode terminals 104, while still maintaining the ability to ablate aspirated tissue fragments passing through screen 630.

Figure 5:
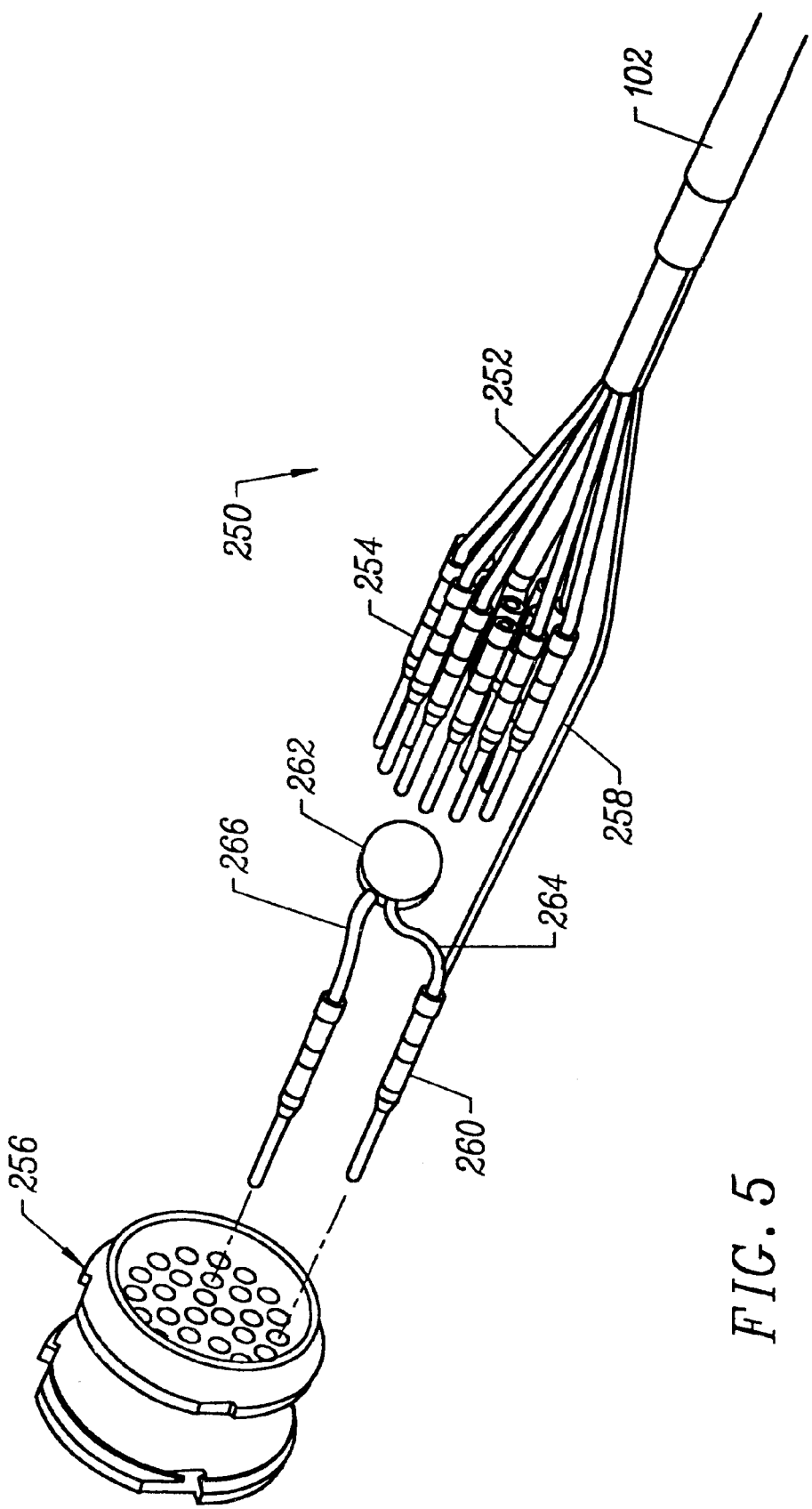
FIG. 5 is an exploded view of the electrical connections within the probe of FIG. 2.

FIG. 5 illustrates the electrical connections 250 within handle 204 for coupling electrode terminals 104 and return electrode 112 to the power supply 28. As shown, a plurality of wires 252 extend through shaft 100 to couple terminals 104 to a plurality of pins 254, which are plugged into a connector block 256 for coupling to a connecting cable 22 (FIG. 1). Similarly, return electrode 112 is coupled to connector block 256 via a wire 258 and a plug 260.

In some embodiments of the present invention, the probe 20 further includes an identification element that is characteristic of the particular electrode assembly so that the same power supply 28 can be used for different electrosurgical operations. In one embodiment, for example, the probe 20 includes a voltage reduction element or a voltage reduction circuit for reducing the voltage applied between the electrode terminals 104 and the return electrode 112. The voltage reduction element serves to reduce the voltage applied by the power supply so that the voltage between the electrode terminals and the return electrode is low enough to avoid excessive power dissipation into the electrically conducting medium and/or ablation of the soft tissue at the target site. The voltage reduction element primarily allows the electrosurgical probe 20 to be compatible with other ArthroCare generators that are adapted to apply higher voltages for ablation or vaporization of tissue. For contraction of tissue, for example, the voltage reduction element will serve to reduce a voltage of about 100 to 135 volts rms (which is a setting of 1 on the ArthroCare Model 970 and 980 (i.e., 2000) Generators) to about 45 to 60 volts rms, which is a suitable voltage for contraction of tissue without ablation (e.g., molecular dissociation) of the tissue.

Of course, for some procedures in endoscopic spine surgery, the probe will typically not require a voltage reduction element. Alternatively, the probe may include a voltage increasing element or circuit, if desired.

In the representative embodiment, the voltage reduction element is a dropping capacitor 262 which has first leg 264 coupled to the return electrode wire 258 and a second leg 266 coupled to connector block 256. Of course, the capacitor may be located in other places within the system, such as in, or distributed along the length of, the cable, the generator, the connector, etc. In addition, it will be recognized that other voltage reduction elements, such as diodes, transistors, inductors, resistors, capacitors or combinations thereof, may be used in conjunction with the present invention. For example, the probe 90 may include a coded resistor (not shown) that is constructed to lower the voltage applied between return electrode 112 and electrode terminals 104 to a suitable level for contraction of tissue. In addition, electrical circuits may be employed for this purpose.

Alternatively or additionally, the cable 22 that couples the power supply 10 to the probe 90 may be used as a voltage reduction element. The cable has an inherent capacitance that can be used to reduce the power supply voltage if the cable is placed into the electrical circuit between the power supply, the electrode terminals and the return electrode. In this embodiment, the cable 22 may be used alone, or in combination with one of the voltage reduction elements discussed above, e.g., a capacitor.

In some embodiments, the probe 20 will further include a switch (not shown) or other input that allows the surgeon to couple and decouple the identification element to the rest of the electronics in the probe 20. For example, if the surgeon would like to use the same probe for ablation of tissue and contraction of tissue in the same procedure, this can be accomplished by manipulating the switch. Thus, for ablation of tissue, the surgeon will decouple the voltage reduction element from the electronics so that the full voltage applied by the power source is applied to the electrodes on the probe. When the surgeon desires to reduce the voltage to a suitable level for contraction of tissue, he/she couples the voltage reduction element to the electronics to reduce the Voltage applied by the power supply to the electrode terminals.

Further, it should be noted that the present invention can be used with a power supply that is adapted to apply a voltage within the selected range for treatment of tissue. In this embodiment, a voltage reduction element or circuitry may not be desired.

Figure 13:
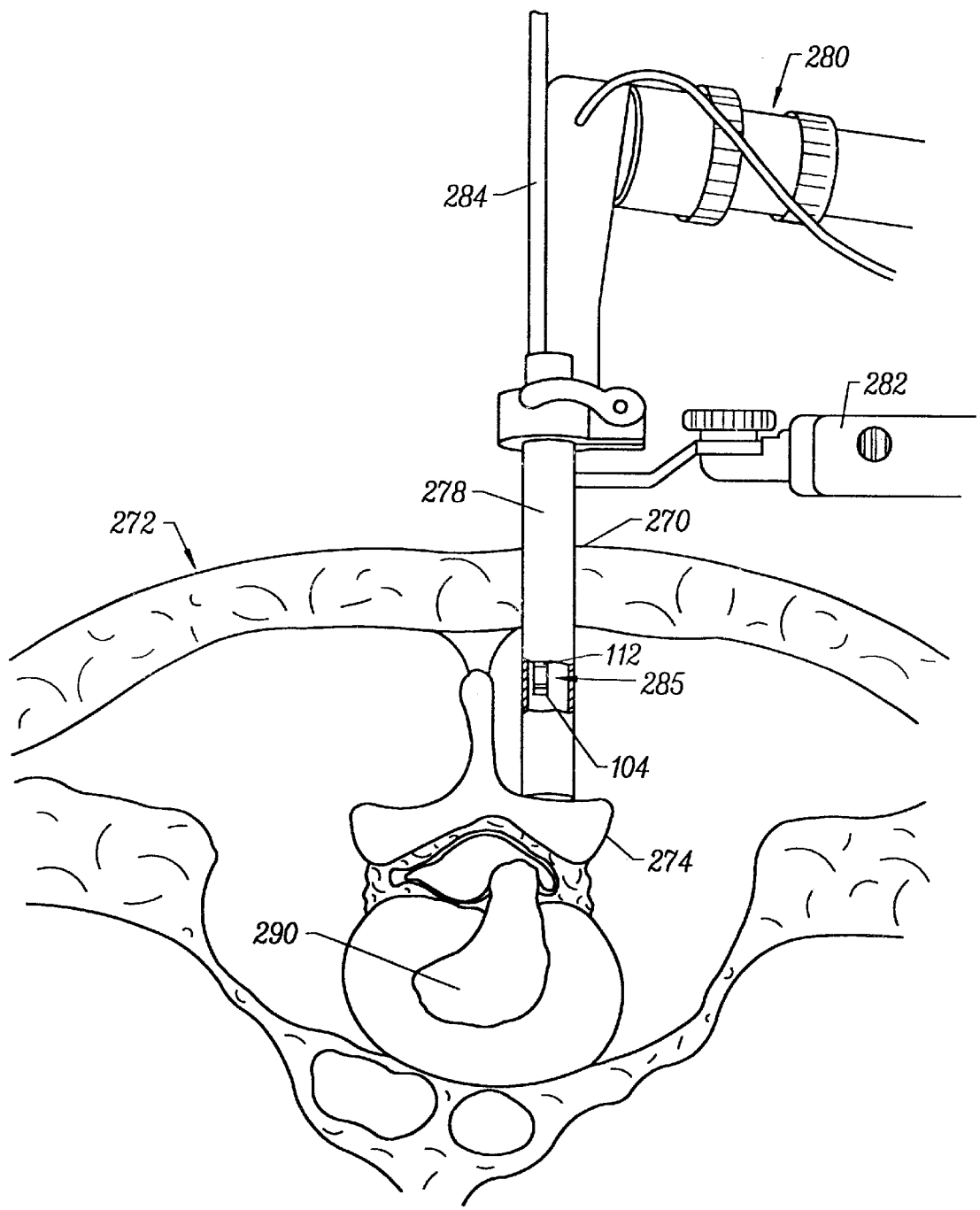

The present invention is particularly useful in microendoscopic discectomy procedures, e.g., for decompressing a nerve root with a lumbar discectomy. As shown in FIGS. 12–15, a percutaneous penetration 270 is made in the patients' back 272 so that the superior lamina 274 can be accessed. Typically, a small needle (not shown) is used initially to localize the disc space level, and a guidewire (not shown) is inserted and advanced under lateral fluoroscopy to the inferior edge of the lamina 274. Sequential cannulated dilators 276 are inserted over the guide wire and each other to provide a hole from the incision 220 to the lamina 274. The first dilator may be used to "palpate" the lamina 274, assuring proper location of its tip between the spinous process and facet complex just above the inferior edge of the lamina 274. As shown in FIG. 13, a tubular retractor 278 is then passed over the largest dilator down to the lamina 274. The dilators 276 are removed, establishing an operating corridor within the tubular retractor 278.

As shown in FIG. 13, an endoscope 280 is then inserted into the tubular retractor 278 and a ring clamp 282 is used to secure the endoscope 280. Typically, the formation of the operating corridor within retractor 278 requires the removal of soft tissue, muscle or other types of tissue that were forced into this corridor as the dilators 276 and retractor 278 were advanced down to the lamina 274. This tissue is usually removed with mechanical instruments, such as pituitary rongeurs, curettes, graspers, cutters, drills, microdebriders and the like. Unfortunately, these mechanical instruments greatly lengthen and increase the complexity of the procedure. In addition, these instruments sever blood vessels within this tissue, usually causing profuse bleeding that obstructs the surgeon's view of the target site.

According to the present invention, an electrosurgical probe or catheter 284 as described above is introduced into the operating corridor within the retractor 278 to remove the soft tissue, muscle and other obstructions from this corridor so that the surgeon can easily access and visualization the lamina 274. Once the surgeon has reached has introduced the probe 284, electrically conductive fluid 285 is delivered through tube 233 and opening 237 to the tissue (see FIG. 2). The fluid flows past the return electrode 112 to the electrode terminals 104 at the distal end of the shaft. The rate of fluid flow is controlled with valve 17 (FIG. 1) such that the zone between the tissue and electrode support 102 is constantly immersed in the fluid. The power supply 28 is then turned on and adjusted such that a high frequency voltage difference is applied between electrode terminals 104 and return-electrode 112. The electrically conductive fluid provides the conduction path (see current flux lines) between electrode terminals 104 and the return electrode 112.

The high frequency voltage is sufficient to convert the electrically conductive fluid (not shown) between the target tissue and electrode terminal(s) 104 into an ionized vapor layer or plasma (not shown). As a result of the applied voltage difference between electrode terminal(s) 104 and the target tissue (i.e., the voltage gradient across the plasma layer), charged particles in the plasma (viz., electrons) are accelerated towards the tissue. At sufficiently high voltage differences, these charged particles gain sufficient energy to cause dissociation of the molecular bonds within tissue structures. This molecular dissociation is accompanied by the volumetric removal (i.e., ablative sublimation) of tissue and the production of low molecular weight gases, such as oxygen, nitrogen, carbon dioxide, hydrogen and methane. The short range of the accelerated charged particles within the tissue confines the molecular dissociation process to the surface layer to minimize damage and necrosis to the underlying tissue.

During the process, the gases will be aspirated through opening 209 and suction tube 211 to a vacuum source. In addition, excess electrically conductive fluid, and other fluids (e.g., blood) will be aspirated from the operating corridor to facilitate the surgeon's view. During ablation of the tissue, the residual heat generated by the current flux lines (typically less than 150° C.), will usually be sufficient to coagulate any severed blood vessels at the site. If not, the surgeon may switch the power supply 28 into the coagulation mode by lowering the voltage to a level below the threshold for fluid vaporization, as discussed above. This simultaneous hemostasis results in less bleeding and facilitates the surgeon's ability to perform the procedure.

Another advantage of the present invention is the ability to precisely ablate soft tissue without causing necrosis or thermal damage to the underlying and surrounding tissues, nerves or bone. In addition, the voltage can be controlled so that the energy directed to the target site is insufficient to ablate the lamina 274 so that the surgeon can literally clean the tissue off the lamina 274, without ablating or otherwise effecting significant damage to the lamina.

Figure 14:
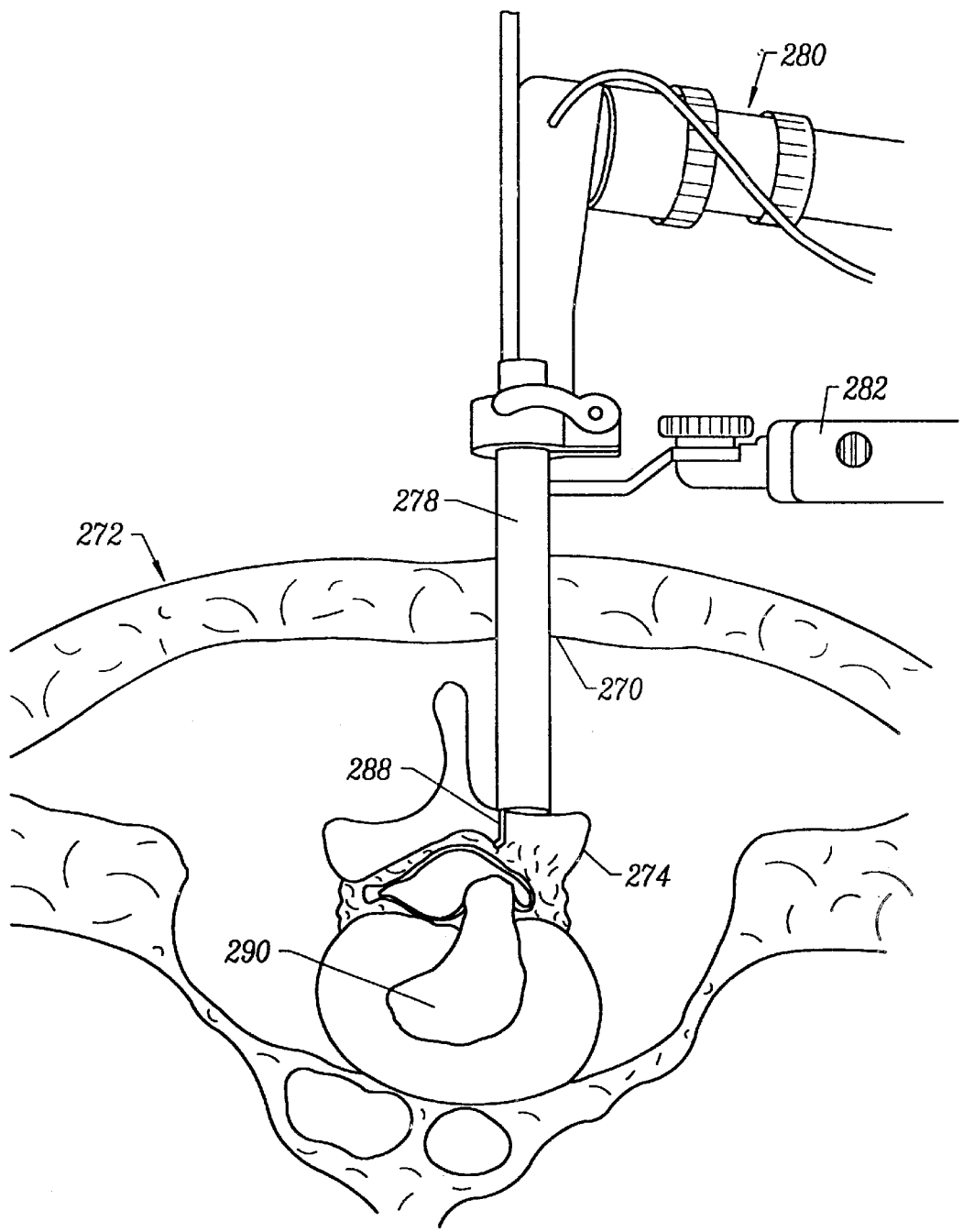
Figure 15:
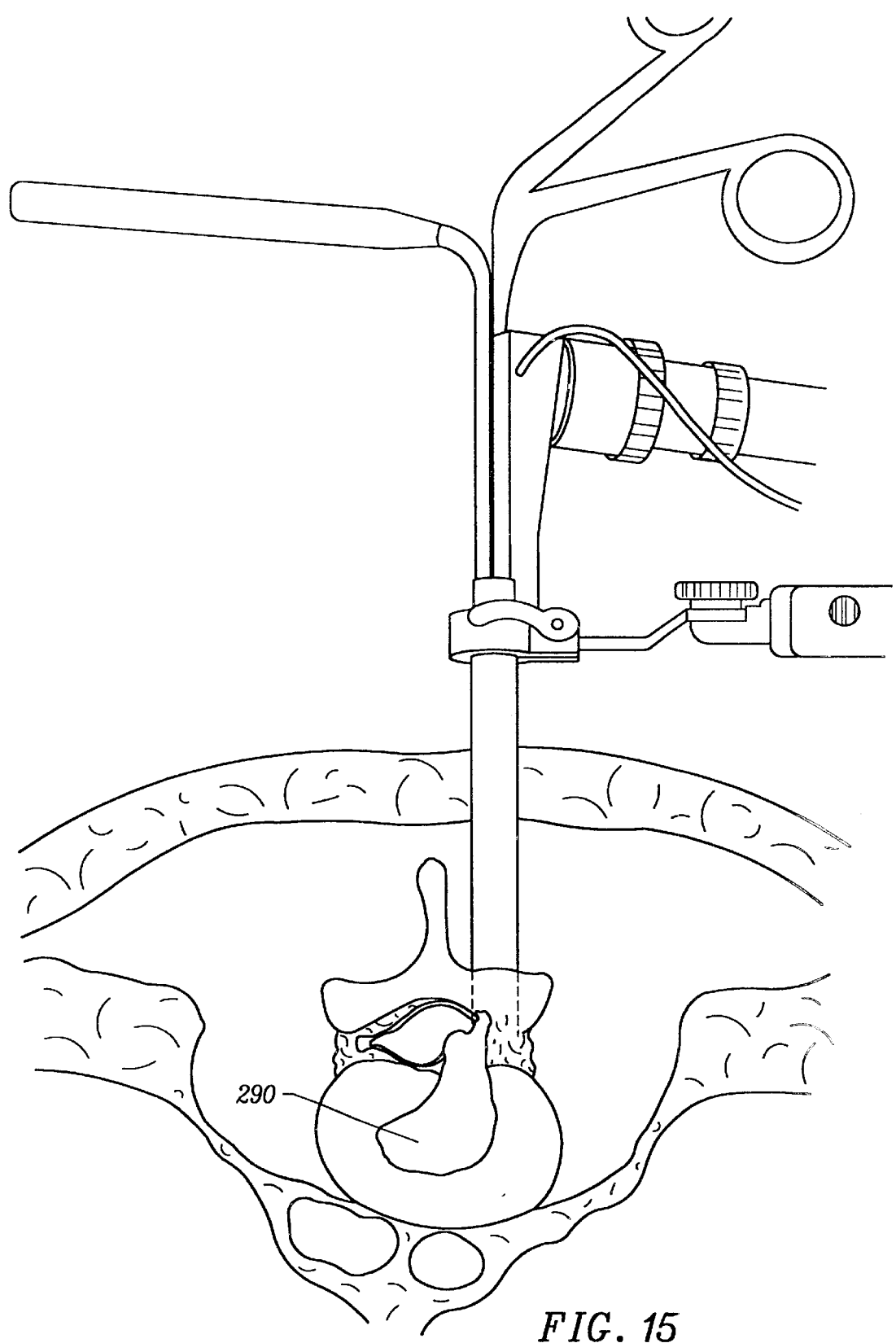

Referring now to FIGS. 14 and 15, once the operating corridor is sufficiently cleared, a laminotomy and medial facetectomy is accomplished either with conventional techniques (e.g., Kerrison punch or a high speed drill) or with the electrosurgical probe 284 as discussed above. After the nerve root is identified, medical retraction can be achieved with a retractor 288, or the present invention can be used to ablate with precision the disc. If necessary, epidural veins are cauterized either automatically or with the coagulation mode of the present invention. If an annulotomy is necessary, it can be accomplished with a microknife or the ablation mechanism of the present invention while protecting the nerve root with the retractor 288. The herniated disc 290 is then removed with a pituitary rongeur in a standard fashion, or once again through ablation as described above.

In another embodiment, the electrosurgical probe of the present invention can be used to ablate and/or contract soft tissue within the disc 290 to allow the annulus 292 to repair itself to prevent reoccurrence of this procedure. For tissue contraction, a sufficient voltage difference is applied between the electrode terminals 104 and the return electrode 112 to elevate the tissue temperature from normal body temperatures (e.g., 37° C.) to temperatures in the range of 45° C. to 90° C., preferably in the range from 60° C. to 70° C. This temperature elevation causes contraction of the collagen connective fibers within the disc tissue so that the disc 290 withdraws into the annulus 292.

In one method of tissue contraction according to the present invention, an electrically conductive fluid is delivered to the target site as described above, and heated to a sufficient temperature to induce contraction or shrinkage of the collagen fibers in the target tissue. The electrically conducting fluid is heated to a temperature sufficient to substantially irreversibly contract the collagen fibers, which generally requires a tissue temperature in the range of about 45° C. to 90° C., usually about 60° C. to 70° C. The fluid is heated by applying high frequency electrical energy to the electrode terminal(s) in contact with the electrically conducting fluid. The current emanating from the electrode terminal(s) 104 heats the fluid and generates a jet or plume of heated fluid, which is directed towards the target tissue. The heated fluid elevates the temperature of the collagen sufficiently to cause hydrothermal shrinkage of the collagen fibers. The return electrode 112 draws the electric current away from the tissue site to limit the depth of penetration of the current into the tissue, thereby inhibiting molecular dissociation and breakdown of the collagen tissue and minimizing or completely avoiding damage to surrounding and underlying tissue structures beyond the target tissue site. In an exemplary embodiment, the electrode terminal(s) 104 are held away from the tissue a sufficient distance such that the RF current does not pass into the tissue at all, but rather passes through the electrically conducting fluid back to the return electrode. In this embodiment, the primary mechanism for imparting energy to the tissue is the heated fluid, rather than the electric current.

In an alternative embodiment, the electrode terminal(s) 104 are brought into contact with, or close proximity to, the target tissue so that the electric current passes directly into the tissue to a selected depth. In this embodiment, the return electrode draws the electric current away from the tissue site to limit its depth of penetration into the tissue. Applicant has discovered that the depth of current penetration also can be varied with the electrosurgical system of the present invention by changing the frequency of the voltage applied to the electrode terminal and the return electrode. This is because the electrical impedance of tissue is known to decrease with increasing frequency due to the electrical properties of cell membranes which surround electrically conductive cellular fluid. At lower frequencies (e.g., less than 350 kHz), the higher tissue impedance, the presence of the return electrode and the electrode terminal configuration of the present invention (discussed in detail below) cause the current flux lines to penetrate less deeply resulting in a smaller depth of tissue heating. In an exemplary embodiment, an operating frequency of about 100 to 200 kHz is applied to the electrode terminal(s) to obtain shallow depths of collagen shrinkage (e.g., usually less than 1.5 mm and preferably less than 0.5 mm).

In another aspect of the invention, the size (e.g., diameter or principal dimension) of the electrode terminals employed for treating the tissue are selected according to the intended depth of tissue treatment. As described previously in copending patent application PCT International Application, U.S. National Phase Serial No. PCT/US94/05168, the depth of current penetration into tissue increases with increasing dimensions of an individual active electrode (assuming other factors remain constant, such as the frequency of the electric current, the return electrode configuration, etc.). The depth of current penetration (which refers to the depth at which the current density is sufficient to effect a change in the tissue, such as collagen shrinkage, irreversible necrosis, etc.) is on the order of the active electrode diameter for the bipolar configuration of the present invention and operating at a frequency of about 100 kHz to about 200 kHz. Accordingly, for applications requiring a smaller depth of current penetration, one or more electrode terminals of smaller dimensions would be selected. Conversely, for applications requiring a greater depth of current penetration, one or more electrode terminals of larger dimensions would be selected.

Figure 16:
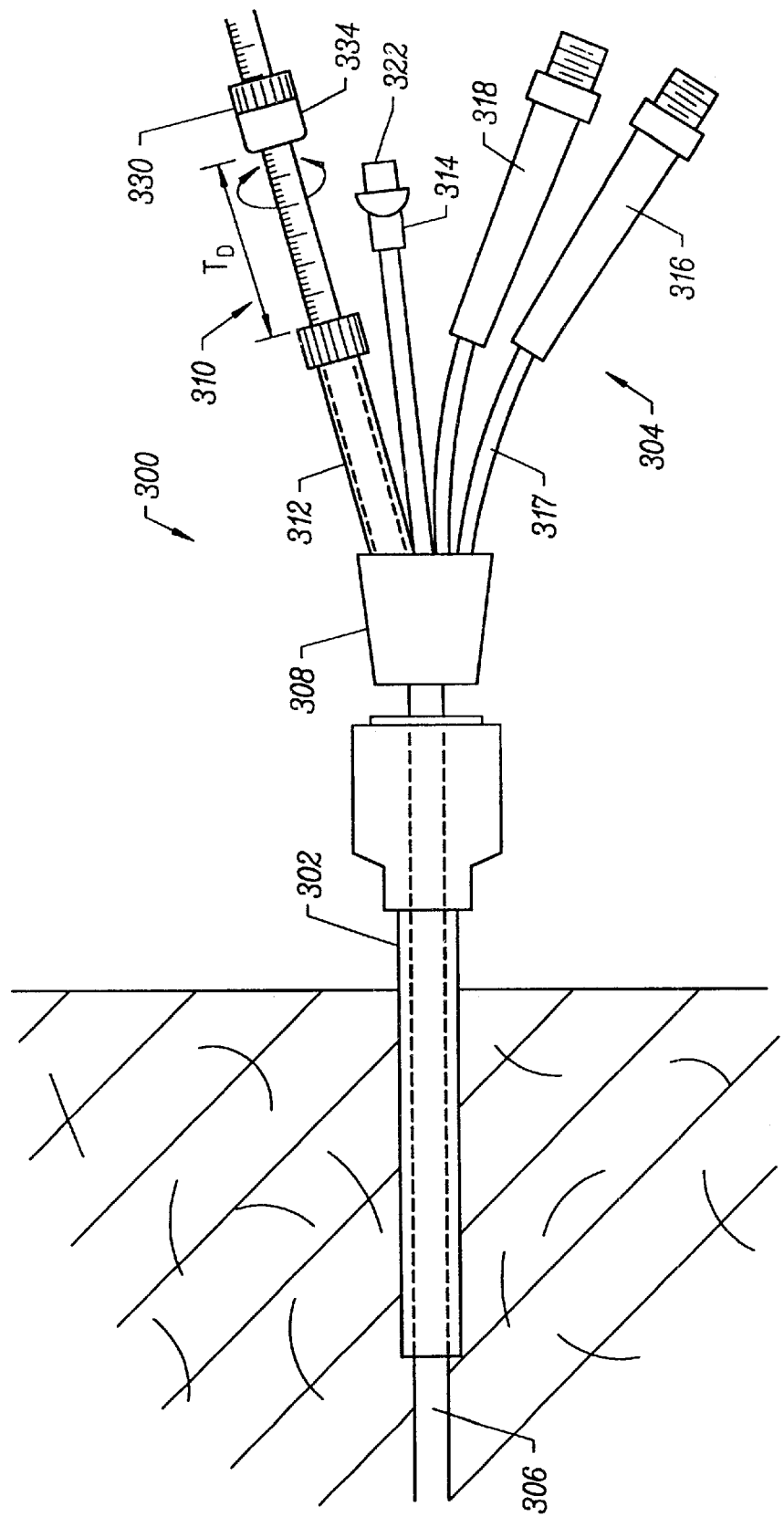
FIG. 16 is a schematic view of the proximal portion of another electrosurgical system for endoscopic spine surgery incorporating an electrosurgical instrument according to the present invention.
Figure 17:
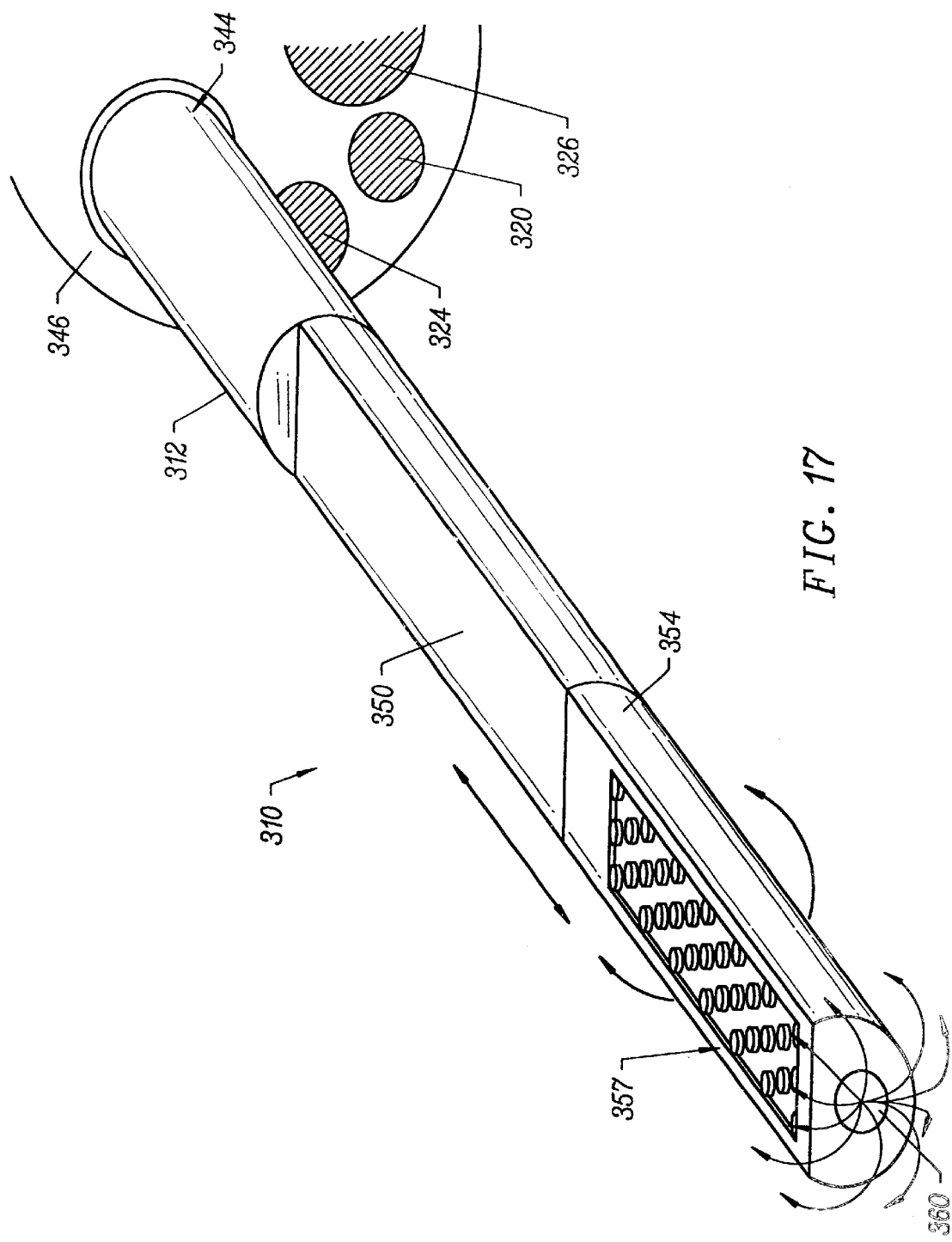
FIG. 17 is an enlarged view of a distal portion of the electrosurgical instrument of FIG. 16.
Figure 18:
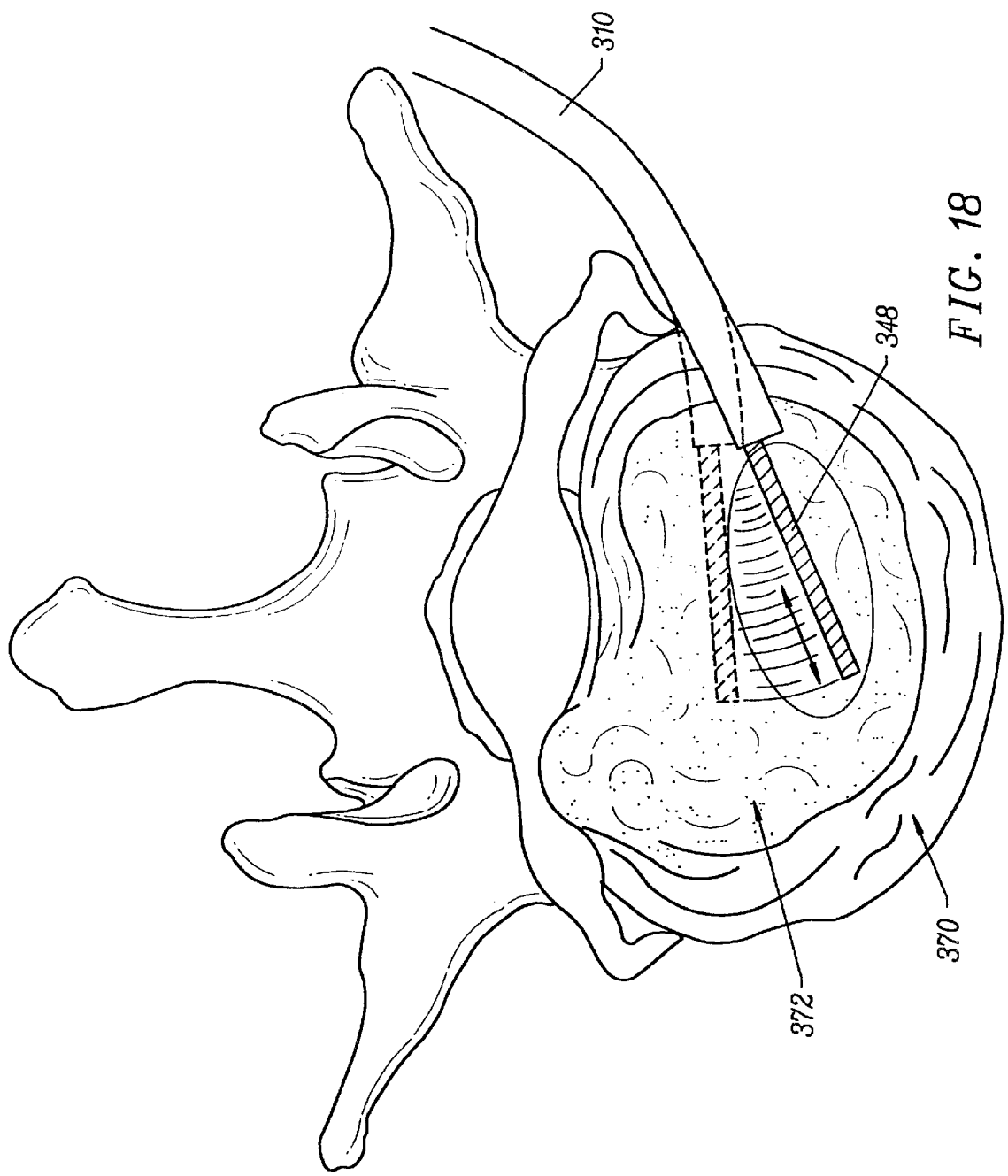
FIG. 18 illustrates a method of ablating a volume of tissue from the nucleus pulposis of a herniated disc with the electrosurgical system of FIG. 16.

FIGS. 16–18 illustrate an alternative electrosurgical system 300 specifically configured for endoscopic discectomy procedures, e.g., for treating extruded or non-extruded herniated discs. As shown in FIG. 16 system 300 includes a trocar cannula 302 for introducing a catheter assembly 304 through a percutaneous penetration in the patient to a target disc in the patient's spine. As discussed above, the catheter assembly 304 may be introduced through the thorax in a thoracoscopic procedure, through the abdomen in a laparascopic procedure, or directly through the patient's back. Catheter assembly 304 includes a catheter body 306 with a plurality of inner lumens (not shown) and a proximal hub 308 for receiving the various instruments that will pass through catheter body 306 to the target site. In this embodiment, assembly 304 includes an electrosurgical instrument 310 with a flexible shaft 312, an aspiration catheter 314, an endoscope 316 and an illumination fiber shaft 318 for viewing the target site. As shown in FIGS. 16 and 17, aspiration catheter 314 includes a distal port 320 and a proximal fitment 322 for attaching catheter 314 to a source of vacuum (not shown). Endoscope 316 will usually comprise a thin metal tube 317 with a lens 324 at the distal end, and an eyepiece (not shown) at the proximal end.

In the exemplary embodiment, electrosurgical instrument 310 includes a twist locking stop 330 at a proximal end of the shaft 312 for controlling the axial travel distance TD of the probe. As discussed in detail below, this configuration allows the surgeon to "set" the distance of ablation within the disc. In addition, instrument 310 includes a rotational indicator 334 for displaying the rotational position of the distal portion of instrument 310 to the surgeon. This rotational indicator 334 allows the surgeon to view this rotational position without relying on the endoscope 316 if visualization is difficult, or if an endoscope is not being used in the procedure.

Referring now to FIG. 17, a distal portion 340 of electrosurgical instrument 310 and catheter body 306 will now be described. As shown, instrument 310 comprises a relatively stiff, but deflectable electrically insulating support cannula 312 and a working end portion 348 movably coupled to cannula 312 for rotational and translational movement of working end 348. Working end 348 of electrosurgical instrument 310 can be rotated and translated to ablate and remove a volume of nucleus pulposus within a disc. Support cannula 312 extends through an internal lumen 344 and beyond the distal end 346 of catheter body 306. Alternatively, support cannula 312 may be separate from instrument 310, or even an integral part of catheter body 306. The distal portion of working end 348 includes an exposed return electrode 350 separated from an active electrode array 352 by an insulating support member 354, such as ceramic. In the representative embodiment, electrode array 352 is disposed on only one side of ceramic support member 354 so that its other side is insulating and thus atraumatic to tissue. Instrument 310 will also include a fluid lumen (not shown) having a distal port 360 in working end 348 for delivering electrically conductive fluid to the target site.

In use, trocar cannula 302 is introduced into a percutaneous penetration suitable for endoscopic delivery to the target disc in the spine. A trephine (not shown) or other conventional instrument may be used to form a channel from the trocar cannula 302 through the annulus fibrosis 370 and into the nucleus pulposis. Alternatively, the probe 310 may be used for this purpose, as discussed above. The working end 348 of instrument 310 is then advanced through cannula 302 a short distance (e.g., about 7 to 10 mm) into the nucleus pulposis 372, as shown in FIG. 18. Once the electrode array 352 is in position, electrically conductive fluid is delivered through distal port 360 to immerse the active electrode array 352 in the fluid. The vacuum source may also be activated to ensure a flow of conductive fluid between electrode array 352 past return electrode 350 to suction port 320, if necessary. In some embodiments, the mechanical stop 330 may then be set at the proximal end of the instrument 310 to limit the axial travel distance of working end 348. Preferably, this distance will be set to minimize (or completely eliminate) ablation of the surrounding annulus.

The probe is then energized by applying a high frequency voltage between the electrode array 352 and return electrode 350 so that electric current flows through the conductive fluid from the array 352 to the return electrode 350. The electric current causes vaporization of the fluid and ensuing molecular dissociation of the nucleus pulposus tissue as described in detail above. The instrument 310 may then be translated in an axial direction forwards and backwards to the preset limits. While still energized and translating, the working end 348 may also be rotated to ablate tissue surrounding the electrode array 352. In the representative embodiment, working end 348 will also include an inflatable gland 380 opposite electrode array 352 to allow deflection of working end 348 relative to support cannula 312. As shown in FIG. 18, working end 348 may be deflected to produce a large diameter bore within the nucleus pulposus, which assures close contact with tissue surfaces to be ablated. Alternatively, the entire catheter body 306, or the distal end of catheter body 306 may be deflected to increase the volume of nucleus pulposus removed.

After the desired volume of nucleus pulposis is removed (based on direct observation through port 324, or by kinesthetic feedback from movement of working end 348 of instrument 310), instrument 310 is withdrawn into catheter body 306 and the catheter body is removed from the patient. Typically, the preferred volume of removed tissue is about 0.2 to 5 cm$^3$.

Figure 19:
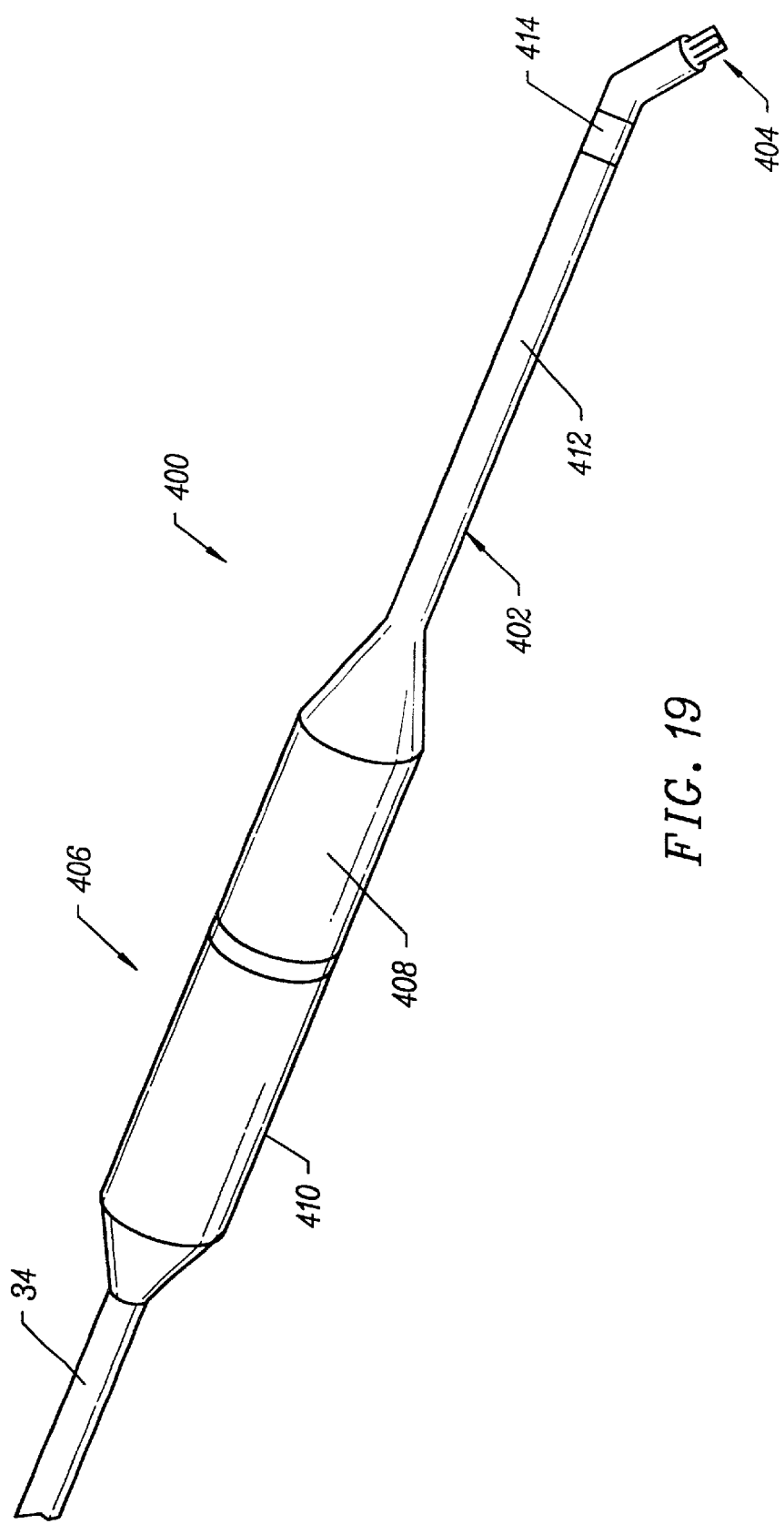
FIG. 19 illustrates a planar ablation probe for ablating tissue in confined spaces within a patient's body according to the present invention.

Referring to FIGS. 19–28, alternative systems and methods for ablating tissue in confined (e.g., narrow) body spaces will now be described. FIG. 19 illustrates an exemplary planar ablation probe 400 according to the present invention. Similar to the instruments described above, probe 400 can be incorporated into electrosurgical system 11 (or other suitable systems) for operation in either the bipolar or monopolar modalities. Probe 400 generally includes a support member 402, a distal working end 404 attached to the distal end of support member 402 and a proximal handle 408 attached to the proximal end of support member 402. As shown in FIG. 19, handle 406 includes a handpiece 408 and a power source connector 410 removably coupled to handpiece 408 for electrically connecting working end 404 with power supply 28 through cable 34 (see FIG. 1).

In the embodiment shown in FIG. 19, planar ablation probe 400 is configured to operate in the bipolar modality. Accordingly, support member 402 functions as the return electrode and comprises an electrically conducting material, such as titanium, or alloys containing one or more of nickel, chromium, iron, cobalt, copper, aluminum, platinum, molybdenum, tungsten, tantalum or carbon. In the preferred embodiment, support member 402 is an austenitic stainless steel alloy, such as stainless steel Type 304 from MicroGroup, Inc., Medway, Mass. As shown in FIG. 19, support member 402 is substantially covered by an insulating layer 412 to prevent electric current from damaging surrounding tissue. An exposed portion 414 of support member 402 functions as the return electrode for probe 400. Exposed portion 414 is preferably spaced proximally from active electrodes 416 by a distance of about 1 to 20 mm.

Figure 20:
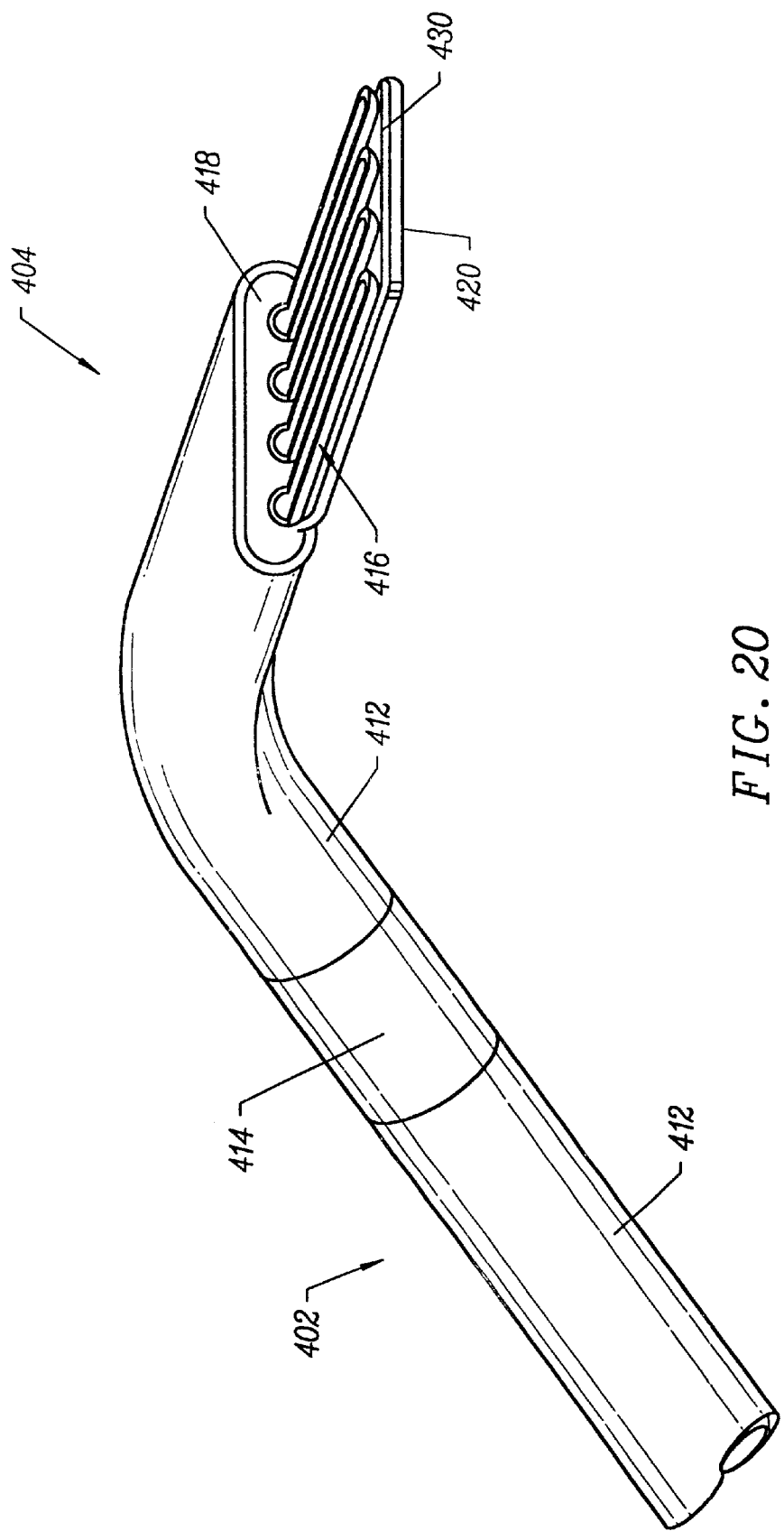
FIG. 20 illustrates a distal portion of the planar ablation probe of FIG. 19.
Figure 21A:
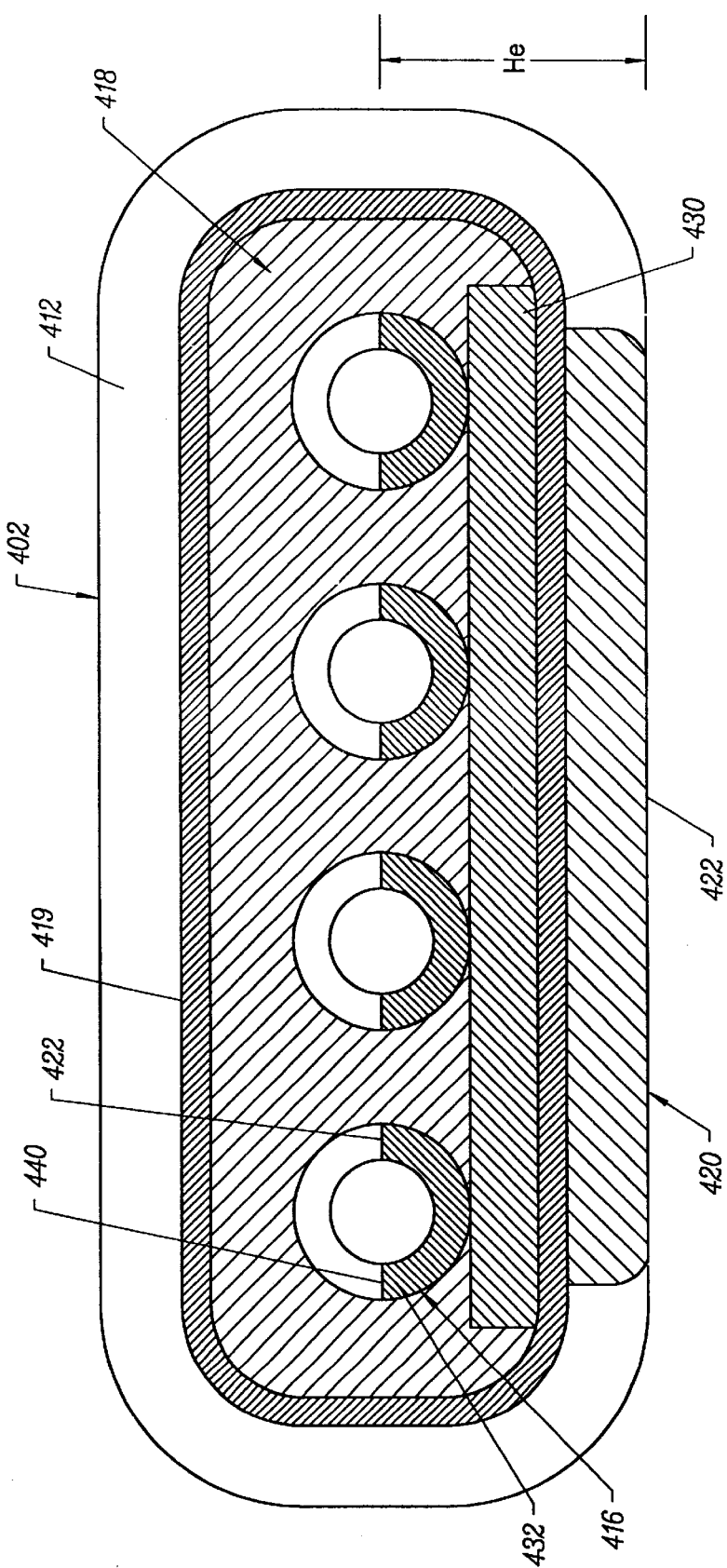
FIG. 21A is a front sectional view of the planar ablation probe, illustrating an array of semi-cylindrical active electrodes.

Referring to FIGS. 20 and 21, planar ablation probe 400 further comprises a plurality of active electrodes 416 extending from an electrically insulating spacer 418 at the distal end of support member 402. Of course, it will be recognized that probe 400 may include a single electrode depending on the size of the target tissue to be treated and the accessibility of the treatment site (see FIG. 26, for example). Insulating spacer 418 is preferably bonded to support member 402 with a suitable epoxy adhesive 419 to form a mechanical bond and a fluid-tight seal. Electrodes 416 usually extend about 2.0 mm to 20 mm from spacer 418, and preferably less than 10 mm. A support tongue 420 extends from the distal end of support member 402 to support active electrodes 416. Support tongue 420 and active electrodes 416 have a substantially low profile to facilitate accessing narrow spaces within the patient's body, such as the spaces between adjacent vertebrae and between articular cartilage and the meniscus in the patient's knee. Accordingly, tongue 420 and electrodes 416 have a substantially planar profile, usually having a combined height He of less than 4.0 mm, preferably less than 2.0 mm and more preferably less than 1.0 mm (see FIG. 25). In the case of ablation of meniscus near articular cartilage, the height He of both the tongue 420 and electrodes 416 is preferably between about 0.5 to 1.5 mm. The width of electrodes 416 and support tongue 420 will usually be less than 10.0 mm and preferably between about 2.0 to 4.0 mm.

Support tongue 420 includes a "non-active" surface 422 opposing active electrodes 416 covered with an electrically insulating layer (not shown) to minimize undesirable current flow into adjacent tissue or fluids. Non-active surface 422 is preferably atraumatic, i.e., having a smooth planar surface with rounded corners, to minimize unwanted injury to tissue or nerves in contact therewith, such as disc tissue or the nearby spinal nerves, as the working end of probe 400 is introduced into a narrow, confined body space. Non-active surface 422 of tongue 420 help to minimize iatrogenic injuries to tissue and nerves so that working end 404 of probe 400 can safely access confined spaces within the patient's body.

Figure 21B:
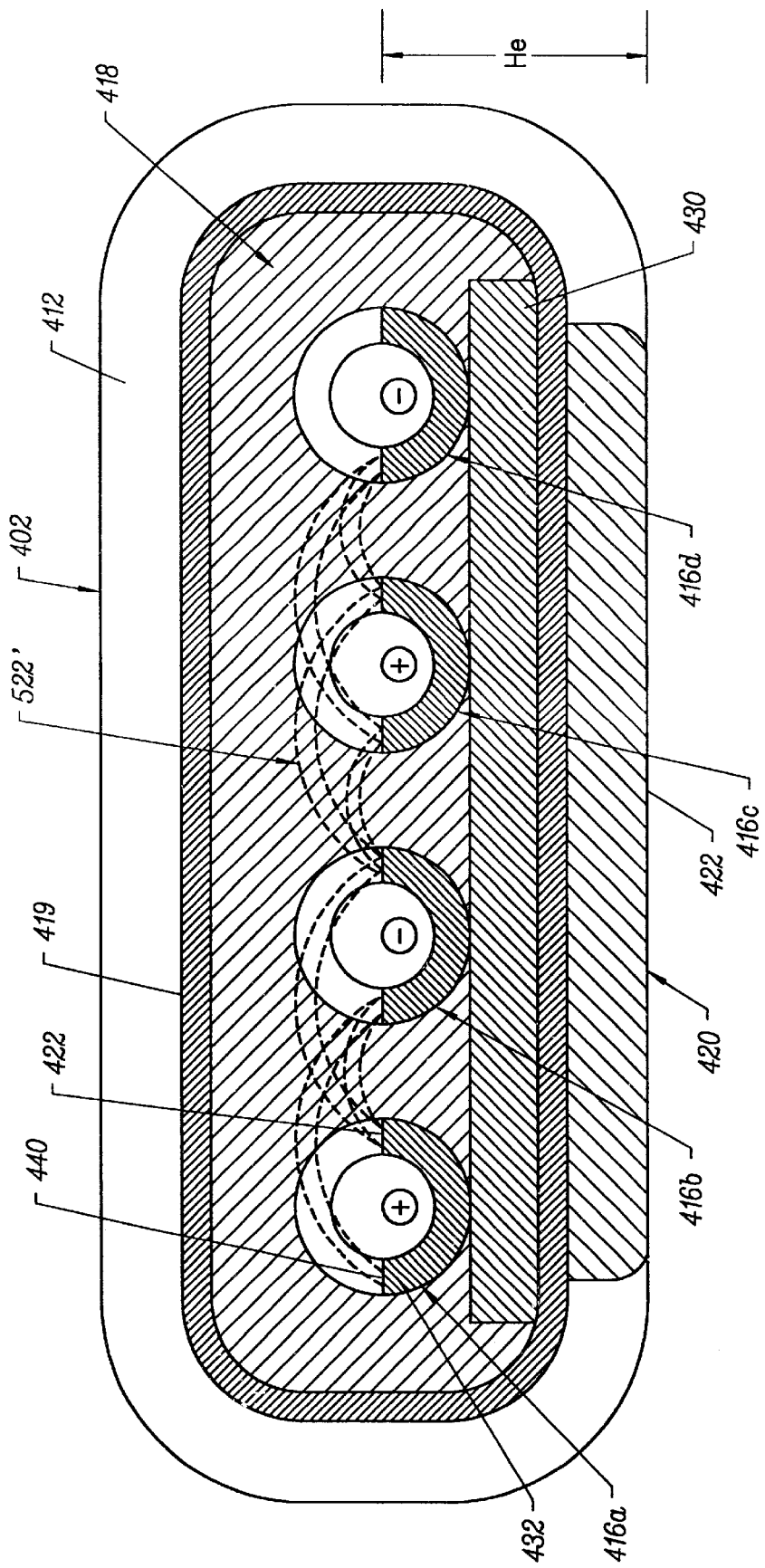
FIG. 21B is a front sectional view of an alternative planar ablation probe, illustrating an array of active electrodes having opposite polarities.
Figure 22:
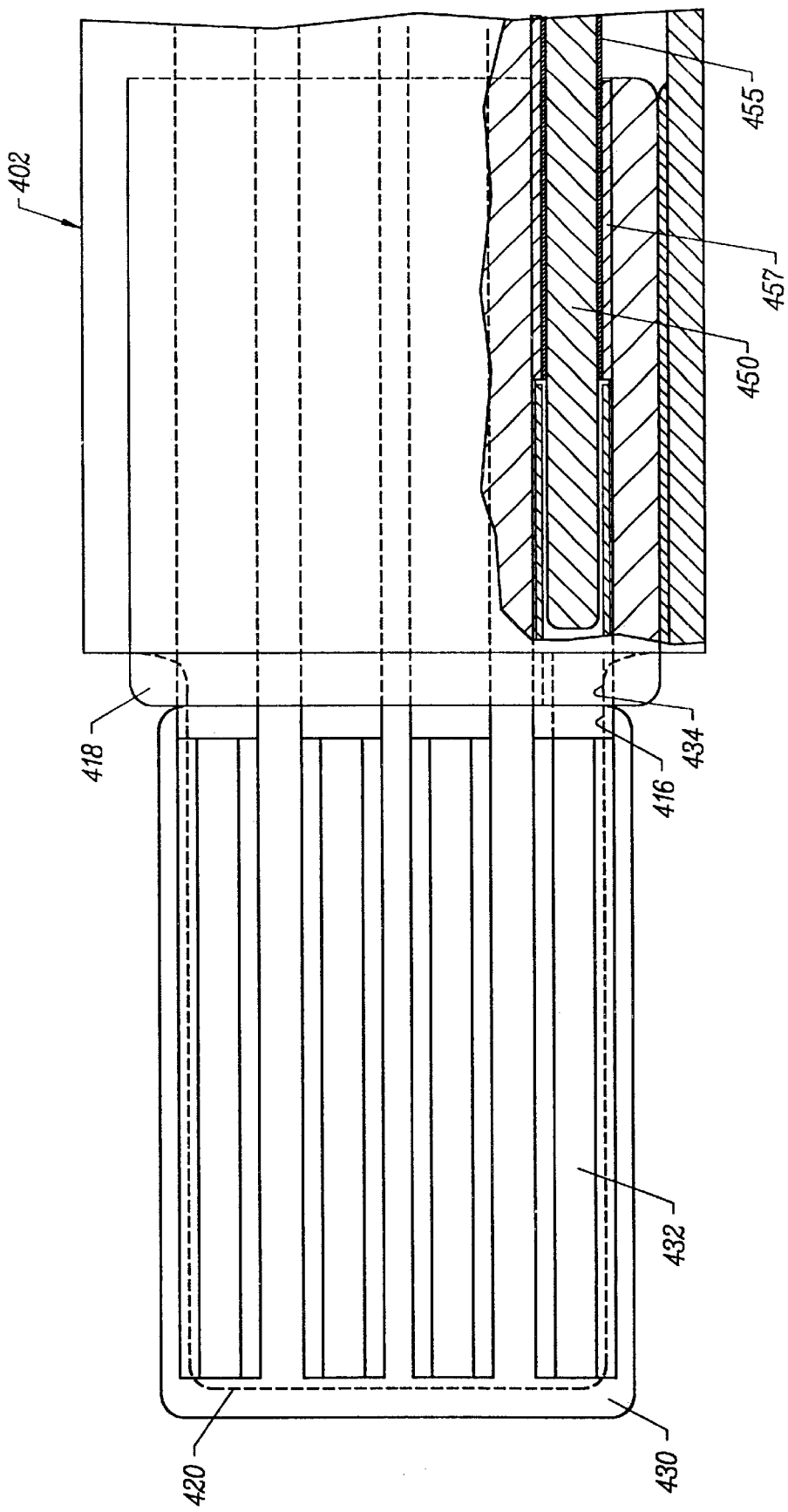
FIG. 22 is a top, partial section, view of the working end of the planar ablation probe of FIG. 19.
Figure 26:
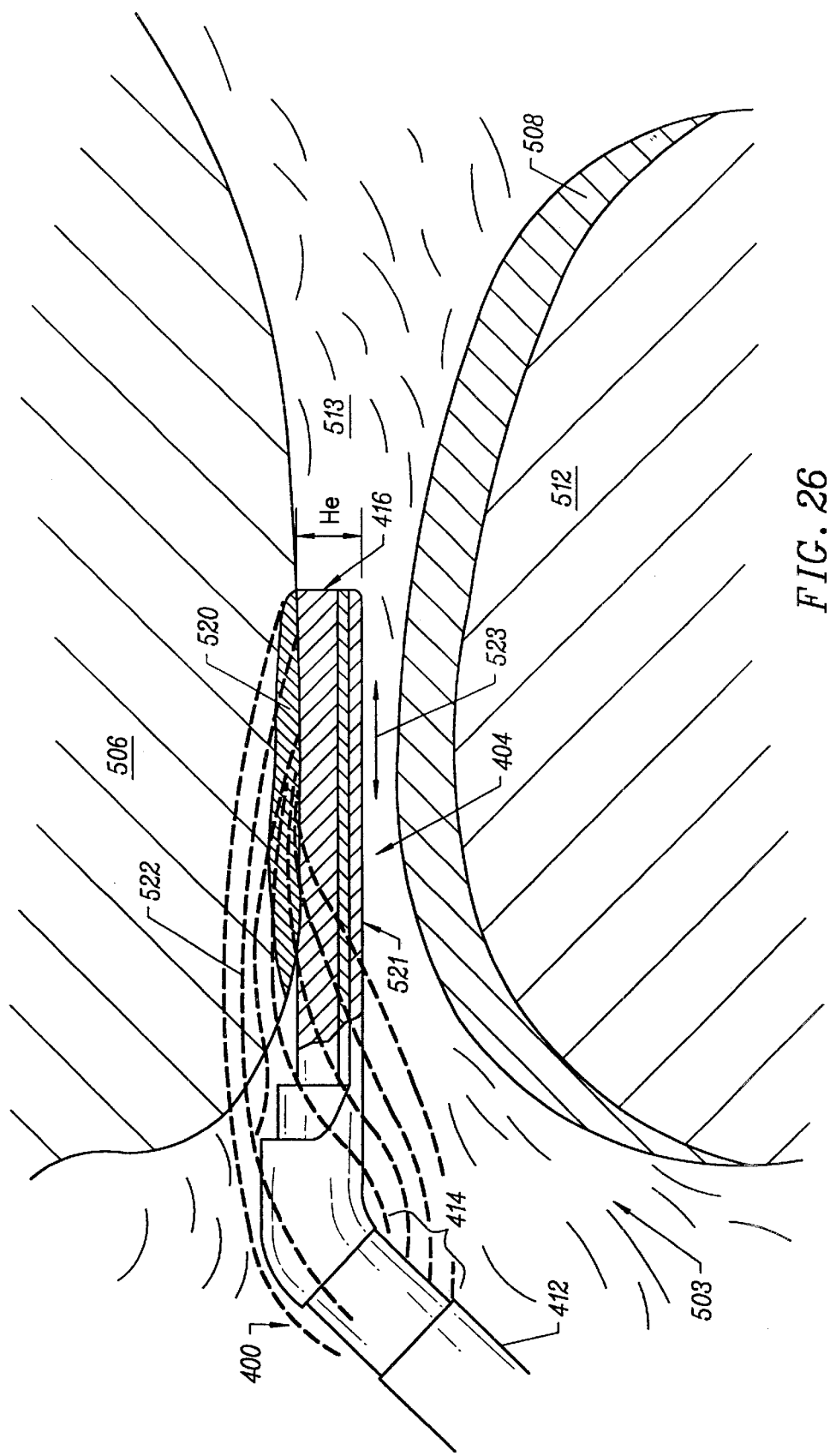
FIG. 26 is an enlarged view of the distal portion of the planar ablation probe, illustrating ablation or cutting of meniscus tissue.

Referring to FIGS. 21 and 22, an electrically insulating support member 430 is disposed between support tongue 420 and active electrodes 416 to inhibit or prevent electric current from flowing into tongue 420. Insulating member 430 and insulating layer 412 preferably comprise a ceramic, glass or glass ceramic material, such as alumina. Insulating member 430 is mechanically bonded to support tongue 420 with a suitable epoxy adhesive to electrically insulate active electrodes 416 from tongue 420. As shown in FIG. 26, insulating member 430 may overhang support tongue 420 to increase the electrical path length between the active electrodes 416 and the insulation covered support tongue 420.

Figure 23:
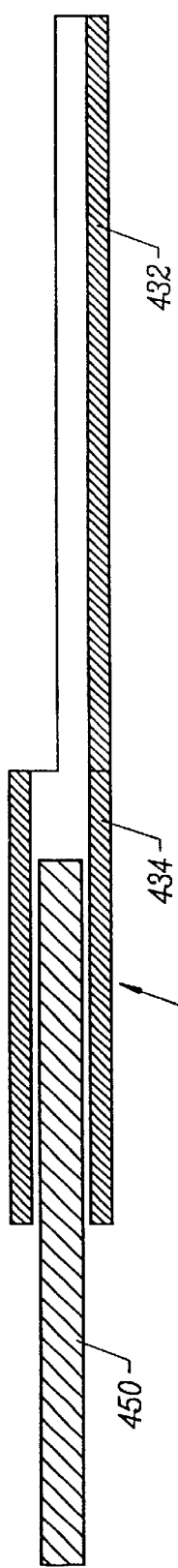
FIG. 23 is a side cross-sectional view of the working end of the planar ablation probe, illustrating the electrical connection with one of the active electrodes of FIG. 22.

As shown in FIGS. 21–23, active electrodes 416 are preferably constructed from a hollow, round tube, with at least the distal portion 432 of electrodes 416 being filed off to form a semi-cylindrical tube with first and second ends 440, 442 facing away from support tongue 420. Preferably, the proximal portion 434 of electrodes 416 will remain cylindrical to facilitate the formation of a crimp-type electrical connection between active electrodes 416 and lead wires 450 (see FIG. 23). As shown in FIG. 26, cylindrical proximal portions 434 of electrodes 416 extend beyond spacer 418 by a slight distance of 0.1 mm to 0.4 mm. The semi-cylindrical configuration of distal electrode portion 432 increases the electric field intensity and associated current density around the edges of ends 440, 442, as discussed above. Alternatively, active electrodes 416 may have any of the shapes and configurations described above or other configurations, such as square wires, triangular shaped wires, U-shaped or channel shaped wires and the like. In addition, the surface of active electrodes 416 may be roughened, e.g., by grit blasting, chemical or electrochemical etching, to further increase the electric field intensity and associated current density around distal portions 432 of electrodes 416.

Figure 24:
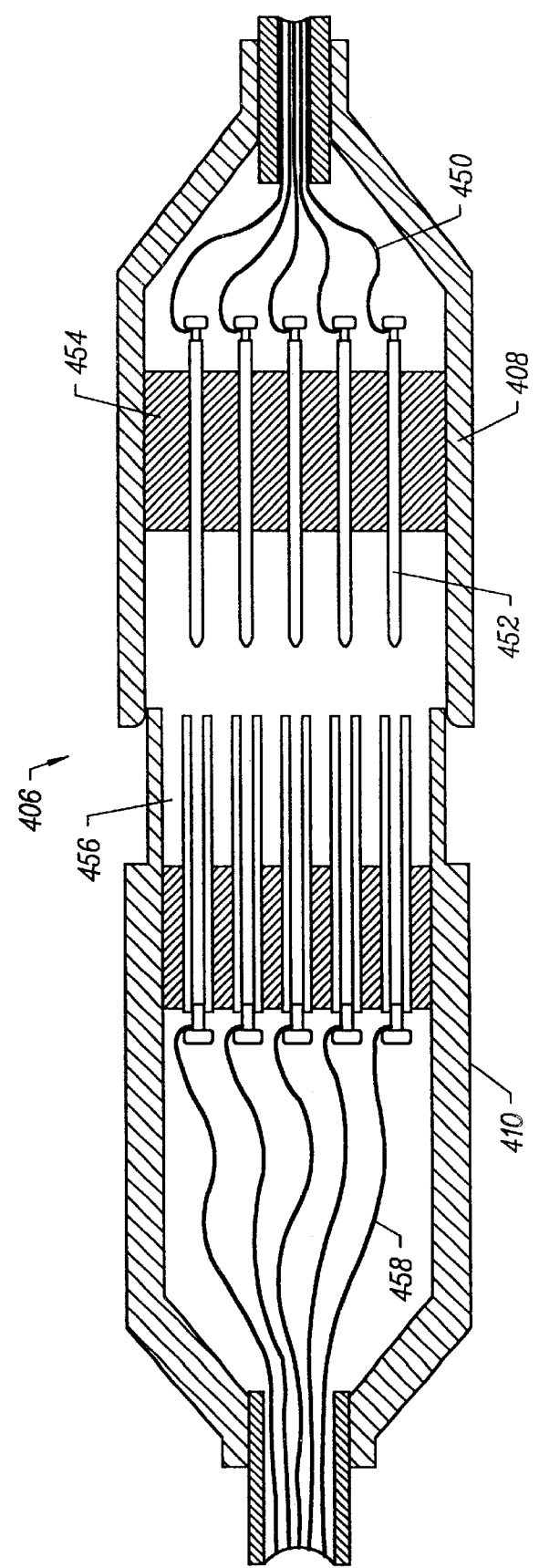
FIG. 24 is a side cross-sectional view of the proximal end of the planar ablation probe, illustrating the electrical connection with a power source connector.

As shown in FIG. 24, each lead wire 450 terminates at a connector pin 452 contained in a pin insulator block 454 within handpiece 408. Lead wires 450 are covered with an insulation layer (not shown), e.g., Tefzel™, and sealed from the inner portion of support member 402 with an adhesive seal 457 (FIG. 22). In the preferred embodiment, each electrode 416 is coupled to a separate source of voltage within power supply 28. To that end, connector pins 452 are removably coupled to mating receptacles 456 within connector 410 to provide electrical communication with active electrodes 416 and power supply 28 (FIG. 1). Electrically insulated lead wires 458 connect receptacles 456 to the corresponding sources of voltage within power supply 28. The electrically conductive wall 414 of support member 402 serves as the return electrode, and is suitably coupled to one of the lead wires 450.

In an alternative embodiment, adjacent electrodes 416 may be connected to the opposite polarity of source 28 so that current flows between adjacent active electrodes 416 rather than between active electrodes 416 and return electrode 414. By way of example, FIG. 21B illustrates a distal portion of a planar ablation probe 400' in which electrodes 416a and 416c are at one voltage polarity (i.e., positive) and electrodes 416b and 416d are at the opposite voltage polarity (negative). When a high frequency voltage is applied between electrodes 416a, 416c and electrodes 416b, 416d in the presence of electrically conducting liquid, current flows between electrodes 416a, 416c and 416b, 416d as illustrated by current flux lines 522'. Similar to the above embodiments, the opposite surface 420 of working end 404' of probe 400' is generally atraumatic and electrically insulated from active electrodes 416a, 416b, 416c and 416d to minimize unwanted injury to tissue in contact therewith.

In an exemplary configuration, each source of voltage includes a current limiting element or circuitry (not shown) to provide independent current limiting based on the impedance between each individual electrode 416 and return electrode 414. The current limiting elements may be contained within the power supply 28, the lead wires 450, cable 34, handle 406, or within portions of the support member 402 distal to handle 406. By way of example, the current limiting elements may include resistors, capacitors, inductors, or a combination thereof. Alternatively, the current limiting function may be performed by (1) a current sensing circuit which causes the interruption of current flow if the current flow to the electrode exceeds a predetermined value and/or (2) an impedance sensing circuit which causes the interruption of current flow (or reduces the applied voltage to zero) if the measured impedance is below a predetermined value. In another embodiment, two or more of the electrodes 416 may be connected to a single lead wire 450 such that all of the electrodes 416 are always at the same applied voltage relative to return electrode 414. Accordingly, any current lining elements or circuits will modulate the current supplied or the voltage applied to the array of electrodes 416, rather than limiting their current individually, as discussed in the previous embodiment.

Referring to FIGS. 25–28, methods for ablating tissue structures with planar ablation probe 400 according to the present invention will now be described. In particular, exemplary methods for treating a diseased meniscus within the knee (FIGS. 29–31) and for removing soft tissue between adjacent vertebrae in the spine (FIG. 32) will be described. In both procedures, at least the working end 404 of planar ablation probe 400 is introduced to a treatment site either by minimally invasive techniques or open surgery. Electrically conducting liquid is delivered to the treatment site, and voltage is applied from power supply 28 between active electrodes 416 and return electrode 414. The voltage is preferably sufficient to generate electric field intensities near active electrodes that form a vapor layer in the electrically conducting liquid, and induce the discharge of energy from the vapor layer to ablate tissue at the treatment site, as described in detail above.

Figure 25:
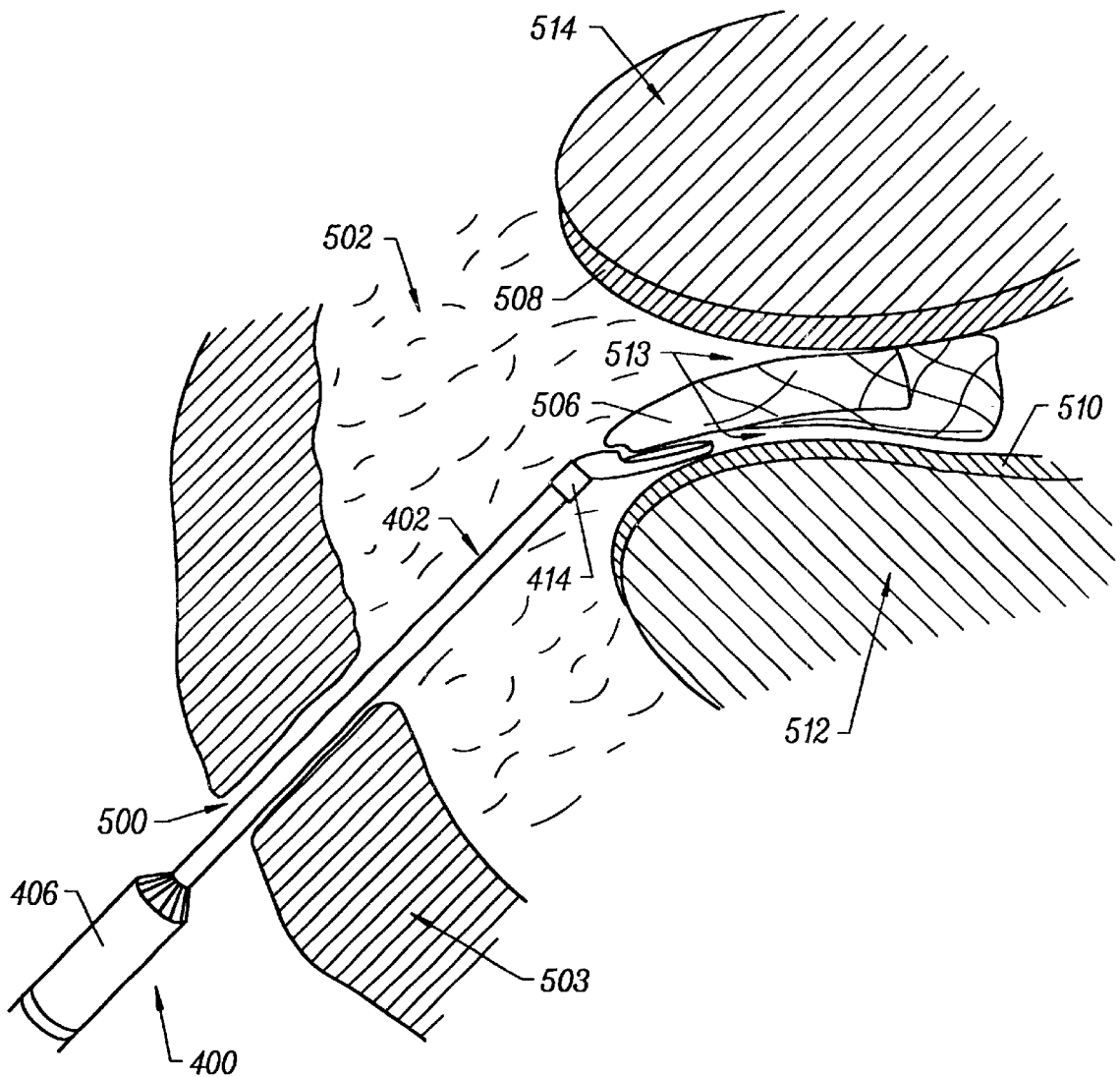
FIG. 25 is a schematic view illustrating the ablation of meniscus tissue located close to articular cartilage between the tibia and femur of a patient with the ablation probe of FIG. 19.

Referring to FIG. 25, working end 404 and at least the distal portion of support member 402 are introduced through a percutaneous penetration 500, such as a cannula, into the arthroscopic cavity 502. The insertion of probe 400 is usually guided by an arthroscope (not shown) which includes a light source and a video camera to allow the surgeon to selectively visualize a zone within the knee joint. To maintain a clear field of view and to facilitate the generation of a vapor layer, a transparent, electrically conductive irrigant 503, such as isotonic saline, is injected into the treatment site either through a liquid passage in support member 402 of probe 400, or through another instrument. Suitable methods for delivering irrigant to a treatment site are described in commonly assigned, co-pending application U.S. Pat. No. 5,697,281 filed on Jun. 7, 1995, previously incorporated herein by reference.

In the example shown in FIG. 25, the target tissue is a portion of the meniscus 506 adjacent to and in close proximity with the articular cartilage 510, 508 which normally covers the end surfaces of the tibia 512 and the femur 514, respectively. The articular cartilage 508, 510 is important to the normal functioning of joints, and once damaged, the body is generally not capable of regenerating this critical lining of the joints. Consequently, it is desirable that the surgeon exercise extreme care when treating the nearby meniscus 506 to avoid unwanted damage to the articular cartilage 508, 510. The confined spaces 513 between articular cartilage 508, 510 and meniscus 506 within the knee joint are relatively narrow, typically on the order of about 1.0 mm to 5.0 mm. Accordingly, the narrow, low profile working end 404 of ablation probe 400 is ideally suited for introduction into these confined spaces 513 to the treatment site. As mentioned previously, the substantially planar arrangement of electrodes 416 and support tongue 420 (typically having a combined height of about 0.5 to 1.5 mm) allows the surgeon to deliver working end 404 of probe 400 into the confined spaces 513, while minimizing contact with the articular cartilage 508, 510 (see FIG. 26).

As shown in FIG. 26, active electrodes 416 are disposed on one face of working end 404 of probe 400. Accordingly, a zone 520 of high electric field intensity is generated on each electrode 416 on one face of working end 404 while the opposite side 521 of working end 404 is atraumatic with respect to tissue. In addition, the opposite side 521 is insulated from electrodes 416 to minimize electric current from passing through this side 521 to the tissue (i.e., adjacent articular cartilage 508). As shown in FIGS. 26, the bipolar arrangement of active electrodes 416 and return electrode 414 causes electric current to flow along flux lines 522 predominantly through the electrically conducting irrigant 503, which envelops the tissue and working end 404 of ablation probe 400 and provides an electrically conducting path between electrodes 416 and return electrode 414. As electrodes 416 are engaged with, or positioned in close proximity to, the target meniscus 506, the high electric field present at the electrode edges cause controlled ablation of the tissue by forming a vapor layer and inducing the discharge of energy therefrom. In addition, the motion of electrodes 416 relative to the meniscus 506 (as shown by vector 523) causes tissue to be removed in a controlled manner. The presence of the irrigant also serves to minimize the increase in the temperature of the meniscus during the ablation process because the irrigant generally comes in contact with the treated tissue shortly after one of the electrodes 416 has been translated across the surface of the tissue.

Figure 28:
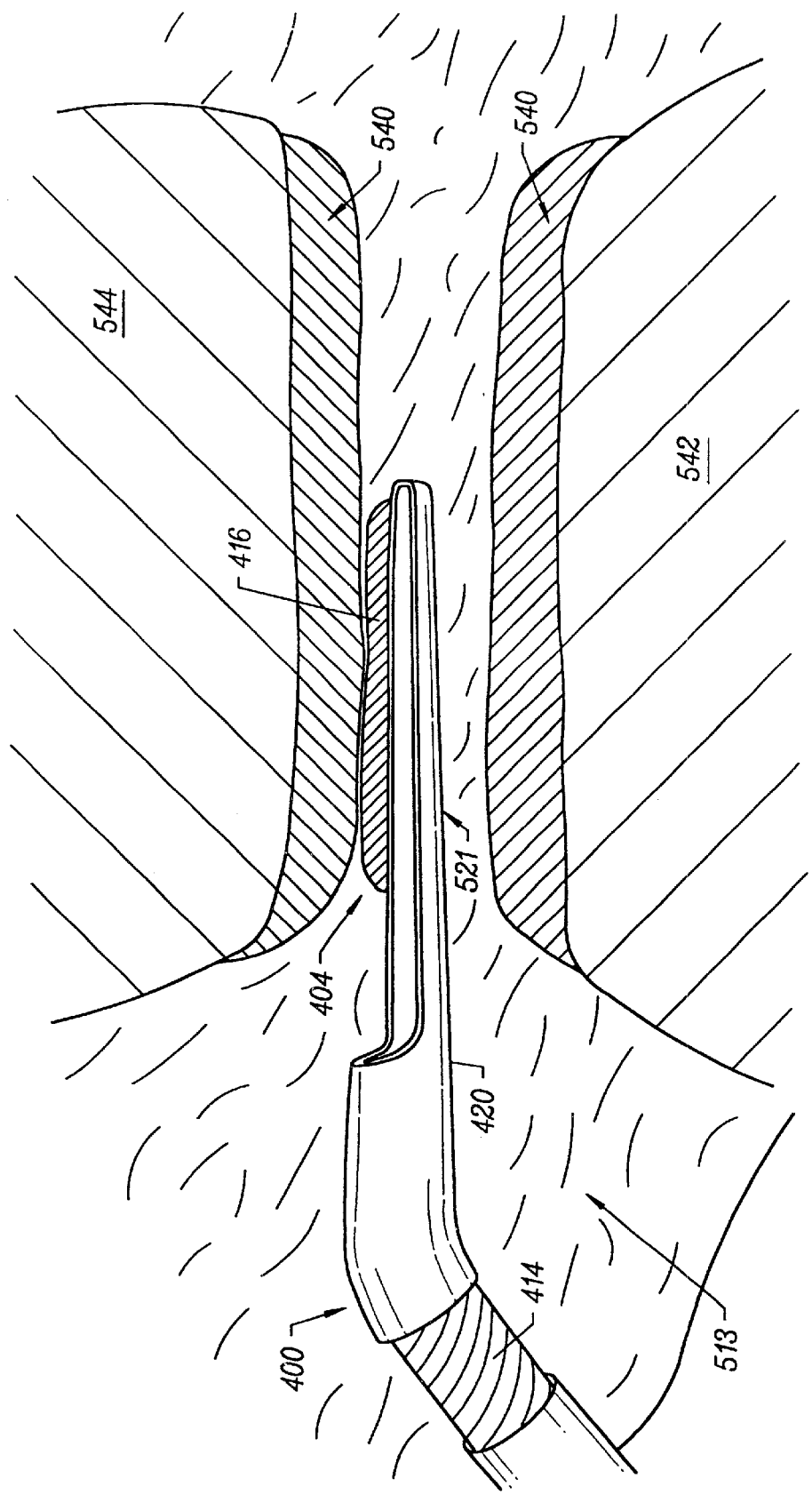
FIG. 28 is a schematic view illustrating the ablation of soft tissue from adjacent surfaces of the vertebrae with the planar ablation probe of the present invention.

Referring now to FIG. 28, an exemplary method for removing soft tissue 540 from the surfaces of adjacent vertebrae 542, 544 in the spine will now be described. Removal of this soft tissue 540 is often necessary, for example, in surgical procedures for fusing or joining adjacent vertebrae together. Following the removal of tissue 540, the adjacent vertebrae 542, 544 are stabilized to allow for subsequent fusion together to form a single monolithic vertebra. As shown, the low-profile of working end 404 of probe 400 (i.e., thickness values as low as 0.2 mm) allows access to and surface preparation of closely spaced vertebrae. In addition, the shaped electrodes 416 promote substantially high electric field intensities and associated current densities between active electrodes 416 and return electrode 414 to allow for the efficient removal of tissue attached to the surface of bone without significantly damaging the underlying bone. The "non-active" insulating side 521 of working end 404 also minimizes the generation of electric fields on this side 521 to reduce ablation of the adjacent vertebra 542.

The target tissue is generally not completely immersed in electrically conductive liquid during surgical procedures within the spine, such as the removal of soft tissue described above. Accordingly, electrically conducting liquid will preferably be delivered into the confined spaces 513 between adjacent vertebrae 542, 544 during this procedure. The fluid may be delivered through a liquid passage (not shown) within support member 402 of probe 400, or through another suitable liquid supply instrument.

Figure 27:
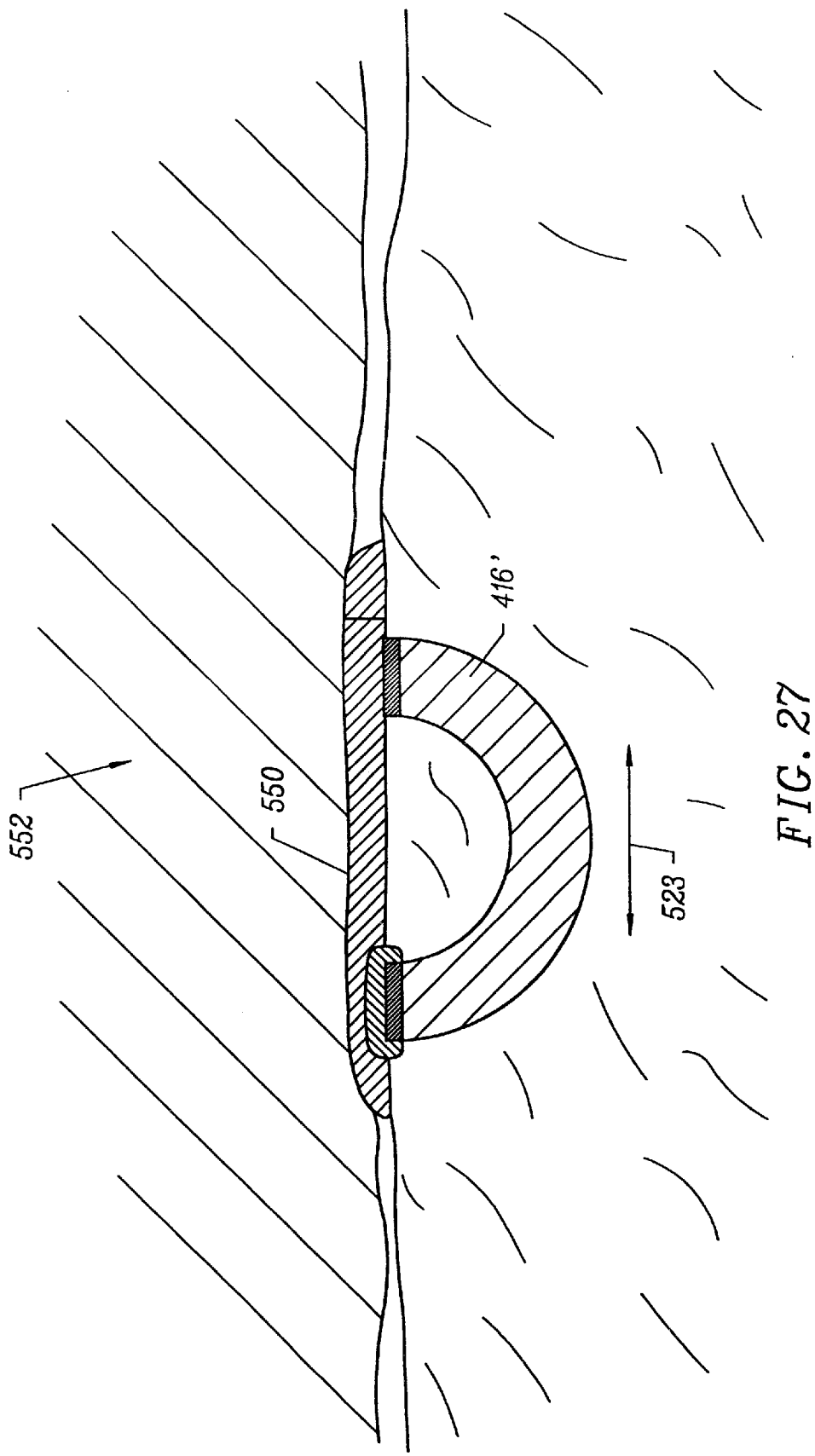
FIG. 27 illustrates a method of ablating tissue with a planar ablation probe incorporating a single active electrode.
Figure 31:
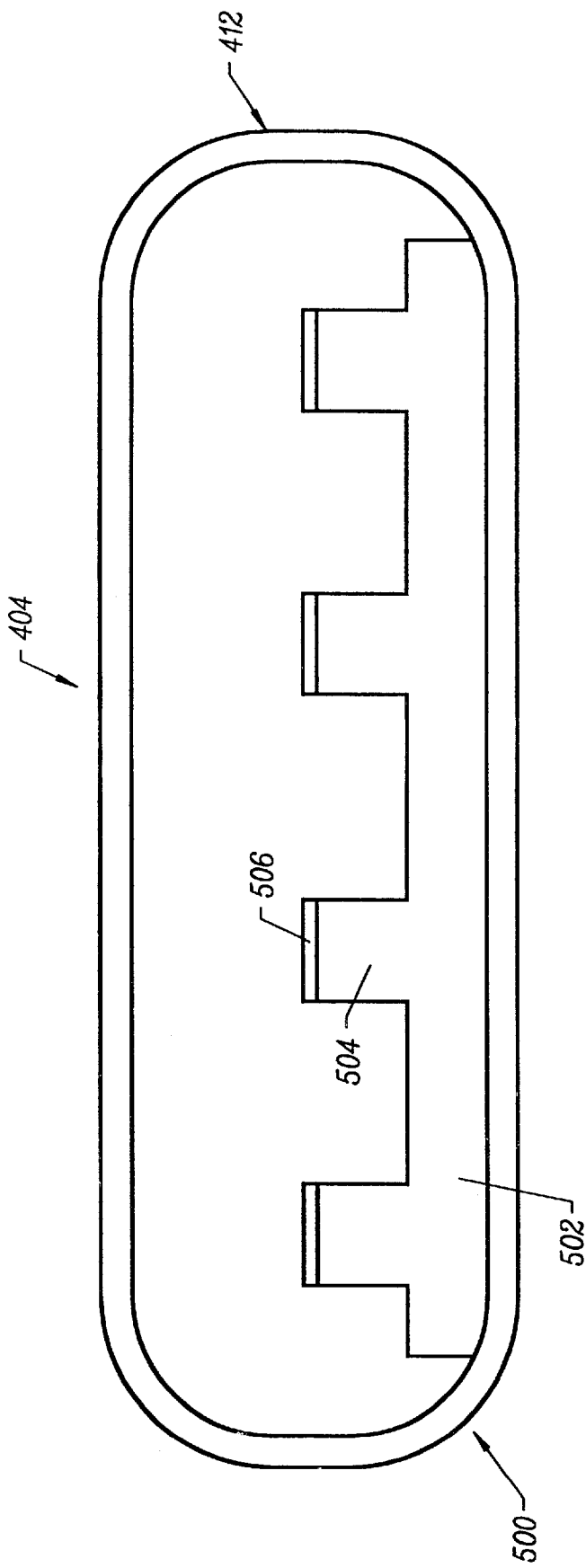
FIG. 31 is an end view of the probe of FIG. 30.

Other modifications and variations can be made to disclose embodiments without departing from the subject invention as defined in the following claims. For example, it should be clearly understood that the planar ablation probe 400 described above may incorporate a single active electrode, rather than a plurality of such active electrodes as described above in the exemplary embodiment. FIG. 27 illustrates a portion of a planar ablation probe according to the present invention that incorporates a single active electrode 416' for generating high electric field densities 550 to ablate a target tissue 552. Electrode 416' may extend directly from a proximal support member, as depicted in FIG. 31, or it may be supported on an underlying support tongue (not shown) as described in the previous embodiment. As shown, the representative single active electrode 416' has a semicylindrical cross-section, similar to the electrodes 416 described above. However, the single electrode 416' may also incorporate any of the above described configurations (e.g., square or star shaped solid wire) or other specialized configurations depending on the function of the device.

Figure 29:
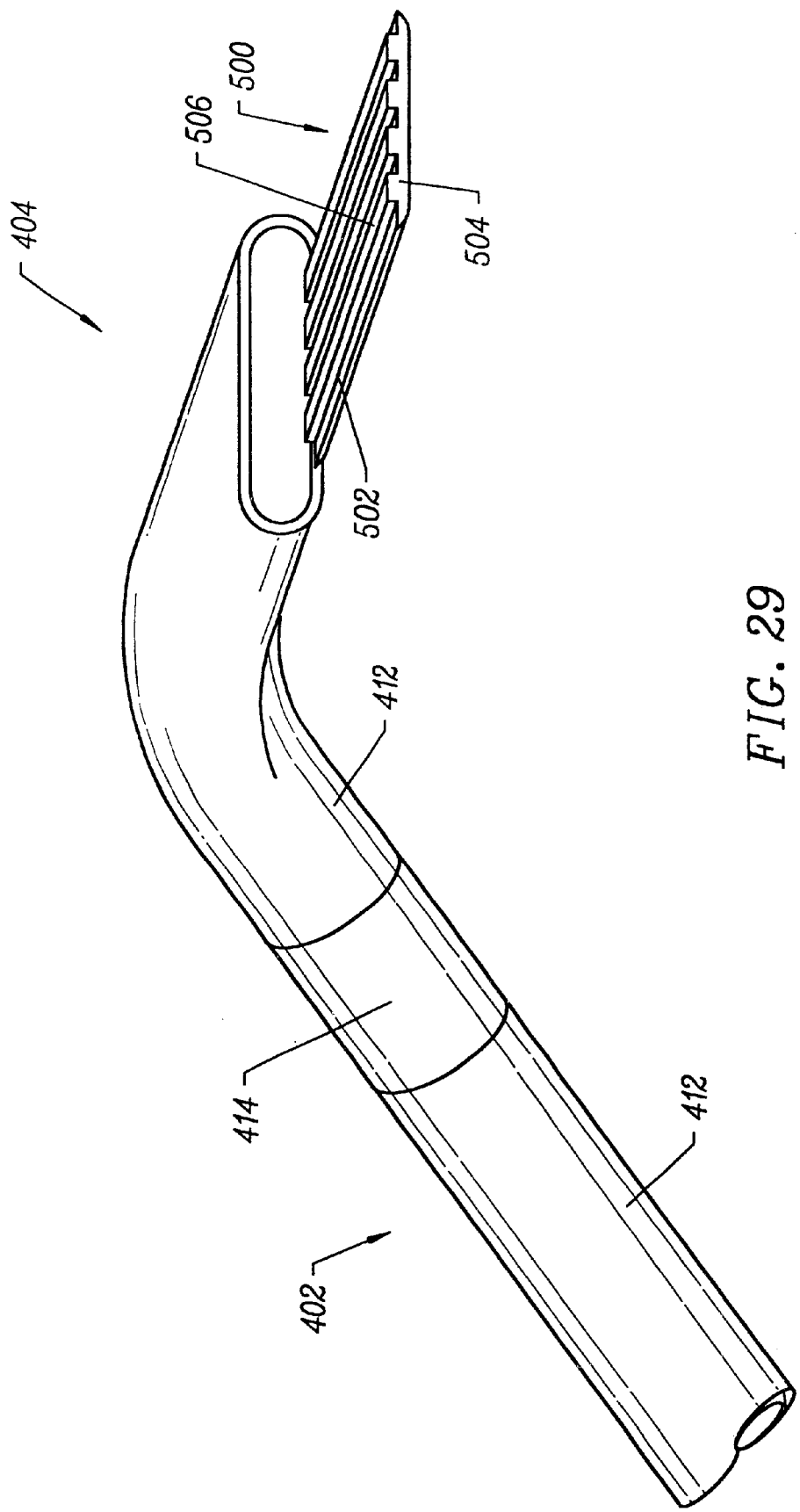
FIG. 29 is a perspective view of an alternative embodiment of the planar ablation probe incorporating a ceramic support structure with conductive strips printed thereon.
Figure 30:
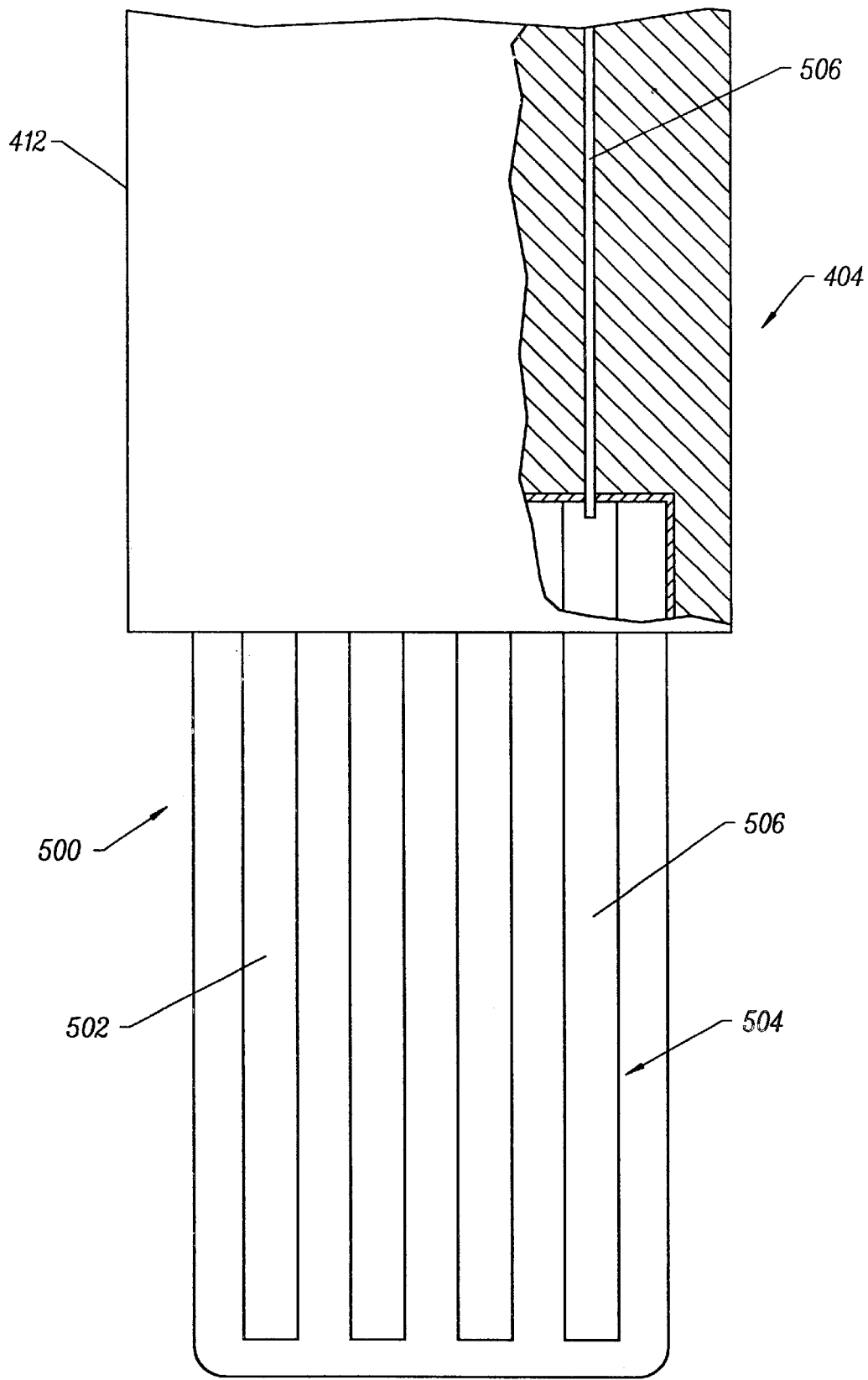
FIG. 30 is a top partial cross-sectional view of the planar ablation probe of FIG. 29.

Referring now to FIGS. 29–31 an alternative electrode support member 500 for a planar ablation probe 404 will be described in detail. As shown, electrode support member 500 preferably comprises a multilayer or single layer substrate 502 comprising a suitable high temperature, electrically insulating material, such as ceramic. The substrate 502 is a thin or thick film hybrid having conductive strips that are adhered to, e.g., plated onto, the ceramic wafer. The conductive strips typically comprise tungsten, gold, nickel or equivalent materials. In the exemplary embodiment, the conductive strips comprise tungsten, and they are co-fired together with the wafer layers to form an integral package. The conductive strips are coupled to external wire connectors by holes or vias that are drilled through the ceramic layers, and plated or otherwise covered with conductive material.

In the representative embodiment, support member 500 comprises a single ceramic wafer having a plurality of longitudinal ridges 504 formed on one side of the wafer 502. Typically, the wafer 502 is green pressed and fired to form the required topography (e.g., ridges 504). A conductive material is then adhered to the ridges 502 to form conductive strips 506 extending axially over wafer 502 and spaced from each other. As shown in FIG. , the conductive strips 506 are attached to lead wires 508 within shaft 412 of the probe 404 to electrically couple conductive strips 506 with the power supply 28 (FIG. 1). This embodiment provides a relatively low profile working end of probe 404 that has sufficient mechanical structure to withstand bending forces during the procedure.

FIGS. 34–36 illustrate another system and method- for treating swollen or herniated spinal discs according to the present invention. In this procedure, an electrosurgical probe 700 comprises a long, thin shaft 702 (e.g., on the order of about 1 mm in diameter or less) that can be percutaneously introduced anteriorly through the abdomen or thorax, or through the patient's back directly into the spine. The probe shaft 702 will include one or more active electrode(s) 704 for applying electrical energy. to tissues within the spine. The probe 700 may include one or more return electrode(s) 706, or the return electrode may be positioned on the patient's back, as a dispersive pad (not shown).

As shown in FIG. 34, the distal portion of shaft 702 is introduced anteriorly through a small percutaneous penetration into the annulus 710 of the target spinal disc. To facilitate this process, the distal end of shaft 702 may taper down to a sharper point (e.g., a needle), which can then be retracted to expose active electrode(s) 704. Alternatively, the electrodes may be formed around the surface of the tapered distal portion of shaft (not shown). In either embodiment, the distal end of shaft is delivered through the annulus 710 to the target nucleus pulposis 290, which may be herniated, extruded, non-extruded, or simply swollen. As shown in FIG. 35, high frequency voltage is applied between active electrode(s) 704 and return electrode(s) 710 to heat the surrounding collagen to suitable temperatures for contraction (i.e., typically about 55° C. to about 70° C.). As discussed above, this procedure may be accomplished with a monopolar configuration, as well. However, applicant has found that the bipolar configuration shown in FIGS. 34–36 provides enhanced control of the high frequency current, which reduces the risk of spinal nerve damage.

As shown in FIGS. 35 and 36, once the pulposis 290 has been sufficient contracted to retract from impingement on the nerve 720, the probe 700 is removed from the target site. In the representative embodiment, the high frequency voltage is applied between active and return electrode(s) 704 706 as the probe is withdrawn through the annulus 710. This voltage is sufficient to cause contraction of the collagen fibers within the annulus 710, which allows the annulus 710 to contract around the hole formed by probe 700, thereby improving the healing of this hole. Thus, the probe 700 seals its own passage as it is withdrawn from the disc.

Other modifications and variations can be made to disclose embodiments without departing from the subject invention as defined in the following claims. For example, it should be noted that the invention is not limited to an electrode array comprising a plurality of electrode terminals. The invention could utilize a plurality of return electrodes, e.g., in a bipolar array or the like. In addition, depending on other conditions, such as the peak-to-peak voltage, electrode diameter, etc., a single electrode terminal may be sufficient to contract collagen tissue, ablate tissue, or the like.

In addition, the active and return electrodes may both be located on a distal tissue treatment surface adjacent to each other. The active and return electrodes may be located in active/return electrode pairs, or one or more return electrodes may be located on the distal tip together with a plurality of electrically isolated electrode terminals. The proximal return electrode may or may not be employed in these embodiments. For example, if it is desired to maintain the current flux lines around the distal tip of the probe, the proximal return electrode will not be desired.

What is claimed is:

1. A method for treating an intervertebral disc within a patient's spine, comprising:
   positioning at least one active electrode terminal within close proximity of the disc; and
   applying a high frequency voltage between the at least one active electrode terminal and a return electrode, the voltage being sufficient to remove a portion of a nucleus pulposus to reduce a volume of the disc.

2. The method of claim 1, further comprising:
   introducing the at least one active electrode terminal into the nucleus pulposus via an opening in an annulus fibrosus of the disc.

3. The method of claim 1, wherein an extruded portion of the nucleus pulposus lies external to an annulus fibrosus of the disc, and the method further comprises positioning the at least one active electrode terminal adjacent to or within the extruded portion of the nucleus pulposus.

4. The method of claim 1, further comprising: delivering electrically conductive fluid between the at least one active electrode terminal and the nucleus pulposus tissue.

5. The method of claim 4, further comprising: positioning the return electrode within the electrically conductive fluid, wherein the electrically conductive fluid completes a current flow path between the at least one active electrode terminal and the return electrode.

6. The method of claim 4, further comprising: applying sufficient voltage to the at least one active electrode terminal in the presence of the electrically conductive fluid to vaporize at least a portion of the electrically conductive fluid at a location between the at least one active electrode terminal and the nucleus pulposus tissue.

7. The method of claim 6, further comprising: accelerating charged particles from the vaporized electrically conductive fluid to the nucleus pulposus tissue to cause dissociation of the molecular bonds within the nucleus pulposus tissue.

8. The method of claim 1, further comprising: positioning the return electrode on an outer surface of the patient's body, and conducting electric current from the at least one active electrode terminal, through the patient's body, to the return electrode.

9. The method of claim 1, wherein the at least one active electrode terminal comprises a single, active electrode terminal at the distal end of a shaft.

10. The method of claim 1, wherein the at least one active electrode terminal comprises a plurality of electrically isolated active electrode terminals at the distal end of a shaft.

11. The method of claim 1, further comprising: during said applying step, aspirating fluid from within the nucleus pulposus.

12. The method of claim 10, further comprising: independently controlling current flow from at least two of the plurality of active electrode terminals based on impedance between each of the plurality of active electrode terminals and the return electrode.

13. The method of claim 1, further comprising:

aspirating tissue fragments from the disc through an aspiration lumen of an instrument; and applying high frequency voltage to an aspiration electrode coupled to the aspiration lumen, the high frequency voltage applied to the aspiration electrode being sufficient to remove at least a portion of the tissue fragments.

14. The method of claim 13, wherein the aspiration electrode comprises a screen electrode located across a distal opening of the aspiration lumen, and the screen electrode having a plurality of openings for aspiration of tissue fragments therethrough.

15. A method for ablating nucleus pulposus tissue from an intervertebral disc within a patient's spine, the method comprising:

a) positioning at least one active electrode terminal within a nucleus pulposus of the disc; and b) applying a high frequency voltage between the at least one active electrode terminal and a return electrode, the applied voltage being sufficient to ablate the nucleus pulposus tissue, wherein a portion of the nucleus pulposus is removed and a volume of the disc is decreased.

16. The method of claim 15, further comprising:

c) prior to said steps a) and b), providing an electrosurgical probe including a shaft having a shaft distal end, wherein said positioning step comprises positioning the shaft distal end within the nucleus pulposus, and wherein the at least one active electrode terminal and the return electrode are disposed at the shaft distal end.

17. The method of claim 16, further comprising:

f) during said applying step, deflecting the shaft distal end to produce a bore within the nucleus pulposus.

18. The method of claim 15, wherein during said applying step, the nucleus pulposus tissue is ablated via molecular dissociation of components of the nucleus pulposus tissue.

19. The method of claim 15, further comprising:

d) during said applying step, axially translating the at least one active electrode terminal within the nucleus pulposus.

20. The method of claim 19, further comprising:

e) during said applying step, rotating the at least one active electrode terminal within the nucleus pulposus.

21. The method of claim 15, wherein the at least one active electrode terminal comprises an array of active electrode terminals, and said applying step comprises applying the high frequency voltage between the return electrode and the array of active electrode terminals.

22. A method of decreasing the volume of an intervertebral disc, comprising:

a) providing an electrosurgical probe, the probe including a distal working end, at least one active electrode terminal disposed at the working end, and a return electrode disposed at the working end;

b) positioning the working end of the probe within the disc such that both the at least one active electrode terminal and the return electrode are positioned within the nucleus pulposus; and c) while both the at least one active electrode terminal and the return electrode are positioned according to said step b), applying a high frequency voltage between the return electrode and the at least one active electrode terminal, wherein the applied voltage effects ablation of a portion of the nucleus pulposus.

23. The method of claim 22, further comprising:

d) while the at least one active electrode terminal and the return electrode are positioned within the nucleus pulposus according to said step b), and prior to said step c), limiting axial travel of the probe.

24. The method of claim 23, wherein the disc includes an annulus fibrosus external to the nucleus pulposus, wherein said step d) anchors the working end of the probe within the nucleus pulposus, and prevents movement of the working end towards the annulus fibrosus during said step c).

25. The method of claim 23, wherein said step d) allows for ablation of the nucleus pulposus while preventing ablation of the annulus fibrosus.

26. The method of claim 23, wherein the probe includes a mechanical stop, and wherein limiting the axial travel of the probe is effected via the mechanical stop.

27. The method of claim 22, wherein the disc includes an annulus fibrosus external to the nucleus pulposus, and said step b) comprises positioning both the at least one active electrode terminal and the return electrode within the nucleus pulposus at a location remote from the annulus fibrosus.

28. The method of claim 22, wherein the disc includes an annulus fibrosus external to the nucleus pulposus, and wherein the voltage applied in said step c) has substantially no effect on the annulus fibrosus.

29. The method of claim 22, wherein the probe further includes an aspiration lumen and an aspiration electrode coupled to the aspiration lumen, and the method further comprises:

e) aspirating tissue fragments from the disc towards the aspiration lumen; and f) applying high frequency voltage to the aspiration electrode, the high frequency voltage applied to the aspiration electrode being sufficient to ablate at least a portion of the tissue fragments.

30. The method of claim 29, wherein the aspiration electrode comprises a screen electrode located across a distal opening of the aspiration lumen, the screen electrode having a plurality of openings therein, and the plurality of openings for aspiration of tissue fragments therethrough.

31. The method of claim 22, further comprising:

g) delivering an electrically conductive fluid to the working end of the probe, wherein the electrically conductive fluid provides a current flow path between the at least one active electrode terminal and the return electrode.

32. The method of claim 22, further comprising:

h) during said applying step, translating the at least one active electrode terminal within the nucleus pulposus.

* * * * *

UNITED STATES PATENT AND TRADEMARK OFFICE
CERTIFICATE OF CORRECTION

| | | |
|---|---|---|
| PATENT NO. | : 6,540,741 B1 | Page 1 of 1 |
| APPLICATION NO. | : 09/412103 | |
| DATED | : April 1, 2003 | |
| INVENTOR(S) | : Ronald A. Underwood et al. | |

It is certified that error appears in the above-identified patent and that said Letters Patent is hereby corrected as shown below:

On the Title Page, Item (60), delete Related U.S. Application Data, on the front page of the patent, "now Pat. No. 6,159,184", and replace with "now Pat. No. 6,159,194".

Column 1, Line 14, delete "U.S. Pat. No. 6,159,184", and replace with "U.S. Patent No. 6,159,194".

Signed and Sealed this

Thirty-first Day of March, 2009

JOHN DOLL
*Acting Director of the United States Patent and Trademark Office*